(12) United States Patent
Volpe et al.

(10) Patent No.: US 11,040,951 B2
(45) Date of Patent: Jun. 22, 2021

(54) METHODS AND COMPOSITIONS RELATING TO GENOTOXIN COLIBACTIN

(71) Applicant: PRESIDENT AND FELLOWS OF HARVARD COLLEGE, Cambridge, MA (US)

(72) Inventors: Matthew R. Volpe, Cambridge, MA (US); Emily Patricia Balskus, Somerville, MA (US); Matthew Ryan Wilson, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 16/542,583

(22) Filed: Aug. 16, 2019

(65) Prior Publication Data
US 2020/0055836 A1 Feb. 20, 2020

Related U.S. Application Data

(60) Provisional application No. 62/719,325, filed on Aug. 17, 2018.

(51) Int. Cl.
*C07D 311/16* (2006.01)
*G01N 33/58* (2006.01)

(52) U.S. Cl.
CPC ......... *C07D 311/16* (2013.01); *G01N 33/582* (2013.01)

(58) Field of Classification Search
CPC .................. C07D 311/16; G01N 33/582
See application file for complete search history.

(56) References Cited

U.S. PATENT DOCUMENTS

2021/0010051 A1  1/2021  Watanabe et al.

FOREIGN PATENT DOCUMENTS

WO     WO-2020037009 A1 *  2/2020  ............. C07H 19/06

OTHER PUBLICATIONS

Wislicenus, J. "Adolph Strecker's Short Textbook of Organic Chemistry" 1881, Spottiswoode: London, pp. 38-39.*
Cougnoux et al. "Small-molecule inhibitors prevent the genotoxic and protumoural effects induced by colibactin-producing bacteria." Gut 65(2): 278-285 (2016).

* cited by examiner

*Primary Examiner* — David K O'Dell
(74) *Attorney, Agent, or Firm* — Nixon Peabody LLP; David S. Resnick; Nicole D. Kling

(57) ABSTRACT

The technology described herein is directed to compounds which are substrates for ClbP, acting as fluorescent probes for ClbP activity. Further provided herein are methods for measuring ClbP activity, screening for ClbP inhibitors, detecting colibactin, and/or diagnosing cancer, which utilize the substrate compounds.

7 Claims, 17 Drawing Sheets

Specification includes a Sequence Listing.

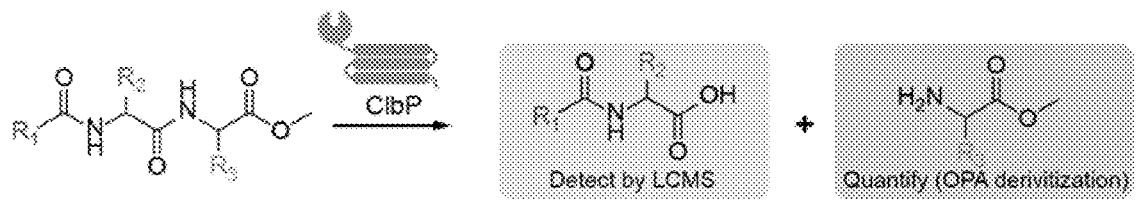

| | $R_1$ | $R_2$ | $R_3$ | Pdt detected? (LCMS) | $k_{cat}$ (min$^{-1}$) | $K_M$ (μM) | $k_{cat}/K_M$ (M$^{-1}$s$^{-1}$) |
|---|---|---|---|---|---|---|---|
| (1) | $C_{13}H_{27}$ | $CH_2CONH_2$ (R) | $CH_3$ (S) | Yes | 36 ± 4 | 130 ± 26 | 0.28 |
| (2) | (4-Ph)-$C_3H_6$ | $CH_2CONH_2$ (R) | $CH_3$ (S) | Yes | 80 ± 13 | 246 ± 70 | 0.33 |
| (3) | $C_3H_7$ | $CH_2CONH_2$ (R) | $CH_3$ (S) | Yes | 28 ± 15 | 680 ± 470 | 0.04 |
| (4) | $CH_3$ | $CH_2CONH_2$ (R) | $CH_3$ (S) | Yes | | | |
| (5) | (8-$NH_2$)$C_7H_{15}$ | $CH_2CONH_2$ (R) | $CH_3$ (S) | Yes | | | |
| (6) | $C_{13}H_{27}$ | $CH_2CO_2H$ (R) | $CH_3$ (S) | Trace | | | |
| (7) | $C_{13}H_{27}$ | $CH_2CONH_2$ (S) | $CH_3$ (S) | No | | | |
| (8) | $C_{13}H_{27}$ | $CH_2CH_2CONH_2$ | $CH_3$ (S) | No | | | |
| (9) | $C_{13}H_{27}$ | $CH_3$ (R) | $CH_3$ (S) | No | | | |
| (10) | $C_{13}H_{27}$ | $CH_2CO_2CH_3$ (R) | $CH_3$ (S) | No | | | |
| (11) | $C_{13}H_{27}$ | $CH_2CON(CH_3)_2$ | $CH_3$ (S) | No | | | |
| (12) | $C_{13}H_{27}$ | $CH_2CONH_2$ (R) | H | Yes | TBD | TBD | TBD |
| (13) | $C_{13}H_{27}$ | $CH_2CONH_2$ (R) | β-Ala | Yes | TBD | TBD | TBD |
| (14) | $C_{13}H_{27}$ | $CH_2CONH_2$ (R) | $CH_2CH_2CO_2CH_3$ | Yes | TBD | TBD | TBD |

Fig. 2B

|   | $k_{cat}$ (min$^{-1}$) | $K_M$ (μM) | $k_{cat}/K_M$ (M$^{-1}$s$^{-1}$) |
|---|---|---|---|
| 2 | 36 ± 4 | 130 ± 26 | 4600 ± 1100 |
| 3 | 80 ± 13 | 246 ± 70 | 5400 ± 1800 |
| 4 | 28 ± 15 | 680 ± 470 | 690 ± 600 |

METHODS AND COMPOSITIONS RELATING TO GENOTOXIN COLIBACTIN

CROSS-REFERENCE TO RELATED APPLICATIONS

This application claims benefit under 35 U.S.C. § 119(e) of U.S. Provisional Application No. 62/719,325 filed Aug. 17, 2018, the contents of which are incorporated herein by reference in their entirety.

GOVERNMENT SUPPORT

This invention was made with government support under Grant Nos. R01CA208834 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 13, 2019, is named 002806-093410USPT_SL.txt and is 5,098 bytes in size.

TECHNICAL FIELD

The technology described herein relates to compounds and methods for the measurement of the activity and/or levels of ClbP, a key enzyme involved in the biosynthesis of colibactin.

BACKGROUND

The genotoxin colibactin is produced by commensal and pathogenic strains of bacteria and has been linked to the development of colorectal cancer. In the final stages of colibactin biosynthesis, an inactive precursor (precolibactin) must be cleaved by ClbP to produce colibactin itself. The activity of ClbP has not previously been studied in vitro.

SUMMARY

As described herein, the inventors have, for the first time, characterized the activity of ClbP, including its substrate preferences. This information was used to design the compounds described herein, which function as probes for the activity and/or presence of ClbP. These compounds thereby permit methods of detecting ClbP, the bacteria which produce it, the bacteria which are risk factors for certain diseases described herein, and whether subjects have or are at risk of diseases caused by these bacteria.

In one aspect of any of the embodiments, described herein is a composition comprising a compound of Structure I:

Structure I

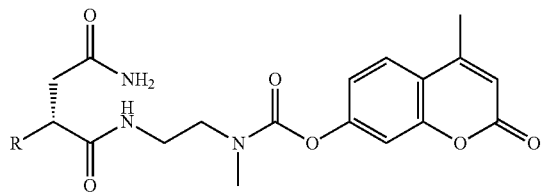

wherein R is alkyl, alkenyl, alkynyl, acyl, aryl, heteroaryl, cyclyl, heterocyclyl, amino, alkylamino, dialkylamino, aminoalkyl, acylamino, hydroxyl, or alkoxy, each of which can be optionally substituted with one, two, three, four or more independently selected substituents.

In some embodiments of any of the aspects, R is a hydrophobic acyl. In some embodiments of any of the aspects, R comprises a carbon chain of at least 4 carbons in length. In some embodiments of any of the aspects, R comprises at least 4 carbon atoms. In some embodiments of any of the aspects, R comprises at least 9 carbon atoms. In some embodiments of any of the aspects, R is selected from: $C_{13}H_{27}$; (4-Ph)-$C_3H_6$, $C_3H_7$, $CH_3$, and (8-$NH_2$)$C_7H_{15}$.

In some embodiments of any of the aspects, R comprises:

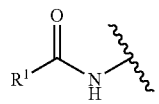

wherein $R^1$ is selected from alkyl, alkenyl, alkynyl, aryl, heteroaryl, cyclyl, heterocyclyl or aminoalkyl, each of which can be optionally substituted with one, two, three or more independently selected substituents. In some embodiments of any of the aspects, $R^1$ is a $C_1$-$C_{18}$alkyl, optionally substituted with one substituent. In some embodiments of any of the aspects, $R^1$ is selected from: $C_{13}H_{27}$; (4-Ph)-$C_3H_6$, $C_3H_7$, $CH_3$, and (8-$NH_2$)$C_7H_{15}$.

In some embodiments of any of the aspects, R is selected from:

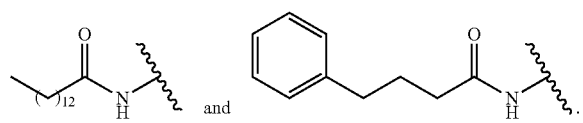

In one aspect of any of the embodiments, described herein is a method of measuring ClbP activity in a sample, the method comprising: contacting the sample with a compound described herein; and measuring fluorescence; wherein increased fluorescence relative to a reference sample indicates an increased level of ClbP activity relative to the reference sample. In some embodiments of any of the aspects, an increased level of ClbP activity indicates an increased level or metabolic activity of pks+ E. coli.

In one aspect of any of the embodiments, described herein is a method of measuring the ClbP inhibitory activity of a candidate agent, the method comprising: contacting a ClbP with the candidate agent and a compound described herein; and measuring the level of fluorescence; wherein decreased fluorescence relative to the level of fluorescence in the absence of the candidate agent indicates the candidate agent has ClbP inhibitory activity. In some embodiments of any of the aspects, contacting a ClbP with the candidate agent comprises contacting a bacterial cell expressing ClbP with the candidate agent.

In one aspect of any of the embodiments, described herein is a method of measuring colibactin or detecting the presence or likelihood of colibactin in a sample, the method comprising: contacting the sample with a compound described herein; and measuring fluorescence; wherein increased fluorescence relative to a reference indicates an increased level of colibactin, the presence of colibactin, or an increased likelihood of colibactin relative to the reference.

In some embodiments of any of the aspects, an increased level of colibactin indicates an increased level or metabolic activity of pks+ E. coli. In some embodiments of any of the aspects, the presence of colibactin indicates the presence of pks+ E. coli. In some embodiments of any of the aspects, an increased likelihood of colibactin indicates an increased likelihood of pks+ E. coli.

In one aspect of any of the embodiments, described herein is a method of diagnosing cancer, or detecting the risk of cancer in a subject, the method comprising: contacting a sample obtained from the subject with a compound described herein; and measuring fluorescence; wherein increased fluorescence relative to a reference indicates increased ClbP activity, the presence of cancer, and/or an increased risk of cancer. In some embodiments of any of the aspects, the cancer is colorectal cancer.

In some embodiments of any of the aspects, the reference is the level of fluorescence in the sample prior to contacting it with the composition described herein. In some embodiments of any of the aspects, the sample comprises bacterial cells or bacterial cell lysates. In some embodiments of any of the aspects, the presence of fluorescence indicates the bacterial cells comprise colibactin biosynthetic machinery/pathways. In some embodiments of any of the aspects, the presence of fluorescence indicates the bacterial cells comprise pks+ E. coli.

BRIEF DESCRIPTION OF THE DRAWINGS

FIGS. 2A-2B demonstrate that ClbP is active on synthetic substrates in vitro. The top graph of FIG. 2A depicts LC-MS detection of the prodrug scaffold ([M+H]+: 343.2597 m/z) released by the hydrolysis of (1) by ClbP in vitro. Reactions were carried out in 50 mM Tris pH 8.0, 200 mM NaCl, 0.1 µM enzyme. 0.02% w/v DDM was added for all reactions involving full-length ClbP (Error bars are SD, n=3). The bottom graph of FIG. 2B depicts kinetic analysis of ClbP acting on synthetic precolibactin-mimic substrate (1). Note that this substrate is insoluble above 200 µM under assay conditions. Rates were calculated by quenching reactions in 1-minute intervals in methanol and quantifying the amount of substrate cleaved by derivatization of the L-alanine product with o-phthaldialdehye (OPA) and fluorescence detection (see Examples) (Error bars are SD, n=3). Substrate is insoluble above 200 µM under assay conditions. All kinetics experiments are averages of 3 independent replicates, reactions were carried out in 50 mM Sodium Phosphate pH 8.0, 200 mM NaCl, 0.02% w/v DDM, 0.1 µM enzyme. The bottom graph of FIG. 2B depicts the approach and substrates sampled in this SAR study. All kinetics experiments are averages of 3 independent replicates, reactions were carried out in 50 mM Sodium Phosphate pH 8.0, 200 mM NaCl, 0.02% w/v DDM, 0.1 µM ClbP-FL (full length) (also referred to herein as ClbP$_{FL}$). All errors are ±SD.

FIG. 3A depicts a schematic of the mechanism of activation of the ClbP fluorogenic probes. FIG. 3B demonstrates (top graph) that fluorogenic probe (16) is activated by ClbP-FL and not ClbP-pep in vitro and shows robust signal in 384-well plate format (Error bars are SD, n=6, 0.1 µM enzyme) and (bottom graph) fluorogenic probe (16) can be activated by whole cells (E. coli BL21) overexpressing ClbP (Error bars are SD, n=6).

FIG. 6A: These compounds are named according to the mass by which they were first identified via mass spectrometry. All of the structures shown here have been confirmed by either total synthesis of these molecules, or isolation from biological sources and characterization by NMR.[2,6,7,10,11] The various candidate precolibactin metabolites, all of which have been isolated from strains of pks+ E. coli missing ClbP, possess structural features that may be present in the final genotoxin. Metabolites containing a pyridone group and larger macrocycles (Precolibactins '816', '796', and '887' above) cannot cyclize upon cleavage by ClbP as shown in FIG. 1, which suggests that they are shunt products from the biosynthetic pathway that accumulate in the absence of ClbP. The colibactin-DNA adduct was proposed by Xue and coworkers based on mass spectrometry experiments with DNA treated in vitro with pks+ E. coli.[12] Wilson and coworkers identified this adduct from eukaryotic cells infected with pks+ E. coli and, after characterizing its structure by NMR using a synthetic colibactin mimic, confirmed its presence in an animal model.[10] The structure of this adduct provides further support for the proposed cyclopropane electrophilic warhead. (FIG. 6B) Possible steps in the colibactin cyclopropane warhead formation. ClbP can process both cyclized and uncyclized substrates, so it is not immediately obvious which of the two pathways presented here predominates in the native colibactin biosynthesis pathway.

(FIG. 9A) Bars represent average amount of substrate consumed across 3 replicates after 5 hours. Concentrations were determined by comparing peak areas of the [M+H]⁺ ions of each substrates to a standard curve generated for each substrate (see methods below. Triangles represent individual replicate values, error bars=1 SD). First series is ClbP$_{FL}$ and second series is ClbP$_{FLS95A}$ (FIG. 9B) Representative EICs for [M+H]⁺ ion masses of substrate 2 and its ClbP$_{FL}$ cleavage product, 20 from a typical reaction at the start of the reaction ("0 h") and after 5 hours at room temperature ("5 h"). 2: 428.3124 m/z; 20: 343.2597 m/z.

(FIG. 12A) Bars represent average EIC peak areas for to the [M+H]⁺ ions of the expected cleavage products: 2: 343.2597 m/z; 7: 344.2437 m/z; 8: 343.2597 m/z; 9: 357.2753 m/z; 10: 300.2539 m/z; 11: 358.2593 m/z; 12: 371.2910 m/z; All substrates were tested in triplicate; triangles show individual replicate values (error bars=1 SD). First series is ClbP$_{FL}$ and second series is ClbP$_{FLS95A}$. (FIGS. 12B-12F) Representative EIC traces (1 replicate each) for masses of substrates and expected cleavage products ([M+H]⁺ and [M+Na]⁺ for products, [M+H]⁺ for substrates) for each of the substrates which showed no cleavage by ClbP$_{FL}$ in vitro (substrates 8-12). All EICs are for reactions quenched after incubation at room temperature for 5 hours. First, third, and fifth series/line on the z-axis are ClbP$_{FL}$ and second, fourth, ans sixth series/lines on the z-axis are ClbP$_{FLS95A}$

DETAILED DESCRIPTION

Figure 1:
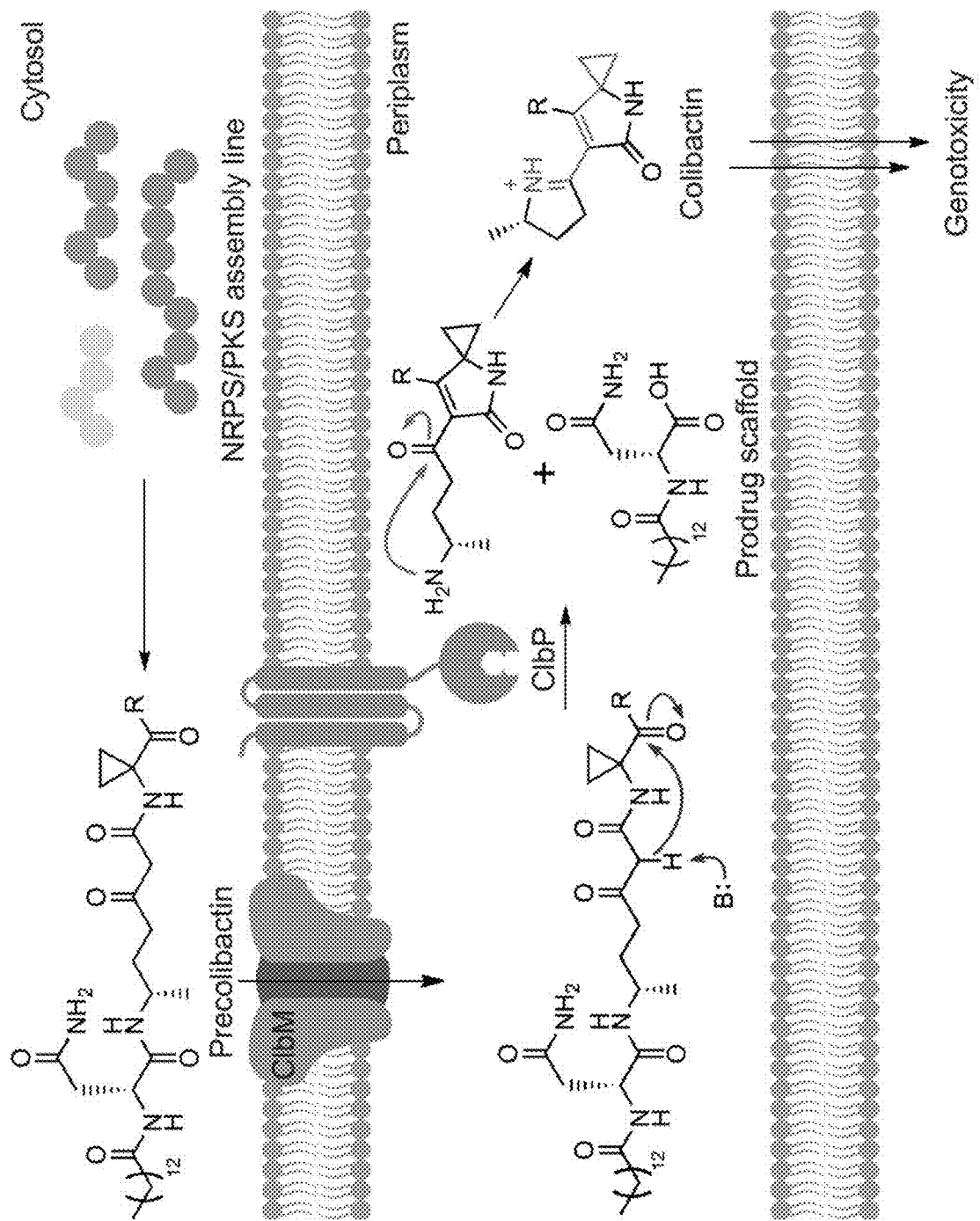
FIG. 1 depicts a diagram of ClbP activation of colibactin. Precolibactin is synthesized by the Clb nonribosmal synthetase-polyketide synthase (NRPS-PKS) assembly line and tailoring enzymes before being cleaved by ClbP in the periplasm. This hydrolytic activation enhances the electrophilicity of the cylcopropane warhead.

As described herein, the inventors have for the first time characterized the substrate preferences and activity of ClbP. These discoveries where used to guide the design of compounds which are probes for ClbP—in the presence of ClbP, the compounds are cleaved into two portions, one of which is fluorescent following cleavage and subsequent non-enzymatic cyclization to release the free fluorophore. Accordingly, in one aspect of any of the embodiments, described herein is a composition comprising a compound of Structure I:

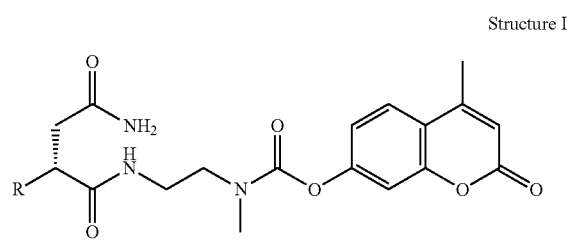

Structure I wherein R is alkyl, alkenyl, alkynyl, acyl, aryl, heteroaryl, cyclyl, heterocyclyl, amino, alkylamino, dialkylamino, aminoalkyl, acylamino, hydroxyl, alkoxy, each of which can be optionally substituted with one, two, three, four or more independently selected substituents.

"Alkyl" refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. "Branched" refers to an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons. In some embodiments, alkyl is a $C_1$-$C_{20}$alkyl, optionally substituted with one, two, three, four or more independently selected substituents. For example, the $C_1$-$C_{20}$alkyl can be substituted at the terminal carbon by one substituent. In some preferred embodiments, alkyl is tridecyl, 1-propyl, 4-phenylprop-1-yl, methyl or 8-aminoheptyl.

"Alkenyl" refers to an alkyl group containing at least one carbon-carbon double bond. The alkenyl group can be optionally substituted with one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

"Alkynyl" refers to an alkyl group containing a carbon-carbon triple bond. The alkynyl group can be optionally substituted with one or more "alkyl group substituents." Exemplary alkynyl groups include ethynyl, propargyl, n-pentynyl, decynyl and dodecynyl. Useful alkynyl groups include the lower alkynyl groups.

"Cycloalkyl" refers to a non-aromatic mono- or multicyclic ring system having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. Examples of cyclyl groups include, without limitation, cyclopropyl, cyclobutyl, cyclopentyl, cyclopentenyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

"Heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

"Aryl" refers to an aromatic carbocyclic radical containing about 6 to about 10 carbon atoms. The aryl group can be optionally substituted with one or more aryl group substituents, which can be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, rylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively.

Exemplary aryl and heteroaryls include, but are not limited to, phenyl, pyridinyl, pyrimidinyl, furanyl, thienyl, imidazolyl, thiazolyl, pyrazolyl, pyridazinyl, pyrazinyl, triazinyl, tetrazolyl, indolyl, benzyl, naphthyl, anthracenyl, azulenyl, fluorenyl, indanyl, indenyl, naphthyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro [2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

The term "hydrophobic acyl group" refers to a R—C (=O)— group, wherein R is an alkyl, aryl, heteroayl, cyclyl, heterocyclyl, aralkyl or other non-polar group.

"Acylamino" refers to an acyl-NH— group, wherein acyl is as previously described.

"Alkoxy" refers to an alkyl-O— group, wherein alkyl is as previously described. Exemplary alkoxy groups include methoxy, ethoxy, n-propoxy, i-propoxy, n-butoxy, and heptoxy.

As used herein, the term "amino" means —$NH_2$. The term "alkylamino" means a nitrogen moiety having one straight or branched unsaturated aliphatic, cyclyl, or heterocyclyl radicals attached to the nitrogen. The term "dialkylamino" means a nitrogen moiety having two straight or branched unsaturated aliphatic, cyclyl, or heterocyclyl radicals attached to the nitrogen. Exemplary dialkylamino groups include ethylmethylamino, dimethylamino, and diethylamino.

The term "aminoalkyl" means an alkyl, alkenyl, and alkynyl as defined above and substituted with one or more substituents independently selected from amino, alkylamino and dialkylamino.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine. A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—CF$_3$), 2,2,2-trifluoroethyl, perfluoroethyl, 2,2,2-trifluoro-1,1-dichloroethyl, and the like).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, CF$_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

As used here in the term "isomer" refers to compounds having the same molecular formula but differing in structure. Isomers which differ only in configuration and/or conformation are referred to as "stereoisomers." The term "isomer" is also used to refer to an enantiomer.

In some embodiments of any of the aspects, R is a hydrophobic acyl.

In some embodiments of any of the aspects, R comprises a carbon chain of at least 4 carbons in length. In some embodiments of any of the aspects, R comprises a carbon chain of at least 5 carbons in length. In some embodiments of any of the aspects, R comprises a carbon chain of at least 6 carbons in length. In some embodiments of any of the aspects, R comprises a carbon chain of at least 7 carbons in length. In some embodiments of any of the aspects, R comprises a carbon chain of at least 8 carbons in length. In some embodiments of any of the aspects, R comprises a carbon chain of at least 9 carbons in length.

In some embodiments of any of the aspects, R comprises at least 4 carbons atoms. In some embodiments of any of the aspects, R comprises at least 5 carbons atoms. In some embodiments of any of the aspects, R comprises at least 6 carbons atoms. In some embodiments of any of the aspects, R comprises at least 7 carbons atoms. In some embodiments of any of the aspects, R comprises at least 98 carbons atoms. In some embodiments of any of the aspects, R comprises at least 9 carbons atoms. In some embodiments of any of the aspects, R comprises at least 10 carbons atoms. In some embodiments of any of the aspects, R comprises at least 11 carbons atoms. In some embodiments of any of the aspects, R comprises at least 12 carbons atoms.

In some embodiments of any of the aspects, R comprises a carbon chain of 4 carbons in length. In some embodiments of any of the aspects, R comprises a carbon chain of 5 carbons in length. In some embodiments of any of the aspects, R comprises a carbon chain of 6 carbons in length. In some embodiments of any of the aspects, R comprises a carbon chain of 7 carbons in length. In some embodiments of any of the aspects, R comprises a carbon chain of 8 carbons in length. In some embodiments of any of the aspects, R comprises a carbon chain of 9 carbons in length.

In some embodiments of any of the aspects, R comprises 4 carbons atoms. In some embodiments of any of the aspects, R comprises 5 carbons atoms. In some embodiments of any of the aspects, R comprises 6 carbons atoms. In some embodiments of any of the aspects, R comprises 7 carbons atoms. In some embodiments of any of the aspects, R comprises 98 carbons atoms. In some embodiments of any of the aspects, R comprises 9 carbons atoms. In some embodiments of any of the aspects, R comprises 10 carbons atoms. In some embodiments of any of the aspects, R comprises 11 carbons atoms. In some embodiments of any of the aspects, R comprises 12 carbons atoms.

In some embodiments of any of the aspects, R is selected from $C_{13}H_{27}$; (4-Ph)-$C_3H_6$, $C_3H_7$, $CH_3$, and/or (8-NH$_2$) $C_7H_{15}$.

In some embodiments of any of the aspects, R comprises:

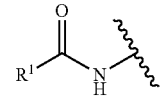

wherein $R^1$ is selected from alkyl, alkenyl, alkynyl, aryl, heteroaryl, cyclyl, heterocyclyl or aminoalkyl, each of which can be optionally substituted with one, two, three or more independently selected substituents. In some embodiments of any of the aspects, $R^1$ is a $C_1$-$C_{18}$alkyl, optionally substituted with one substituent. In some embodiments of any of the aspects, $R^1$ is a $C_1$-$C_{18}$alkyl. In some embodiments of any of the aspects, $R^1$ is selected from: $C_{13}H_{27}$; (4-Ph)-$C_3H_6$, $C_3H_7$, $CH_3$, and (8-NH$_2$)$C_7H_{15}$.

In some embodiments of any of the aspects, R is

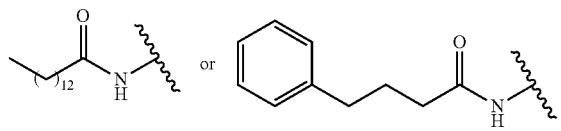

The compositions described herein function as fluorogenic probes for ClbP activity. That is, ClbP cleaves the compounds described herein into two portions, one of which is fluorescent when separated from the other portion following non-enzymatic cyclization and release of the free fluorophore.

Accordingly, in one aspect of any of the embodiments, provided herein is a method of measuring ClbP activity in a sample, the method comprising: contacting the sample with a compound described herein and measuring fluorescence. Increased fluorescence relative to a reference sample/level indicates an increased level of ClbP activity in the sample relative to the reference sample/level.

As used herein "ClbP" or "colibactin P" refers to a membrane bound periplasmic peptidase that cleaves an N-acyl-D-asparagine motif (the 'prodrug scaffold') from the N-terminus of precolibactin to liberate the active colibactin (FIG. 1). The sequences of ClbP are known in the art, e.g., the polypeptide sequence is available in the Uniprot database as accession number Q0P7K6 (SEQ ID NO: 1).

The term "sample" or "test sample" as used herein denotes a sample taken or isolated from a biological organism, e.g., a blood or plasma sample from a subject or a bacterial culture or cell lysate. In some embodiments of any of the aspects, the present invention encompasses several examples of a biological sample. In some embodiments of any of the aspects, the biological sample is cells, cell lysate, or tissue, or peripheral blood, or bodily fluid. Exemplary biological samples include, but are not limited to, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples.

In some embodiments of any of the aspects, the sample comprises bacterial cells or bacterial cell lysates. In some embodiments of any of the aspects, the sample is a sample obtained from a subject, e.g, a human subject. In some embodiments of any of the aspects, the sample is a sample obtained from a bacterial culture. In some embodiments of any of the aspects, a test sample can comprise cells from a subject.

The test sample can be obtained by removing a sample from a subject or culture, but can also be accomplished by using a previously isolated sample (e.g. isolated at a prior timepoint and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments of any of the aspects, the methods, assays, and systems described herein can further comprise a step of obtaining or having obtained a test sample from a subject, culture, or other source. In some embodiments of any of the aspects, the subject can be a human subject.

When the fluorescent portion of the compounds described herein is released, e.g., by cleavage of the compound by ClbP, and is exposed to light of the proper wavelength, its presence can then be detected due to fluorescence. In some embodiments of any of the aspects, the compounds herein have a Abs/Em=364/458 nm. In some embodiments of any of the aspects, the compounds herein have a Abs/Em of about 360/440 nm. In some embodiments of any of the aspects, the compounds herein have a Abs/Em of about 360 (with a 40 nM bandwidth)/440 nm (with a 20 nM bandwidth)

Systems and devices for the measurement of fluorescence are well known in the art. Fluoresence measurement requires a light source that emits light comprising the appropriate absorption or excitation wavelength. The absorption or excitation wavelength of the compounds described herein is 364 nm. In some embodiments of any of the aspects, the light source emits light comprising, consisting essentially of, or consisting of a wavelength of 364 nm. In some embodiments of any of the aspects, the light source emits light comprising, consisting essentially of, or consisting of a wavelength of 360-370 nm. In some embodiments of any of the aspects, the light source emits light comprising, consisting essentially of, or consisting of a wavelength of 350-380 nm. In some embodiments of any of the aspects, the light source emits light comprising, consisting essentially of, or consisting of a wavelength of 340-390 nm. In some embodiments of any of the aspects, the light source emits light comprising, consisting essentially of, or consisting of a wavelength of 330-400 nm.

The light contacts the sample, which excites electrons in certain materials within the sample, also known as fluorophores, and causes the materials to emit light (light emission) in the form of fluorescence.

The system or device for measurement of fluorescence then detects the emitted light. In some embodiments, the system or device can comprise a filter or monochromator so that only light of desired wavelengths reaches the detector of the system or device. In some embodiments of any of the aspects, the system or device is configured to detect light comprising, consisting essentially of, or consisting of a wavelength of 458 nm. In some embodiments of any of the aspects, the system or device is configured to detect light comprising, consisting essentially of, or consisting of a wavelength of 455-460 nm. In some embodiments of any of the aspects, the system or device is configured to detect light comprising, consisting essentially of, or consisting of a wavelength of 445-470 nm. In some embodiments of any of the aspects, the system or device is configured to detect light comprising, consisting essentially of, or consisting of a wavelength of 435-480 nm. In some embodiments of any of the aspects, the system or device is configured to detect light comprising, consisting essentially of, or consisting of a wavelength of 455-490 nm.

Suitable systems and devices are commercially available and can include, e.g., the 20/30 PV™ Microspectrometer or 508 PV™ Microscope Spectrometer from CRAIC (San Dimas, Calif.), the Duetta™, FluoroMax™, Fluorolog™, QuantaMaster 8000™, DeltaFlex™, DeltaPro, or Nanolog™ from Horiba (Irvine, Calif.), or the SP8 Lightning™, SP8 Falcon™, SP8 Dive™, TCS SPE™, HCS A™, or TCS SP8 X™ from Leica (Buffalo Grove, Ill.).

In some embodiments of any of the aspects, the reference sample or level is the sample or level of the sample itself prior to being contacted with a compound described herein. In some embodiments of any of the aspects, the reference sample or level is the sample or level of compound described herein prior to being contacted with the sample.

In some embodiments of any of the aspects, the reference can be a level obtained from a population of bacteria which are not pks+, or do not express ClbP, or do not produce colibactin. In some embodiments of any of the aspects, the reference can be the level obtained from the same population or source of bacteria at an earlier point in time, e.g., the methods described herein can be used to determine if ClbP activity is changing over time.

In some embodiments of any of the aspects, the reference can also be a level obtained from a control sample, a pooled sample of control individuals or a numeric value or range of values based on the same.

In some embodiments of any of the aspects, the reference can be the level in a population of subjects who do not have or are not diagnosed as having, and/or do not exhibit signs or symptoms of an infection of pks+ E. coli. In some embodiments of any of the aspects, the reference can be the level in a sample obtained from the same subject at an earlier point in time, e.g., the methods described herein can be used to determine if the level of pks+ E. coli or colibactin in a subject is changing over time.

In some embodiments of any of the aspects, the reference level/sample has the same amount and/or concentration of the compound as the sample. In some embodiments of any of the aspects, the same amount and/or concentration of the compound is added to the sample and the reference sample. In some embodiments of any of the aspects, the reference level/sample has an amount and/or concentration of the compound with a known mathematical relationship to the amount and/or concentration of the compound in the sample (e.g., twice as much, or half as much). In some embodiments of any of the aspects, the amount and/or concentration of the compound added to the sample and the reference sample have a known mathematical relationship.

A level which is less than a reference level can be a level which is less by at least about 10%, at least about 20%, at least about 50%, at least about 60%, at least about 80%, at least about 90%, or less relative to the reference level. In some embodiments of any of the aspects, a level which is less than a reference level can be a level which is statistically significantly less than the reference level.

A level which is more than a reference level can be a level which is greater by at least about 10%, at least about 20%, at least about 50%, at least about 60%, at least about 80%, at least about 90%, at least about 100%, at least about 200%, at least about 300%, at least about 500% or more than the reference level. In some embodiments of any of the aspects, a level which is more than a reference level can be a level which is statistically significantly greater than the reference level.

In the final stages of colibactin biosynthesis, the inactive precursor (precolibactin) is activated via proteolytic cleavage by ClbP. Thus, the presence of ClbP activity indicates the presence of a cell or cells that can produce colibactin or is producing colibactin. Accordingly, in one aspect of any of the embodiments, described herein is a method of measuring colibactin or detecting the presence or likelihood of colibactin in a sample, the method comprising contacting the sample with a compound described herein and measuring fluorescence; wherein increased fluorescence relative to a reference indicates an increased level of colibactin, the presence of colibactin, and/or an increased likelihood of colibactin relative to the reference.

The suite of genes necessary for colibactin biosynthesis (including clbP) are located on the biosynthetic gene cluster known as the pks island. Pks+ E. coli induce DNA double-strand breaks (DSBs) in eukaryotic cells, and mono-colonization with pks+ E. coli increases tumor load in a genetically susceptible mouse model colorectcal cancer. Pks+ E. coli are also found more frequently in patients with colorectal cancer than in healthy controls. Accordingly, an increased level of ClbP as detected in accordance with the methods described herein indicates an increased level or metabolic activity of $pks^+$ E. coli. In some embodiments of any of the aspects, detection of ClbP activity in accordance with the methods described herein indicates the presence of $pks^+$ E. coli. In some embodiments of any of the aspects, an increased level of colibactin indicates an increased level or metabolic activity of $pks^+$ E. coli. In some embodiments of any of the aspects, the presence of colibactin indicates the presence of $pks^+$ E. coli. In some embodiments of any of the aspects, an increased likelihood of colibactin indicates an increased likelihood of $pks^+$ E. coli.

In some embodiments of any of the aspects, an increased level or metabolic activity of $pks^+$ E. coli indicates an increased level of colibactin. In some embodiments of any of the aspects, he presence of $pks^+$ E. coli indicates the presence of colibactin indicates. In some embodiments of any of the aspects, an increased likelihood of $pks^+$ E. coli indicates an increased likelihood of colibactin.

As noted above, the genotoxin colibactin is produced by commensal and pathogenic strains of bacteria and has been linked to the development of colorectal cancer. Accordingly, in one aspect of any of the embodiments, described herein is a method of diagnosing or detecting the risk of cancer, or detecting the risk of cancer in a subject, the method comprising contacting a sample obtained from the subject with a compound described herein and measuring fluorescence; wherein increased fluorescence relative to a reference indicates increased ClbP activity, the risk or presence of cancer, and/or an increased risk of cancer. In some embodiments of any of the aspects, the cancer is colorectal cancer.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord. A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably. A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome The ability to measure ClbP activity further permits methods of identifying ClbP inhibitory agents and/or of measuring the ClbP inhibitory activity of a candidate agent. Accordingly, in one aspect of any of the embodiments, described herein is a method of measuring the ClbP inhibitory activity of a candidate agent, the method comprising contacting a ClbP with the candidate agent and a compound described herien and measuring the level of fluorescence; wherein decreased fluorescence relative to the level of fluorescence in the absence of the candidate agent indicates the candidate agent has ClbP inhibitory activity. In one aspect of any of the embodiments, described herein is a method of identifying a candidate agent as a ClbP inhibitory agent, the method comprising contacting a ClbP with the candidate agent and a compound described herien and measuring the level of fluorescence; wherein decreased fluorescence relative to the level of fluorescence in the absence of the candidate agent indicates the candidate agent is a ClbP inhibitory agent.

As used herein, the term "inhibitor" refers to an agent which can decrease the expression and/or activity of the target (e.g. ClbP polypeptide or ClbP mRNA), e.g. by at least 10% or more, e.g. by 10% or more, 50% or more, 70% or more, 80% or more, 90% or more, 95% or more, or 98% or more.

As used herein, the terms "candidate compound" or "candidate agent" refer to a compound or agent and/or compositions thereof that are to be screened for their ability to modulate ClbP levels and/or activity. Candidate compounds and agents can be screened for their ability to modulate ClbP levels and/or activity in vitro. The modulation of ClbP can also be monitored in vivo.

As used herein, the terms "compound" or "agent" are used interchangeably and refer to molecules and/or compositions. The compounds/agents include, but are not limited to, chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies and intrabodies, or fragments thereof.

Generally, compounds can be tested at any concentration that can modulate expression or protein activity relative to a control over an appropriate time period. In some embodiments, compounds are tested at concentration in the range of about 0.1 nM to about 1000 mM. In one embodiment, the compound is tested in the range of about 0.1 µM to about 20 µM, about 0.1 µM to about 10 µM, or about 0.1 µM to about 5 µM. In one embodiment, compounds are tested at 1 µM.

Depending upon the particular embodiment being practiced, the test compounds can be provided free in solution, or may be attached to a carrier, or a solid support, e.g., beads.

A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

Candidate agents can be produced recombinantly using methods well known to those of skill in the art (see Sambrook et al., Molecular Cloning: A Laboratory Manual (2 ed.), Cold Spring Harbor Laboratory Press, Cold Spring Harbor, N.Y., USA (1989)). Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule (Woburn, Mass.), Panvera (Madison, Wis.), Ryan Scientific (Mt. Pleasant, S.C.), and Enzo Life Sciences (Plymouth Meeting, Pa.). These libraries can be screened for ability to modulate ClbP using, e.g. methods described herein.

Measurement of ClbP inhibitory activity can be conducted ex vivo, in vitro, or in vivo. In some embodiments of any of the aspects, contacting a ClbP with a candidate agent comprises contacting a bacterial cell expressing ClbP with the candidate agent, e.g., an $E.$ $coli$ or $pks^+$ $E.$ $coli$ cell.

As described herein, level or activity of ClbP can be increased in subjects with $pks^+$ $E.$ $coli$ or cancer. In some embodiments of any of the aspects, the level of ClbP can be increased in subjects with $pks^+$ $E.$ $coli$ or cancer. Accordingly, in one aspect of any of the embodiments, described herein is a method of treating $pks^+$ $E.$ $coli$ or cancer in a subject in need thereof, the method comprising administering a treatment to a subject determined to have a level of ClbP that is increased relative to a reference. In one aspect of any of the embodiments, described herein is a method of treating $pks^+$ $E.$ $coli$ or cancer in a subject in need thereof, the method comprising a) determining the level of ClbP in a sample obtained from a subject and b) administering a treatment to the subject if the level of ClbP is increased relative to a reference.

In one aspect of any of the embodiments, described herein is a method of treating $pks^+$ $E.$ $coli$ or cancer in a subject in need thereof, the method comprising a) determining if the subject has an increased level of ClbP and b) administering a treatment to the subject if the level of ClbP is increased relative to a reference. In some embodiments of any of the aspects, the step of determining if the subject has an increased level of ClbP can comprise i) obtaining or having obtained a sample from the subject and ii) performing or having performed an assay on the sample obtained from the subject to determine/measure the level of ClbP in the subject. In some embodiments of any of the aspects, the step of determining if the subject has an increased level of ClbP can comprise performing or having performed an assay on a sample obtained from the subject to determine/measure the level of ClbP in the subject. In some embodiments of any of the aspects, the step of determining if the subject has an increased level of ClbP can comprise ordering or requesting an assay on a sample obtained from the subject to determine/measure the level of ClbP in the subject. In some embodiments of any of the aspects, the step of determining if the subject has an increased level of ClbP can comprise receiving the results of an assay on a sample obtained from the subject to determine/measure the level of ClbP in the subject. In some embodiments of any of the aspects, the step of determining if the subject has an increased level of ClbP can comprise receiving a report, results, or other means of identifying the subject as a subject with an increased level of ClbP.

In one aspect of any of the embodiments, described herein is a method of treating $pks^+$ $E.$ $coli$ infection or cancer in a subject in need thereof, the method comprising a) determining if the subject has an increased level of ClbP and b) instructing or directing that the subject be administered a treatment if the level of ClbP is increased relative to a reference. In some embodiments of any of the aspects, the step of determining if the subject has an increased level of ClbP can comprise i) obtaining or having obtained a sample from the subject and ii) performing or having performed an assay on the sample obtained from the subject to determine/measure the level of ClbP in the subject. In some embodiments of any of the aspects, the step of determining if the subject has an increased level of ClbP can comprise performing or having performed an assay on a sample obtained from the subject to determine/measure the level of ClbP in the subject. In some embodiments of any of the aspects, the step of determining if the subject has an increased level of ClbP can comprise ordering or requesting an assay on a sample obtained from the subject to determine/measure the level of ClbP in the subject. In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

In one aspect of any of the embodiments, described herein is a method of determining if a subject has $pks^+$ $E.$ $coli$ infection or cancer or is in need of treatment for $pks^+$ $E.$ $coli$ infection or cancer, the method comprising determining the level of ClbP in a sample obtained from the subject, wherein a level of ClbP which is increased relative to a reference indicates the subject has $pks^+$ $E.$ $coli$ infection or cancer or is in need of treatment for $pks^+$ $E.$ $coli$ infection or cancer.

Treatments for $pks^+$ $E.$ $coli$ infections or cancer are known in the art, and include, e.g., chemotherapeutics or antibiotics. Therapeutic agents for conditions described herein are well-known in the art and can readily be identified by one of ordinary skill by consulting, e.g., a current edition of the FDA's Orange Book (Approved Drug Products with Therapeutic Equivalence Evaluations). One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In one aspect of any of the embodiments, described herein is a composition, kit, or combination comprising at least one compound described herein and, optionally, a pharmaceutically acceptable carrier. In some embodiments of any of the aspects, the kit can further comprise, e.g., a reference sample, a solution or formulation of ClbP as a control, or a reference sample comprising, e.g., pks+ *E. coli*.

A kit is an assemblage of materials or components, including at least one of the compounds described herein. The exact nature of the components configured in the kit depends on its intended purpose. In some embodiments of any of the aspects, the kit is configured particularly for human subjects. In further embodiments, the kit is configured for veterinary applications, e.g., diagnosing subjects such as, but not limited to, farm animals, domestic animals, and laboratory animals.

In some embodiments of any of the aspects, a kit includes instructions for use. "Instructions for use" typically include a tangible expression describing the technique to be employed in using the components of the kit to affect a desired outcome in a subject. Still in accordance with the present invention, "instructions for use" may include a tangible expression describing the preparation of a chimeric molecule and/or at least one method parameter, such as assay requirements instructions, and the like, typically for an intended purpose. Optionally, the kit also contains other useful components, such as, measuring tools, diluents, buffers, carriers, syringes or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging may also preferably provide an environment that protects from light, humidity, and oxygen. As used herein, the term "package" refers to a suitable solid matrix or material such as glass, plastic, paper, foil, polyester (such as polyethylene terephthalate, or Mylar) and the like, capable of holding the individual kit components. Thus, for example, a package can be a glass vial used to contain suitable quantities of a composition containing a volume of a chimeric molecule described herein. The packaging material generally has an external label which indicates the contents and/or purpose of the kit and/or its components.

Acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the compound as described herein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99% , or more. As used herein, "reduction" or "inhibition" does not encompass a complete inhibition or reduction as compared to a reference level. "Complete inhibition" is a 100% inhibition as compared to a reference level.

The terms "increased", "increase", "enhance", or "activate" are all used herein to mean an increase by a staticially significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g., infection or cancer. A subject can be male or female.

A subject can be one who has been previously diagnosed with or identified as suffering from or having a condition in need of treatment (e.g. infection or cancer) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. ClbP enzymatic activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, the methods described herein relate to measuring, detecting, or determining the level of fluoresence. As used herein, the term "detecting" or "measuring" refers to observing a signal from a compound described herein, or portions thereof. In some embodiments of any of the aspects, measuring can be a quantitative observation.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A composition comprising a compound of Structure I:

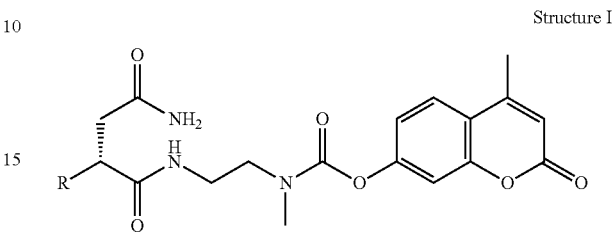

Structure I wherein R is alkyl, alkenyl, alkynyl, acyl, aryl, heteroaryl, cyclyl, heterocyclyl, amino, alkylamino, dialkylamino, aminoalkyl, acylamino, hydroxyl, or alkoxy, each of which can be optionally substituted with one, two, three, four or more independently selected substituents 2. The composition of paragraph 1, wherein R is a hydrophobic acyl.
3. The composition of any of paragraphs 1-2, wherein R comprises a carbon chain of at least 4 carbons in length.
4. The composition of any of paragraphs 1-3, wherein R comprises at least 4 carbon atoms.
5. The composition of any of paragraphs 1-4, wherein R comprises at least 9 carbon atoms.
6. The composition of any of paragraphs 1-5, wherein R is selected from:
   $C_{13}H_{27}$; (4-Ph)-$C_3H_6$, $C_3H_7$, $CH_3$, and (8-$NH_2$)$C_7H_{15}$.
7. The composition of any of paragraphs 1-6, wherein R comprises:

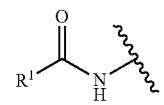

wherein $R^1$ is selected from alkyl, alkenyl, alkynyl, aryl, heteroaryl, cyclyl, heterocyclyl or aminoalkyl, each of which can be optionally substituted with one, two, three or more independently selected substituents.

8. The composition of paragraph 7, wherein $R^1$ is a $C_1$-$C_{18}$alkyl, optionally substituted with one substituent.
9. The composition of paragraph 7, wherein $R^1$ is selected from:
   $C_{13}H_{27}$; (4-Ph)-$C_3H_6$, $C_3H_7$, $CH_3$, and (8-$NH_2$)$C_7H_{15}$.
10. The composition of paragraph 7, wherein R is selected from:

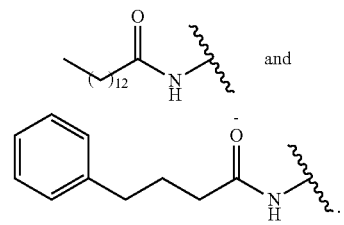

11. A method of measuring ClbP activity in a sample, the method comprising:
   contacting the sample with a compound of any of paragraphs 1-10; and
   measuring fluorescence;
   wherein increased fluorescence relative to a reference sample indicates an increased level of ClbP activity relative to the reference sample.
12. The method of paragraph 11, wherein an increased level of ClbP activity indicates an increased level or metabolic activity of pks$^+$ E. coli.
13. A method of measuring the ClbP inhibitory activity of a candidate agent, the method comprising:
   contacting a ClbP with the candidate agent and a compound of any of paragraphs 1-10; and
   measuring the level of fluorescence;
   wherein decreased fluorescence relative to the level of fluorescence in the absence of the candidate agent indicates the candidate agent has ClbP inhibitory activity.
14. The method of paragraph 13, wherein contacting a ClbP with the candidate agent comprises contacting a bacterial cell expressing ClbP with the candidate agent.
15. A method of measuring colibactin or detecting the presence or likelihood of colibactin in a sample, the method comprising:
   contacting the sample with a compound of any of paragraphs 1-10; and
   measuring fluorescence;
   wherein increased fluorescence relative to a reference indicates an increased level of colibactin, the presence of colibactin, or an increased likelihood of colibactin relative to the reference.
16. The method of paragraph 15, wherein an increased level of colibactin indicates an increased level or metabolic activity of pks$^+$ E. coli.
17. The method of paragraph 15, wherein the presence of colibactin indicates the presence of pks$^+$ E. coli.
18. The method of paragraph 15, wherein an increased likelihood of colibactin indicates an increased likelihood of pks$^+$ E. coli.
19. A method of diagnosing cancer, or detecting the risk of cancer in a subject, the method comprising:
   contacting a sample obtained from the subject with a compound of any of paragraphs 1-10; and
   measuring fluorescence;
   wherein increased fluorescence relative to a reference indicates increased ClbP activity, the presence of cancer, and/or an increased risk of cancer.
20. The method of paragraph 19, wherein the cancer is colorectal cancer.
21. The method of any of paragraphs 11-20, wherein the reference is the level of fluorescence in the sample prior to contacting it with the composition of paragraphs 1-10.
22. The method of any of paragraphs 11-21, wherein the sample comprises bacterial cells or bacterial cell lysates.
23. The method of paragraph 22, wherein the presence of fluorescence indicates the bacterial cells comprise colibactin biosynthetic machinery/pathways.
24. The method of paragraph 22, wherein the presence of fluorescence indicates the bacterial cells comprise pks$^+$ E. coli.

EXAMPLES

Example 1

Characterization of the Peptidase ClbP Permits Development of a Fluorogenic Assay and Detection of Genotoxin-Producing Gut Bacteria The genotoxin colibactin is produced by commensal and pathogenic strains of bacteria and has been linked to the development of colorectal cancer. In the final stages of colibactin biosynthesis, an inactive precursor (precolibactin) must be activated via proteolytic cleavage by ClbP, an unusual inner-membrane bound periplasmic peptidase. This enzyme presents a unique opportunity to monitor and modulate colibactin biosynthesis, but its activity has not yet been studied in vitro. Described herein is the in vitro biochemical characterization of the catalytically active form of this enzyme. The substrate preferences of ClbP are elucidated and used to develop a fluorogenic probe for ClbP activity. This probe is hydrolyzed by ClbP both in vitro and in whole cells and can serve as a sensitive measurement of for ClbP activity, as well as a phenotypic test for the presence of colibactin biosynthetic machinery in bacterial isolates.

The community of trillions of microorganisms living on and in the human body, known as the human microbiota, has been implicated in a wide variety of diseases, including heart disease, diabetes, and cancer. In the case of colorectal cancer (CRC), several specific organisms have been identified as possible risk factors for this disease, including both commensal and pathogenic E. coli. These strains possess a biosynthetic gene cluster known as the pks island, which encodes a hybrid polyketide synthase-nonribosomal peptide synthase (PKS-NRPS) assembly line that synthesizes the small molecule genotoxin colibactin. Numerous studies have shown that pks+ E. coli induce DNA double-strand breaks (DSBs) in eukaryotic cells, and that mono-colonization with pks+ E. coli increases tumor load in a genetically susceptible mouse model of CRC in an inflammation-dependent fashion. Clinical studies have also shown that pks+ E. coli are found more frequently in patients with CRC than in healthy controls. Despite its unusually strong links to human disease, colibactin has never been isolated or structurally characterized, limiting our understanding of its mechanism of action.

In order to study this elusive molecule, several groups have focused on identifying its biosynthetic precursors using a combination of metabolomics with mutant pks strains, as well as in vitro characterization of the assembly line enzymes. A key early discovery from these studies was that the initial product of the PKS-NRPS assembly line is a larger precursor termed 'precolibactin', which is not genotoxic. ClbP, a membrane bound periplasmic peptidase, must cleave off an N-acyl-D-asparagine motif (the 'prodrug scaffold') from the N-terminus of precolibactin to liberate the active genotoxin (FIG. 1). Thus, deletion of clbP from pks+ E. coli strains can cause the build up of a variety inactive precursors and shunt metabolites ('candidate precolibactins'), several of which have been isolated and characterized. These efforts revealed that colibactin contains a cyclopropane ring which is activated for DNA alkylation during the ClbP-dependent prodrug cleavage. This step reveals a primary amine, which can cyclize onto a nearby ketone to produce a cyclic iminium ion. Conjugation of this species with the cyclopropane greatly enhances its electrophilicity. It has been shown that synthetic colibactin mimics can only react with DNA in vitro when this electrophilic core is intact. This model of colibactin reactivity has also been supported by the recent isolation of a DNA adduct from HeLa cells exposed to pks+ E. coli. ClbP is therefore an ideal target to study the activity of colibactin-producing strains at the critical activation step, and to develop inhibitors to modulate this activation.

ClbP belongs to a small subfamily of largely uncharacterized serine peptidases that share homology to the β-lactamase AmpC. Two of ClbP's closest relatives, ZmaM and XcnG, belong to the biosynthetic gene clusters for zwittermicin and xenocoumacin, respectively. These two homologues perform analogous functions in these pathways, processing substrates that also contain an N-acyl-D-asparagine motif. All three proteins share a similar topology, with an N-terminal signal sequence, a soluble peptidase domain, and three C-terminal trans-membrane helices that anchor the enzyme in the inner membrane. ClbP possesses two conserved catalytic motifs that are typical of the S12 family, $^{95}$SxxK and $^{186}$Yx(S/N), where S95 acts as the nucleophile that attacks the scissile amide bond. Mutational studies have confirmed that S95, K98, and Y186 are all essential for genotoxicity. Curiously, all three transmembrane helices of ClbP are also essential for genotoxicity, despite the fact that only a single helix is required for proper localization and membrane association and there are no predicted catalytic residues in this region. Prior studies have shown that several isolated candidate precolibactins and synthetic substrates containing the 'prodrug motif' can be processed by ClbP when fed to whole cells overexpressing the full-length enzyme, but not by cells expressing the S95A mutant or the isolated peptidase domain (ClbP$_{pep}$) (Healy, JACS 2016). Bonnet and coworkers used a crystal structure of the isolated peptidase domain (ClbP$_{pep}$) and an in silico screening strategy to identify two putative boronic acid inhibitors of ClbP. These molecules abrogate the genotoxic effects of pks+ E. coli on HeLa cells at millimolar concentrations, but their ability to inhibit the catalytic activity of ClbP was never established. This question underscores the need for a more detailed in vitro characterization of ClbP's enzymatic activity.

We cloned and overexpressed full-length ClbP (ClbP$_{FL}$) as well as the full length, inactive mutant (ClbP$_{FL}$-S95A) with a C-terminal histidine tag in E. coli BL21. We were able to purify active enzyme by isolating the cell membranes and solubilizing them in a DDM buffer. ClbP$_{FL}$ cleaves a precolibactin-mimic substrate (1) (see FIG. 2B for compound structures indicated by Arabic numerals in parantheses) rapidly in vitro, while ClbP$_{FL}$-S95A shows no cleavage activity by LC-MS.

Figure 2A:
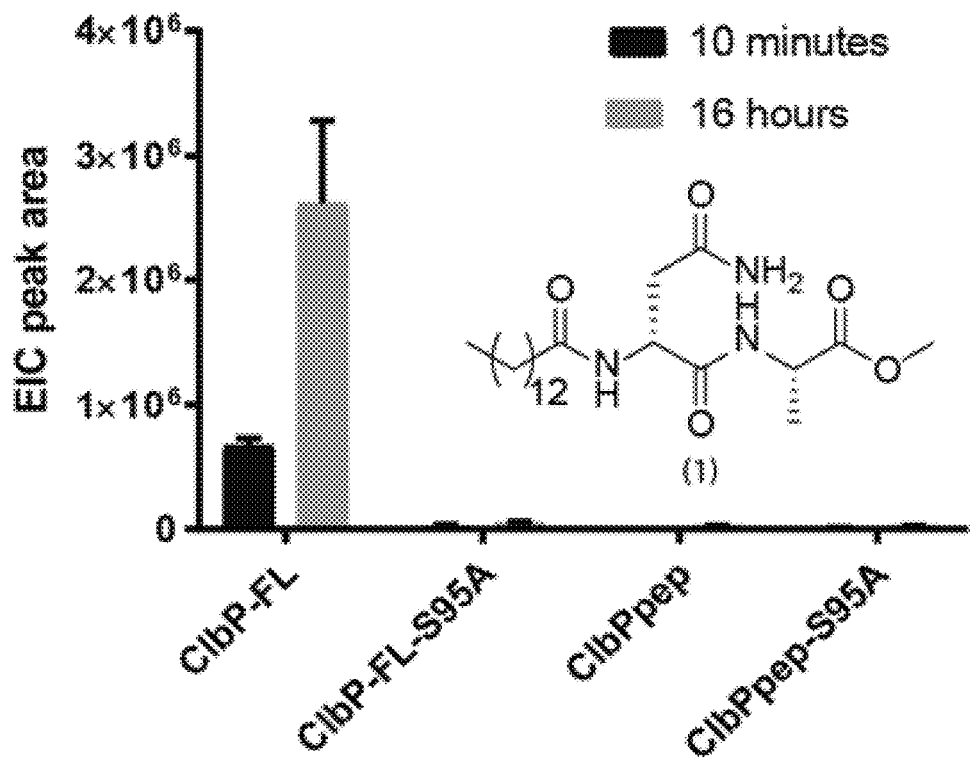
Figure 2A:
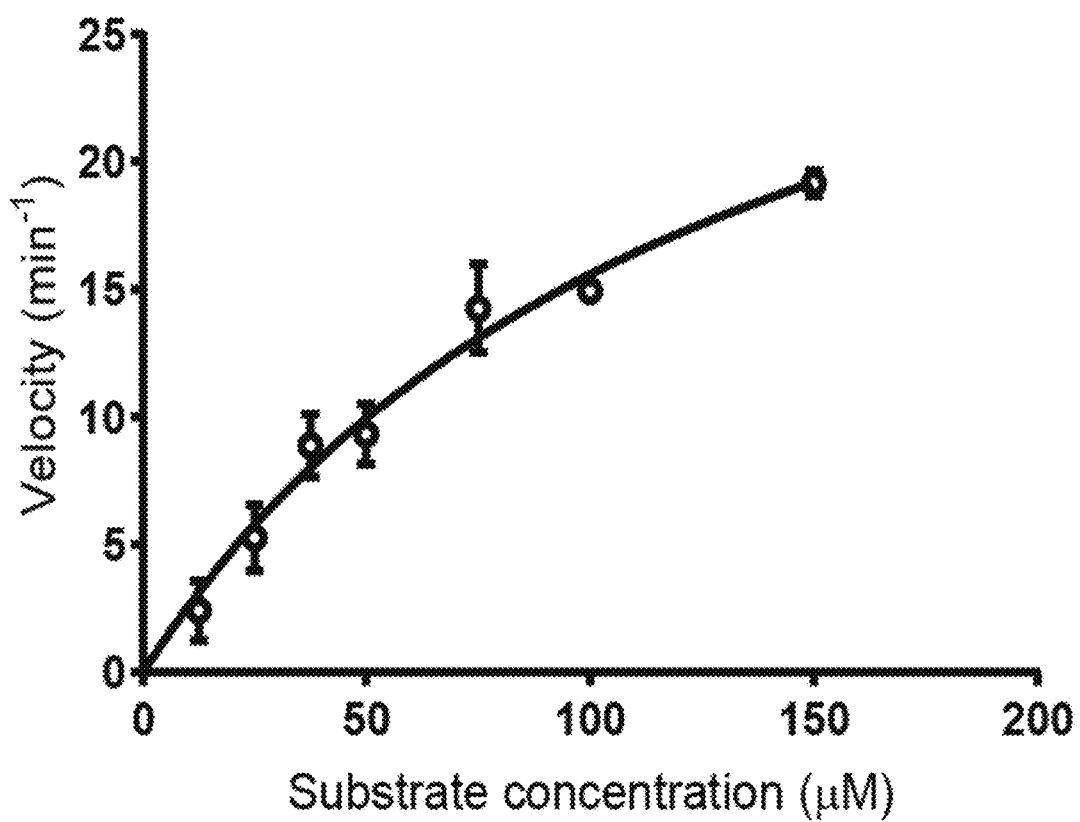

To determine the key features for substrate recognition by full-length ClbP, we undertook a structure-activity-relationship (SAR) focusing on three key regions of the substrate. We first varied the acyl substituent. It is known that the initiating NRPS ClbN can load a variety of acyl-CoA substrates, and ClbP can accept substrates containing shorter chain lengths in vivo (Brotherton JACS 2013). We synthesized a series of precolibactin mimics which varied in acyl chain length, polarity, and steric bulk (FIG. 2B, compounds (2)-(5)). LC-MS assays confirmed that ClbP hydrolyzed all of these substrates at the expected peptide linkage. Using a higher-throughput fluorescence derivatization assay, we determined kinetic parameters for several of these substrates (FIG. 2B). The higher k$_{cat}$ of more hydrophobic, long-chain substrates indicates that this may be an important recognition feature. If substrate binding requires interaction with the hydrophobic transmembrane helices, this could also explain their necessity for genotoxicity.

Having established the flexibility of ClbP with regard to the acyl chain of its substrate, we next explored varying the D-Asn side chain. We tested the reactivity of ClbP$_{FL}$ toward substrates bearing alternative amino acids at this position including L-Asn (7), D-Gln (8), and D-Ala (9). No cleavage products were detected by LC-MS for any of these substrates (SI). The substrate bearing D-Asp (6) was cleaved in low amounts by ClbP$_{FL}$ (~100 fold less than (1)). However, when this substrate was further derivatized to the D-Asp methyl ester (10) or the D-Asn dimethylamide (11), cleavage was abolished. These results, in addition to the observation that D-Asn is conserved in the substrates of all characterized ClbP homologues, indicate that this amino acid is a key recognition feature, and that the size and stereochemistry of this side chain are the most important elements. This high specificity for a D-amino acid cleavage site is not unique to ClbP and may in fact be a common feature of many prodrug activation mechanisms. Qian and coworkers recently reported the identification of thousands of biosynthetic gene clusters (BCGs) which include a peptidase which is predicted to be specific for D-amino acids. Further, 72 of these BCGs are predicted to incorporate an N-terminal D-Asn and encode an associated D-stereospecific peptidase, underscoring the importance of understanding this prodrug resistance mechanism in detail.

We next turned our attention to the enigmatic, C-terminal portion of the substrate. Candidate precolibactins isolated to date possess diverse structural features in this region, including a cyclopropane, lactams, pyridines, and one or more thiazole rings. We incubated ClbP$_{FL}$ with substrates bearing different amino acid side chains at this position and observed cleavage of all of these substrates by LCMS. As expected, the enzyme appears to be able to accommodate significant variation at this position, which is not surprising given that the crystal structure of ClbP$_{Pep}$ shows an exceptionally large groove around the catalytic motif. While it would be interesting to explore how larger substrates might interact with more of this active site, we chose to focus our work on the groups closest to the scissile bond, in order to inform the design of synthetic tools to monitor ClbP.

We next sought to develop a fluorogenic probe that could measure ClbP activity in a continuous assay format. Prior studies have made use of three-component probes which incorporate a recognition motif for the enzyme of interest and a fluorophore that activates upon release, connected by a self-immolating linker. We designed a probe that would incorporate an acyl-D-Asn recognition element, a 7-hydroxy-4-methylcoumarin fluorophore, and an ethylenediamine linker. We envisioned that this probe would be activated in a similar manner to the colibactin genotoxin, with hydrolysis of the amide bond adjacent to the D-Asn residue revealing a primary amine. This amine could undergo a rapid 5-exo-trig cyclization onto a carbamate linker to release the active fluorophore. Following these design principles, we synthesized probe (15) in order to mimic the known precolibactin structure as closely as possible. This substrate was activated by ClbP but faced solubility issues and poor performance in some of the cell-based assays describe below. Using the insight from our SAR study, we next synthesized compound (16). Both probes can be synthesized in 9 steps from commercially available materials (see, e.g., Example 3).

Figure 3A:
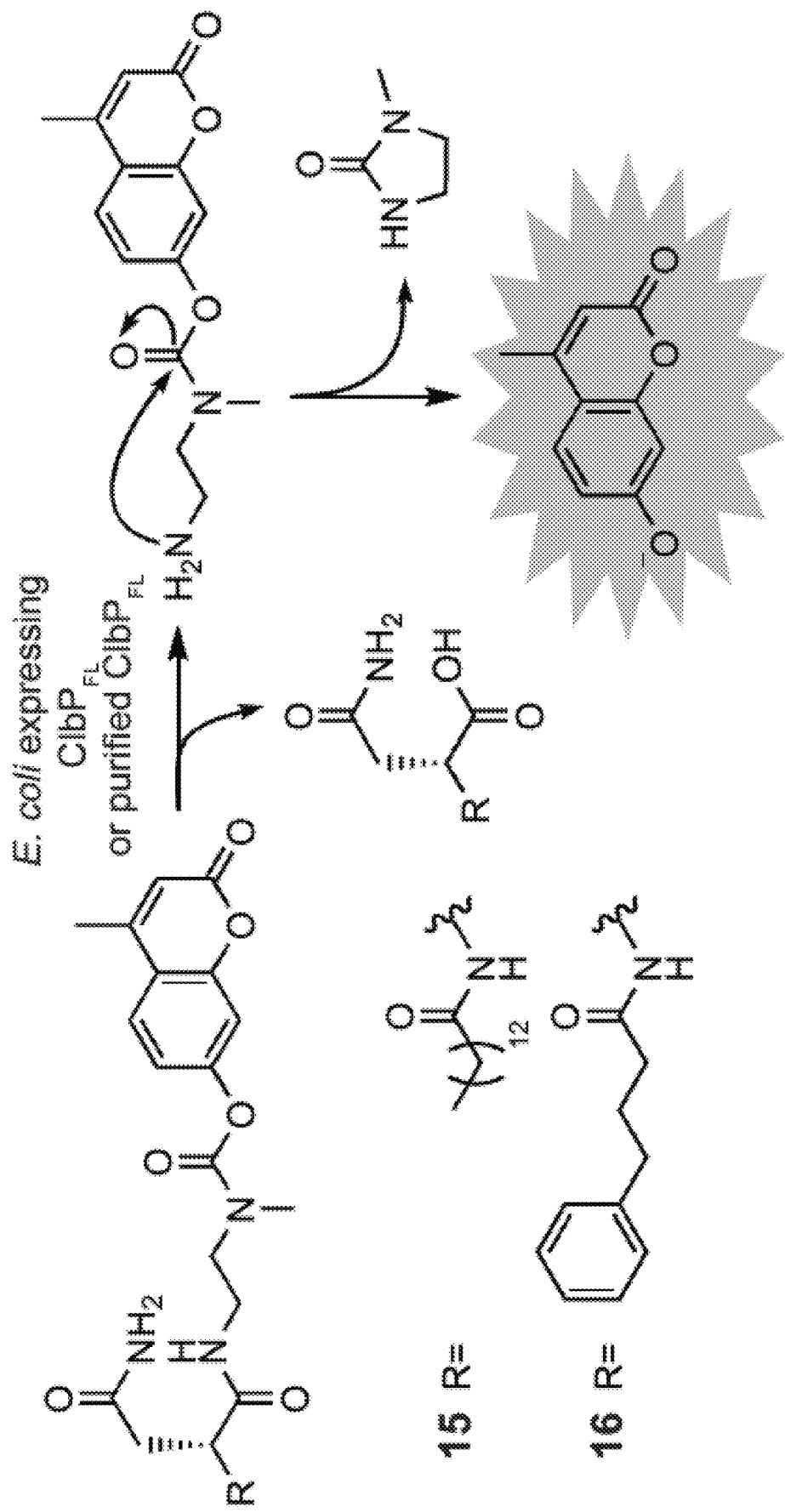
FIGS. 3A-3B depict the validation of the fluorogenic probe.
Figure 3B:
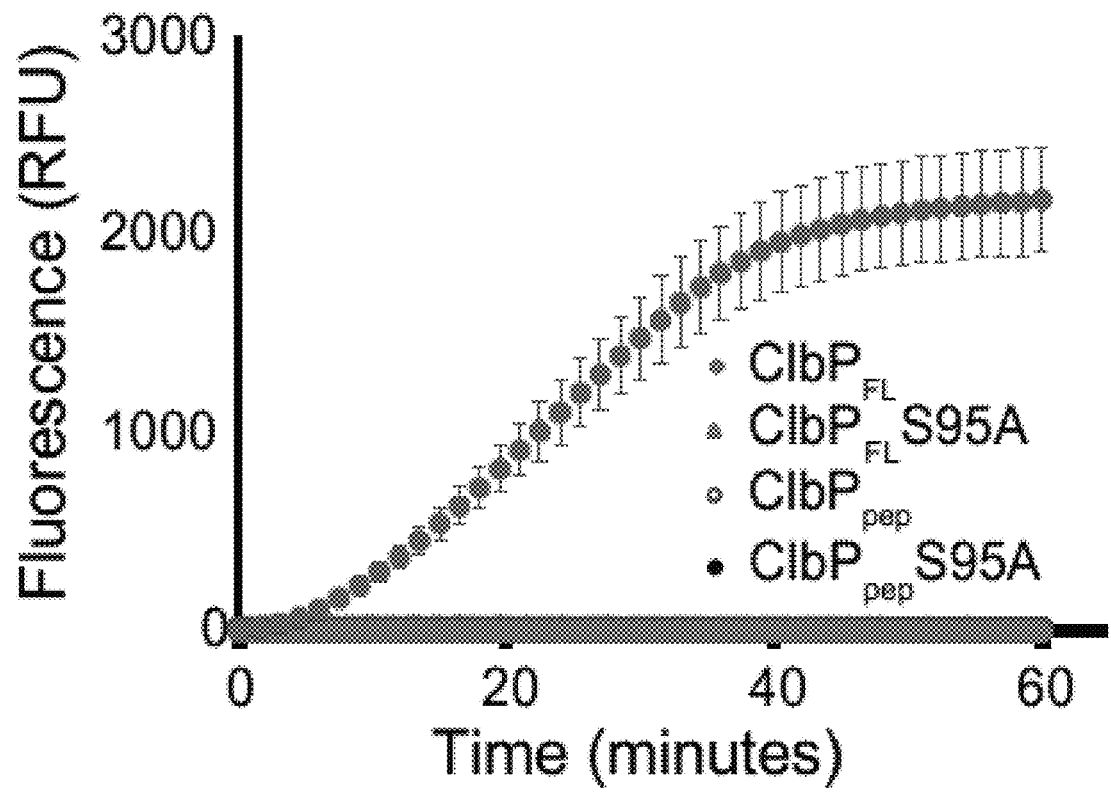
Figure 3B:
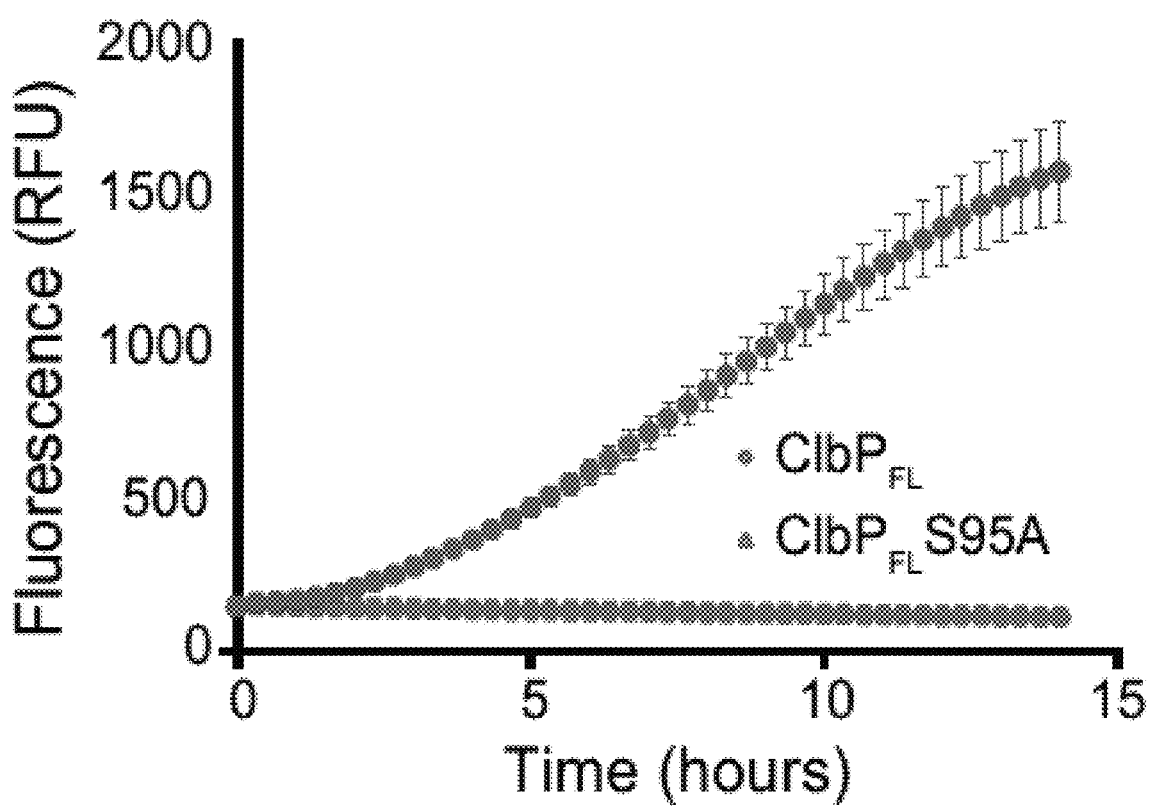

Compound (16) is cleaved rapidly by the full-length enzyme in vitro and shows negligible background activity with the S95A mutant and Clb$_{pep}$. The probe is stable in DMSO stock solutions, in vitro assay buffer conditions, and media for whole-cell assays. In an in vitro assay with 50 µM fluorogenic substrate, cleavage by ClbP results in a >100-fold increase in fluorescence relative to the negative control in less than 30 minutes (Z'-score>0.75, FIG. 3B). We also tested this probe in a whole-cell assay format using *E. coli* BL21 overexpressing full length ClbP or the S95A mutant. Here also, the probe shows robust and consistent cleavage by ClbP and low background signal in the negative control and parental strain (FIG. 3B).

Figure 4:
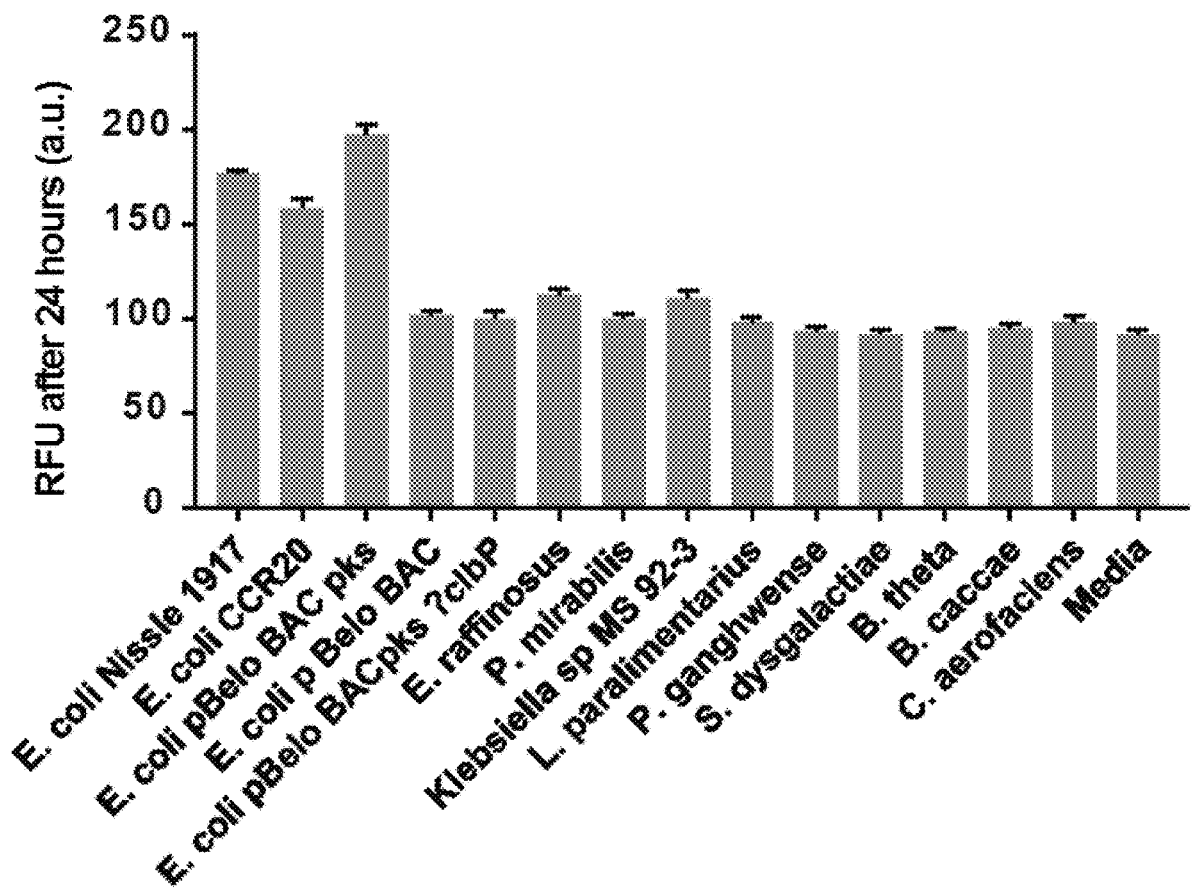
FIG. 4 demonstrates uses of the fluorogenic probe, phenotypic assay and inhibitor screening. The fluorogenic probe (16) can be used as a readout of ClbP activity to identify wild-type pks+ strains.

One potential use of our fluorescent probe is in the detection of pks+ strains in human samples. To do this, the assay must be sensitive enough to be activated by ClbP when it is expressed at much lower levels than in a laboratory overexpression strain and do so under anaerobic conditions. Indeed, we can reliably detect activation of probe (16) after overnight incubation with two different natively pks+ strains—*E. coli* CCR20 and *E. coli* Nissle 1917. Incubation of (16) with a panel of other gut isolates under the same conditions show low background activation of the probe (FIG. 4).

Finally, we also investigated whether our in vitro assay format could be used to detect inhibition of ClbP by small molecules. Previously reported ClbP inhibitors abrogate the genotoxicity of pks+ *E. coli* toward mammalian cells in tissue culture, but ability to inhibit the activity of ClbP has not been demonstrated. We tested whether (17) and (18) could block cleavage of our fluorogenic probe by ClbP but did not observe any inhibition, either in vitro or in whole cells (FIG. 5 and Example 3). We also used LCMS to evaluate the ability of these molecules to inhibit processing of the precolibactin mimic (1) by ClbP. Again, we observed no ClbP inhibition at concentrations up to 1 mM. These molecules are therefore unlikely to inhibit the catalytic activity of ClbP, and their reported genotoxicity-blocking effects may involve another target. Thus, there remains a need for potent and specific inhibitors of ClbP, as such compounds could provide tools to modulate and study colibactin production in animal models and complex communities. Our fluorogenic probe permits the discovery of such molecules via high-throughput screening.

Example 2

The genotoxin colibactin is produced by commensal and pathogenic strains of bacteria that harbor the pks island and has been linked to the development of colorectal cancer. In the final stages of colibactin's biosynthesis, an inactive precursor (precolibactin) undergoes proteolytic cleavage by ClbP, an unusual inner-membrane bound periplasmic peptidase, to release the active genotoxin. While this enzyme presents a unique opportunity to monitor and modulate colibactin biosynthesis, its active form has not yet been studied in vitro and no tools exist to monitor its activity. Here, we describe the in vitro biochemical characterization of the catalytically active form of the full-length enzyme. We elucidate the substrate preferences of ClbP and use this information to develop a robust fluorogenic activity probe. The probe is hydrolyzed by ClbP both in vitro and in whole cells and can serve as a sensitive measurement of ClbP activity, as well as a phenotypic test for pks+ bacterial isolates.

The trillions of microorganisms living on and in the human body, known as the human microbiota, have been implicated in a wide variety of diseases, including cancer. In particular, strains harboring the pks pathogenicity island have been identified as a possible risk factor for the development of colorectal cancer (CRC), and are found in the intestinal communities of more than 20% of humans. The pks island encodes a hybrid polyketide synthase-nonribosomal peptide synthetase (PKS-NRPS) assembly line that synthesizes the small molecule genotoxin colibactin. Prior work has shown that pks+ *E. coli* induce DNA double-strand breaks (DSBs) in eukaryotic cells and increase tumor load in a genetically susceptible mouse model of CRC in an inflammation-dependent fashion. Additionally, pks+ organisms are found more frequently in colons of patients with CRC and inflammatory bowel disease (IBD) compared to healthy controls. Despite these strong links to human disease, our understanding of colibactin's mechanism of action and role in carcinogenesis is limited, since the active molecule has never been isolated or structurally characterized.

The first insights into colibactin's chemical structure and activity were gained from studying its prodrug resistance mechanism. Biochemical characterization of the assembly line enzymes revealed that colibactin is initially synthesized as a larger, inactive precursor (precolibactin) and then cleaved by ClbP to liberate the active genotoxin (FIG. 1). These early studies, however, were unable to explain why ClbP is essential for genotoxicity. Deletion of this enzyme can cause a build-up of upstream intermediates and shunt metabolites (candidate precolibactins). Several groups employing this strategy have reported that many precolibactins contain a cyclopropane ring. Cleavage by ClbP allows the formation of an iminium in conjugation with the cyclopropane, providing the necessary electrophilic activation for DNA alkylation. This model of colibactin reactivity is supported by the recent isolation of a DNA adduct from HeLa cells exposed to pks+ *E. coli*.

Previous work on the structure and function of ClbP revealed that this enzyme possesses three C-terminal transmembrane (TM) helices which anchor it to the inner membrane and a soluble periplasmic peptidase domain. Prior attempts to study this enzyme have all relied on purifying the peptidase domain alone (ClbPpep), but this construct is not able to rescue genotoxicity in a ΔclbP mutant and shows a different reactivity profile than full-length ClbP (ClbPFL) in whole cells. In fact, deletion of even one of the TM helices blocks genotoxicity completely, even though ClbP can still fold insert in to the inner membrane.

Precolibactin is synthesized by the NRPS-PKS assembly line and tailoring enzymes encoded in the pks island before being cleaved by ClbP in the periplasm. This hydrolytic activation enables a cyclization event which enhances the electrophilicity of the cyclopropane warhead.

Figure 2C:
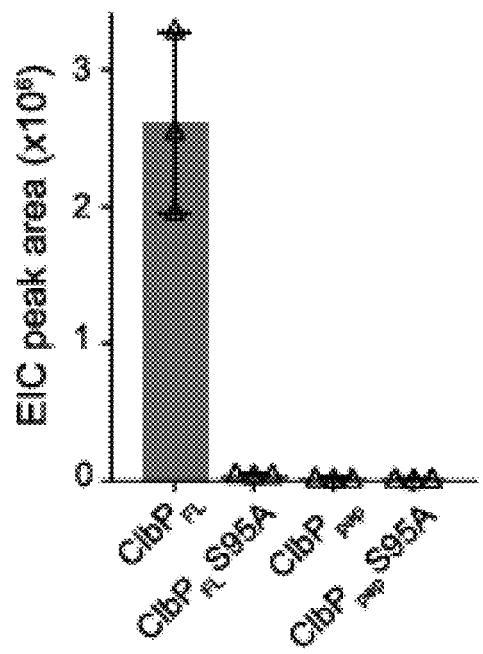
FIG. 2C depicts LC-MS detection of the prodrug scaffold ([M+H]+: 343.2597 m/z) produced by ClbP-mediated hydrolysis of 100 µM 2 in vitro. Error bars represent 1 standard deviation (SD), n=3.
Figure 2C:
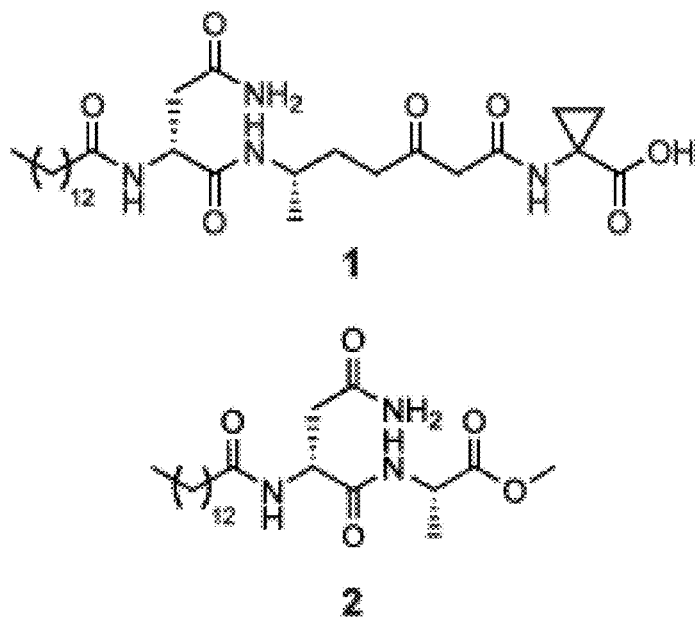
Figures 6A, 6B:
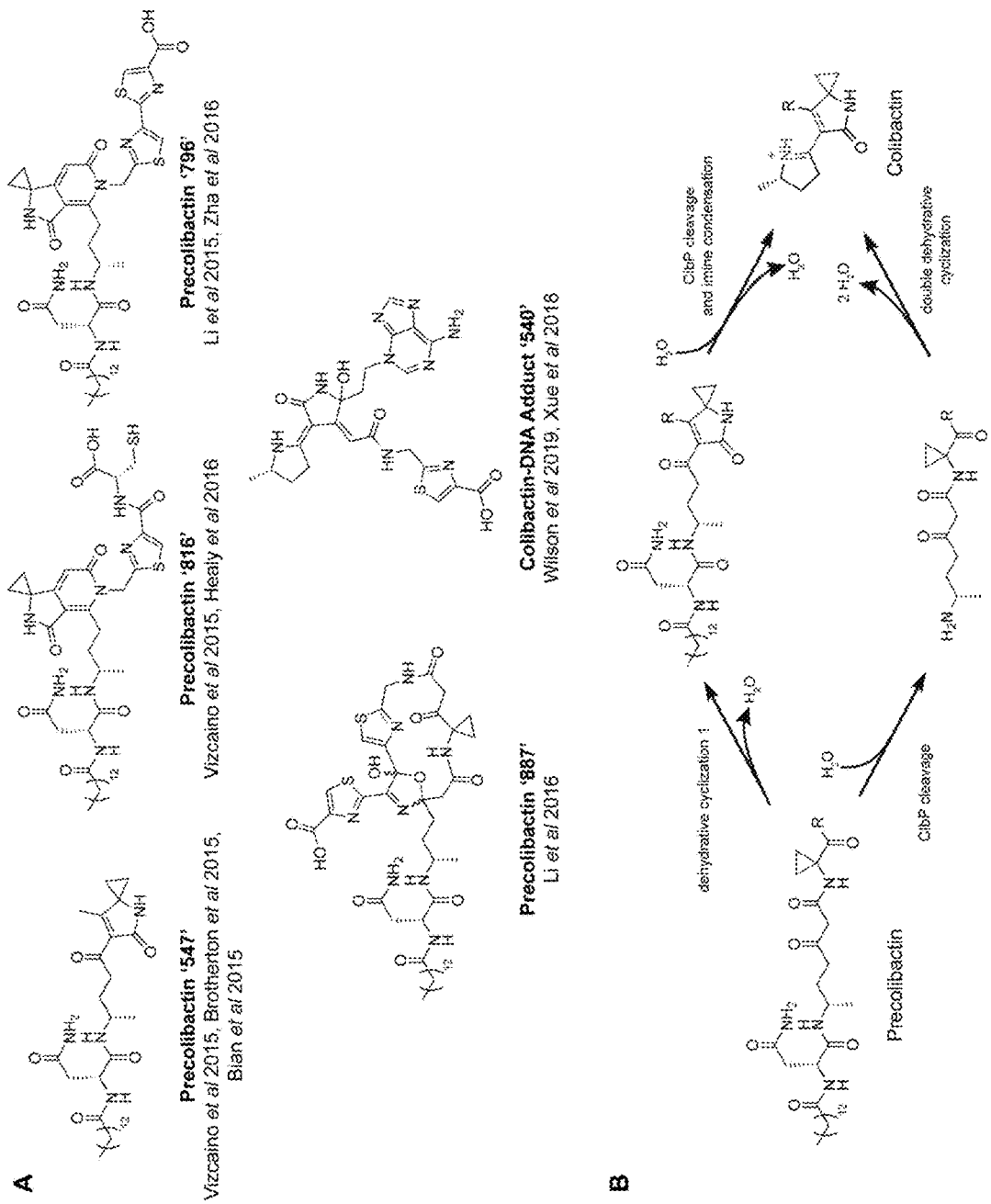
FIGS. 6A-6B depict the structures of selected candidate precolibactins and colibactin-derived DNA adducts.
Figure 7:
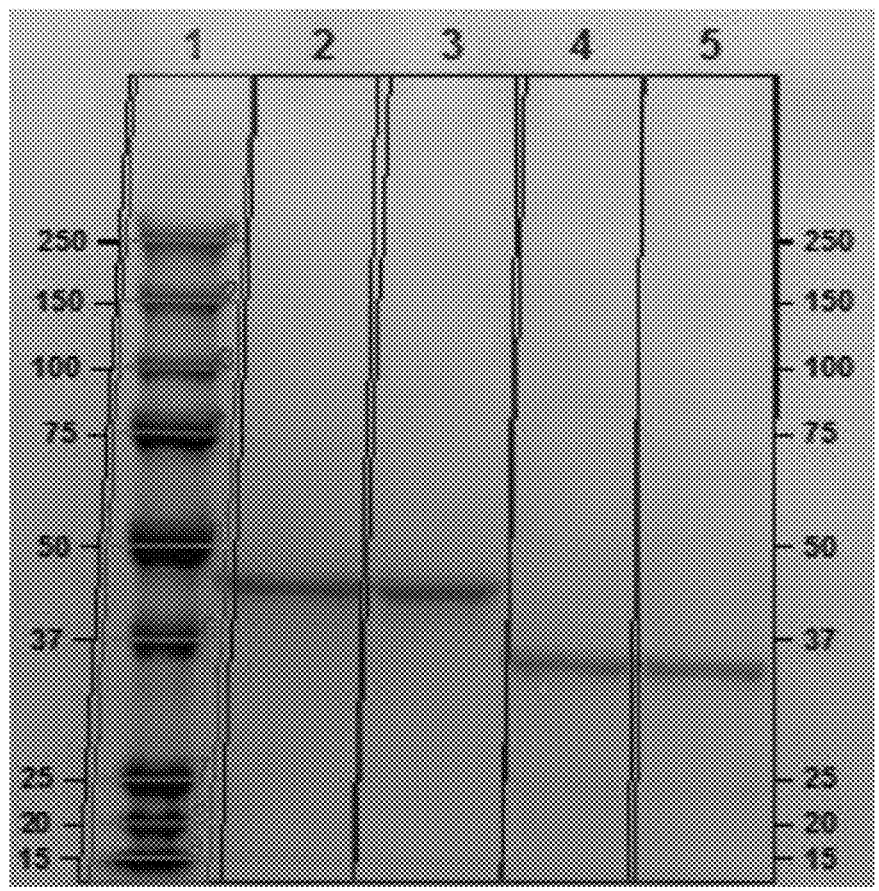
FIG. 7 depicts ClbP$_{FL}$ and ClbP$_{pep}$ analyzed by SDS-PAGE (4-12% Bis-Tris NuPAGE gel, ThermoFisher). Lanes: 1-Precision Plus Protein™ All Blue standard (Bio-Rad), 2-ClbP$_{FL}$-CHis$_{10}$, 2-ClbP$_{FL}$-S95A-CHis$_{10}$, 3-ClbP$_{pep}$-CHis$_6$, 4-ClbP$_{pep}$-S95A-CHis$_6$. Numbers in black indicate masses of standards in kDa.
Figure 8:
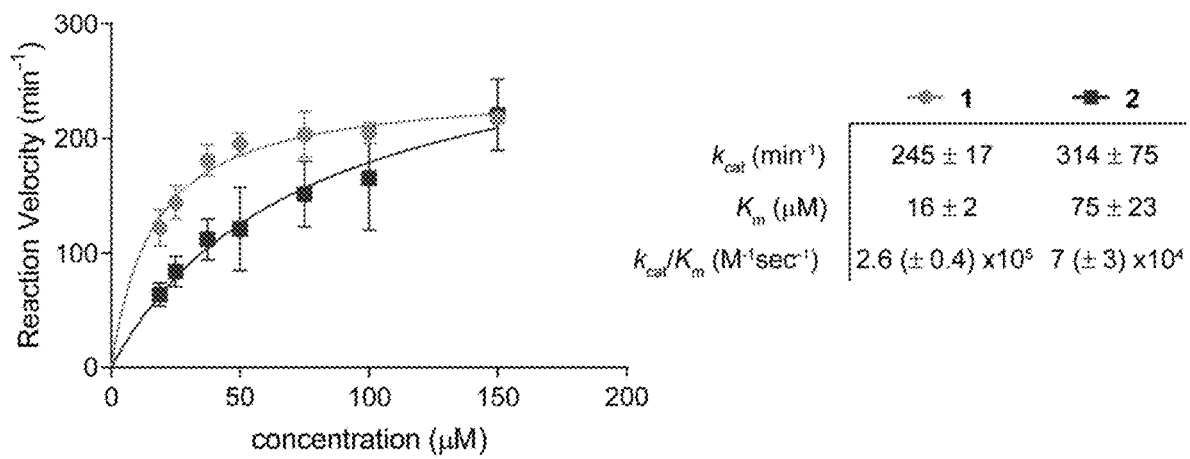
FIG. 8 depicts the kinetics of ClbP$_{FL}$-mediated cleavage of substrates 1 and 2. Each data point is an average of 3 biological replicates with error bars representing 1 SD. Solid lines are non-linear regression fits of data points to the Michaelis-Menten equation.
Figures 9A, 9B:
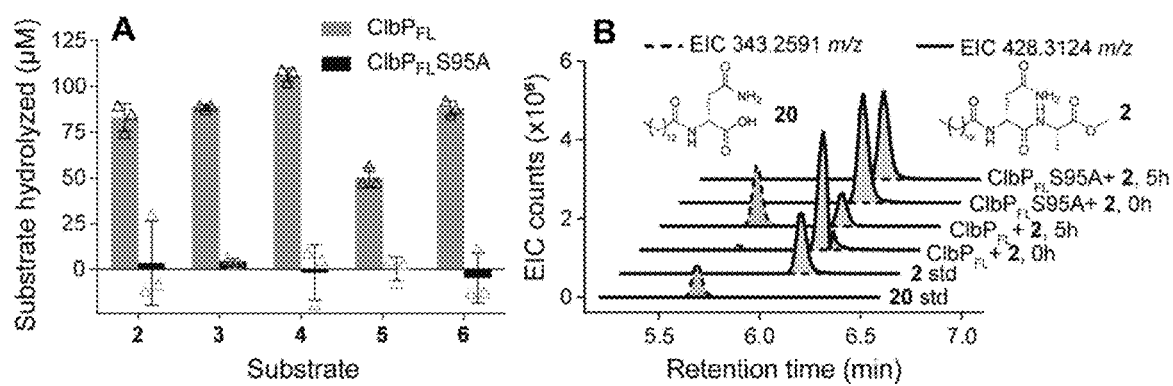
FIGS. 9A-9B depict the cleavage of substrates with varying R$_1$ groups (2-6) by ClbP$_{FL}$.
Figures 10A, 10B, 10C, 11:
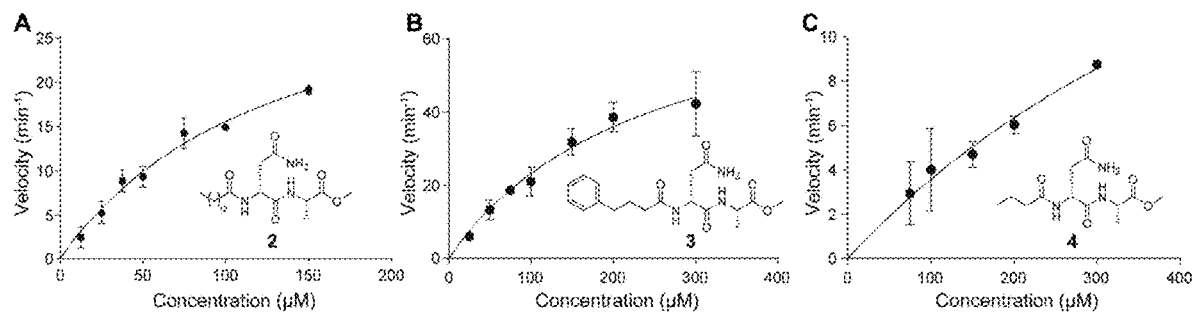
FIGS. 10A-10C depict the kinetics of ClbP$_{FL}$-mediated cleavage of substrates (FIG. 10A) 2, (FIG. 10B) 3, and (FIG. 10C) 4. Each data point is an average of 3 biological replicates with error bars representing 1 SD. Solid lines are non-linear regression fits of data points to the Michaelis-Menten model.
FIG. 11 depicts the kinetic parameters for substrates 2, 3, and 4.
Figures 12A, 12B, 12C, 12D, 12E, 12F:
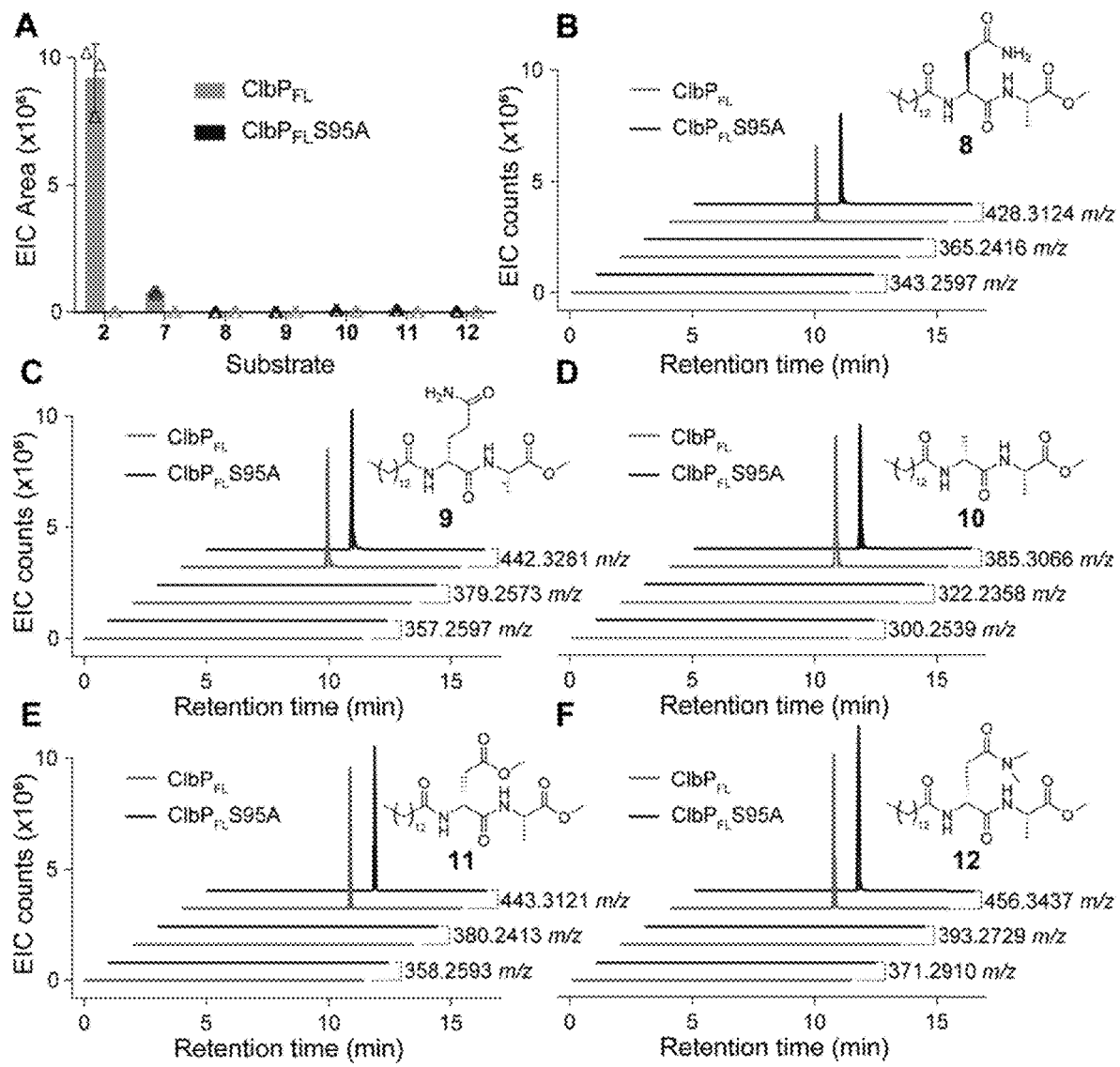
FIGS. 12A-12F depict the cleavage of substrates with varying R₂ groups (2, 7-12) by ClbP$_{FL}$.
Figure 13:
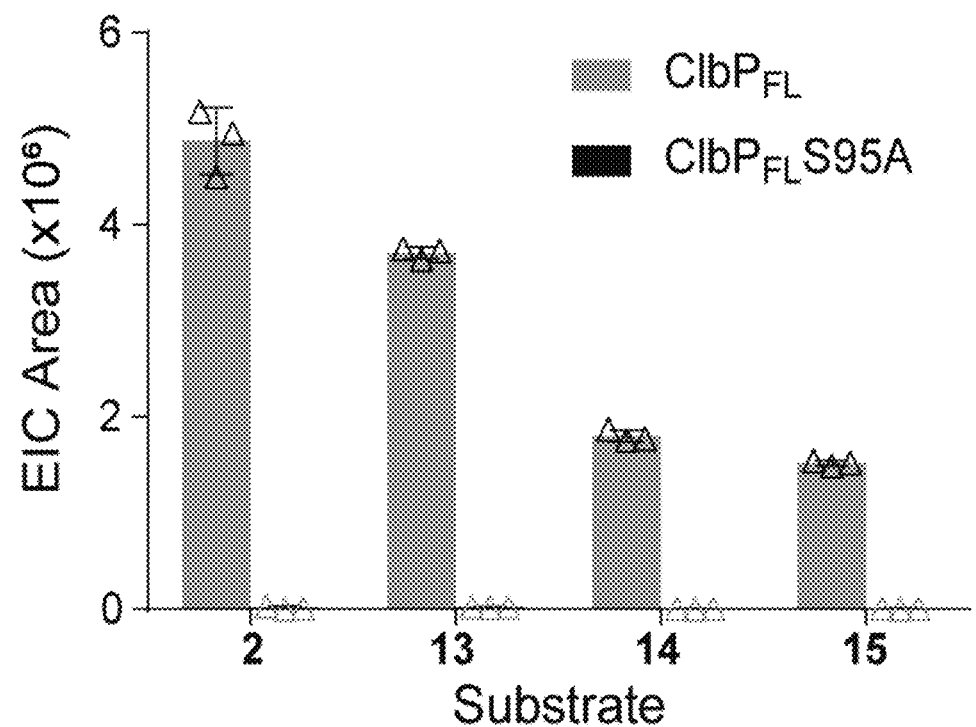
FIG. 13 depicts the cleavage of substrates with varying R₃ groups (13-15) by ClbP$_{FL}$. Bars represent average EIC peak areas for the [M+H]⁺ ion of the expected cleavage product, 20 (343.2597 m/z) which is the same for these four substrates. All substrates were tested in triplicate; triangles show individual replicate values (error bars=1 SD). First series is ClbP$_{FL}$ and second series is ClbP$_{FLS95A}$

In order to more fully characterize the activity of intact ClbP, we cloned and overexpressed full-length ClbP (ClbPFL), as well as the catalytically inactive mutant (ClbPFL-S95A) with a C-terminal histidine tag in *E. coli* BL21 (FIGS. 6A-6B). ClbPFL cleaved precolibactin-mimic substrate (1) rapidly in vitro, while ClbPFL-S95A and ClbPpep showed no cleavage activity by LC-MS (FIG. 2C).

We cloned and overexpressed C-terminal His10-tagged ClbP with its TM helices intact (ClbPFL-CHis10), as well as an inactive mutant lacking the catalytic serine nucleophile (ClbPFL-S95A-CHis10), in *E. coli* C41. We obtained purified enzyme by separating the cell components using ultracentrifugation, solubilizing the membranes in an n-dodecyl-β-D-maltoside (DDM)-containing buffer, and performing immobilized metal affinity chromatography. Because the structure of precolibactin has not yet been fully elucidated, we tested purified ClbPFL against a variety of synthetic precolibactin analogues. We found that ClbPFL cleaves isolated candidate precolibactins, such as 1 as well as the simplified precolibactin mimic 2 rapidly in vitro, while ClbPFL-S95A and ClbPpep showed no activity by LC-MS (FIG. 2C). The kinetic parameters for cleavage of 1 and 2 by ClbPFL were comparable, indicating the importance of the prodrug scaffold for recognition and catalysis. We chose substrate 2 for a more detailed structure—activity relationship (SAR) study.

To determine the key features for enzyme-substrate recognition, we conducted a structure-activity relationship (SAR) study using precolibactin mimic (1) as our starting scaffold. We first investigated the N-acyl chain of the prodrug scaffold. It was expected that the enzyme would accommodate some variation at this position, since *E. coli* overexpressing ClbPFL can hydrolyze synthetic substrates similar to (1) bearing shorter fatty acyl chains (Brotherton JACS 2013). We synthesized a series of precolibactin mimics which varied the N-acyl chain length, polarity, and steric bulk (FIG. 2B). LC-MS assays confirmed that ClbP hydrolyzed all of these substrates at the expected peptide linkage. Using a higher-throughput fluorescence derivatization assay, we determined the kinetic parameters for several of these substrates (FIG. 2B). The higher kcat and lower KM of more hydrophobic, long-chain substrates suggests that this may be an important, though non-essential, recognition feature. If substrate binding requires interaction with the hydrophobic transmembrane helices, this could also explain their necessity for genotoxicity.

These observations, together with the fact that ClbPpep cannot process 2 but retains some weak activity toward smaller substrates, indicate that the TM helices could play a role in substrate binding by interacting with the hydrophobic cyl substituent.

We next tested the ability of $ClbP_{FL}$ to hydrolyze substrates bearing different amino acids within the prodrug scaffold. When $ClbP_{FL}$ was incubated with substrates containing L-Asn (7), D-Gln (8), and D-Ala (9), no cleavage products were detected by LC-MS (SI). The D-Asp containing substrate (6) was cleaved in low amounts by $ClbP_{FL}$ (~100 fold less than (1)), however, we observed no cleavage of the corresponding D-Asp methyl ester (10) and D-Asn dimethylamide (11) substrates. These results indicate that this amino acid position is a key recognition motif, and that preserving the size and stereochemistry of this side chain are essential for ClbP binding and cleavage. Additionally, two closely related homologues of ClbP, ZmaM and XcnG, are also known to hydrolyze substrates containing D-Asn at the same position, suggesting that this feature is evolutionarily conserved.

After identifying ClbP's high selectivity for the D-Asn moiety, we wondered if the enzyme would exhibit similar selectivity for the second amino acid position. Although all candidate precolibactins characterized to date have L-alanine at this position, ClbBNRPS, the module responsible for this elongation step in biosynthesis, has been shown to accept other amino acids in vitro. We incubated ClbPFL with substrates (12)-(14) and observed cleavage of all of these substrates by LC-MS. The fact that ClbPFL can accommodate some variation at this position is in line with the observation that crystal structure of ClbPPep shows an exceptionally large groove around the catalytic residues. The native precolibactin substrate of ClbP is likely a larger molecule than the substrates tested here, and there are many more possible interactions with this large groove which could be explored. We chose to focus our work on the groups closest to the scissile bond, in order to inform the design of synthetic tools to monitor ClbP.

Building on the insight from our SAR study, we designed a fluorogenic probe that could measure ClbP activity in a continuous assay format. This type of probe would incorporate the key recognition features of a D-Asn residue and large hydrophobic group, a fluorophore, and an ethylenediamine linker. We envisioned that this probe would be activated in a similar manner to the colibactin genotoxin, with hydrolysis of the amide bond adjacent to the D-Asn residue revealing a primary amine. The resulting amine intermediate could then undergo a rapid 5-exo-trig cyclization to release the active fluorophore. Following these design principles, we synthesized probe (15) in order to mimic the known precolibactin structure as closely as possible in 9 steps from commercially available starting materials. Probe (15) was processed by ClbPFL in vitro and in whole cells, but faced solubility issues and poor performance in some cell-based assays. Notably, the activation of 15 is analogous to precolibactin activation: hydrolysis by ClbP reveals a primary amine, which can undergo a rapid 5-exo-trig cyclization to produce the active species. While $ClbP_{FL}$ processed 15 in vitro and in live *E. coli*, its low solubility and membrane permeability likely led to poor performance in some cell-based assays.

Since our SAR work indicated that (2) was hydrolyzed almost as efficiently as (1), we made an analogous modification to our design and synthesized compound (16).

Compound (16) is cleaved rapidly by the full-length enzyme in vitro and shows negligible background activity with the S95A mutant and ClbPpep. The probe exhibited excellent stability in DMSO stock solutions, in vitro assay buffer conditions, and LB and MEGA media. In an in vitro assay with 50 fluorogenic substrate, cleavage by ClbP results in a >100-fold increase in fluorescence relative to the negative control in less than 30 minutes (Z'-score>0.75, FIG. 3B). Moreover, the probe shows robust and consistent cleavage by ClbP in a whole-cell assay format with *E. coli* BL21 overexpressing ClbP and low background signal in the negative control and parental strains (FIG. 3B).

Figure 5A:
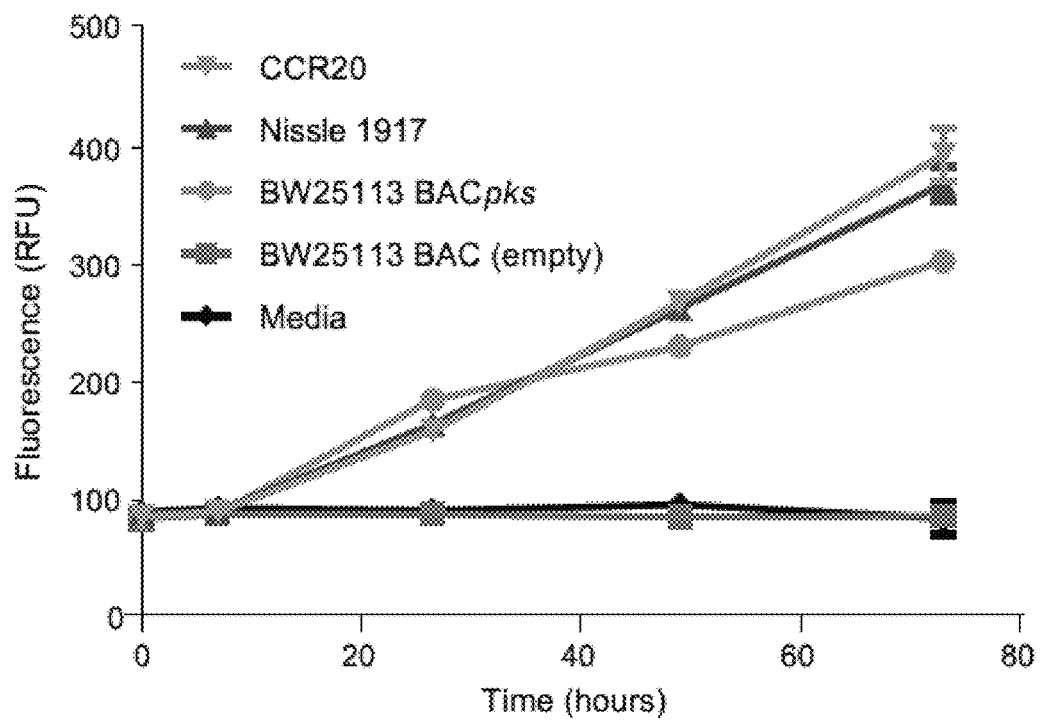
FIGS. 5A-5C demonstrates that probe (16) can be used as an indicator of pks+ strains. Strains were grown in MEGA media under anaerobic conditions with 100 µM (16). The bar graph further demonstrates the effect of the boronic acid compounds (17) and (18) on ClbP activity. ClbP-FL (0.1 µM) and the indicated concentration of (17) or (18) were preincubated for 1 hour before initiating the reaction with the addition of (16).
Figure 5B:
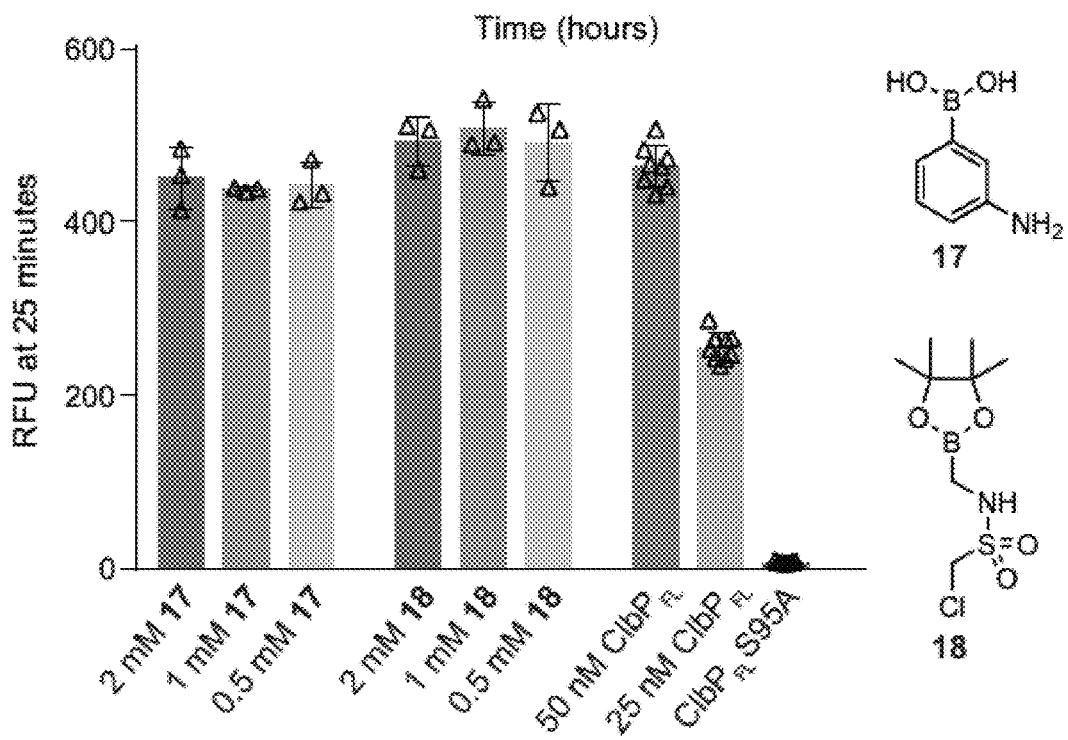
Figure 5C:
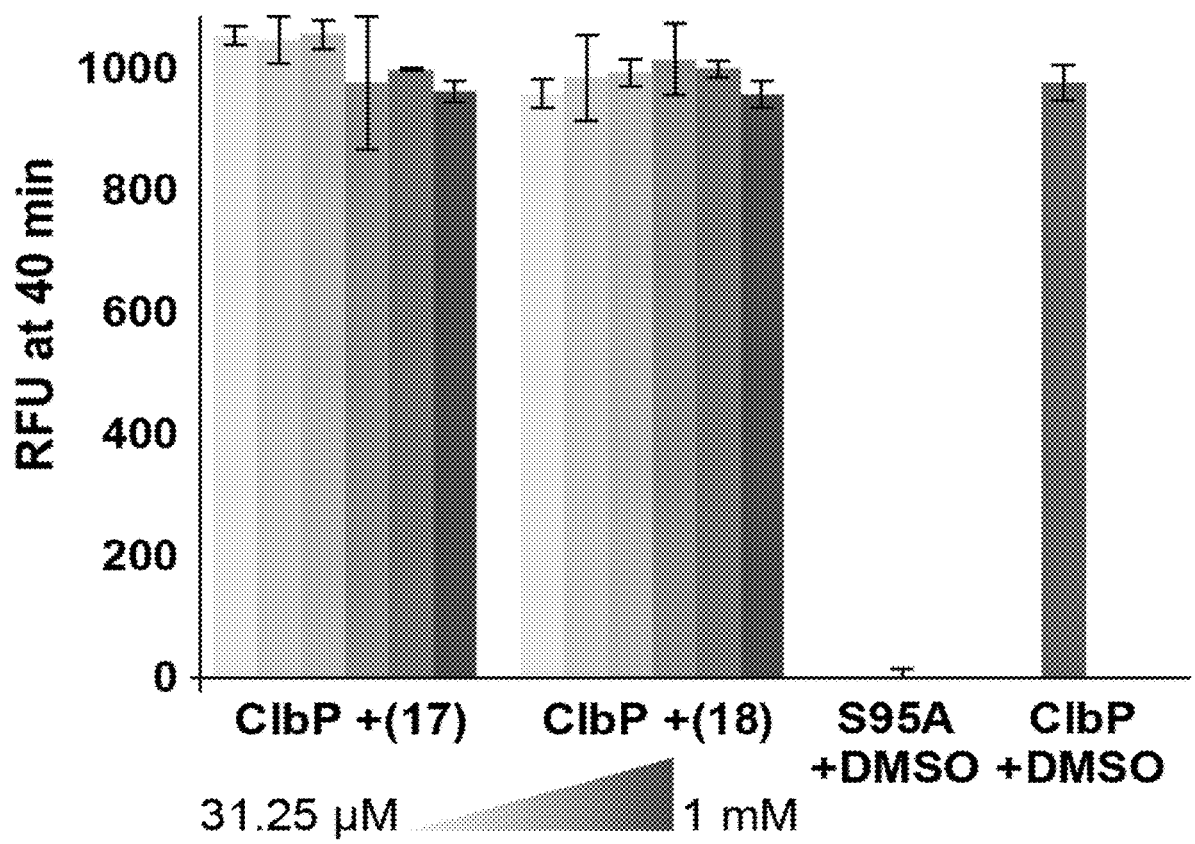
Figure 5C:
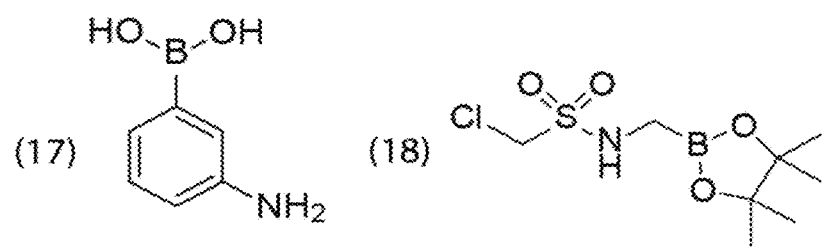

One potential use of our fluorescent probe is the detection of pks+ strains in human samples. To do this, the assay must be sensitive enough to be activated by ClbP when it is expressed at much lower levels than in a laboratory overexpression strain under anaerobic conditions. Indeed, we can reliably detect activation of probe (16) after overnight incubation with the two native pks+ strains, *E. coli* CCR20 and *E. coli* Nissle 1917. Incubation of (16) with a panel of other gut isolates under the same conditions show low background activation of the probe (FIG. 5A).

Finally, we also investigated whether our in vitro assay format could be used to detect inhibition of ClbP by small molecules. Previously reported ClbP inhibitors ((17) and (18)) abrogate the genotoxicity of pks+ *E. coli* toward mammalian cells in tissue culture, but their effect on the catalytic activity of ClbP has not been examined. When ClbPFL was incubated with (17) or (18) and probe (16), we did not observe any decrease in the rate of increase of fluorescence or the total fluorescent signal produced (FIG. 5). Repeating this experiment with whole cells overexpressing ClbP yielded similar results (see Example 3). To ensure that this was not an artefact of our fluorogenic assay format, we also used LCMS to evaluate the ability of these molecules to inhibit processing of the precolibactin mimic (1) by ClbPFL in vitro. Again, we observed no ClbP inhibition at concentrations up to 1 mM (see Example 3). Thus, the ability of these molecules to abrogate the genotoxicity of pks+ *E. coli* likely involves engaging another cellular target (s). As a result, there remains a need for potent and specific inhibitors of ClbP. Our fluorogenic probe now permit the discovery of such molecules via high-throughput screening, and permit the study of colibactin production in animal models and complex communities.

Despite over a decade of research by multiple groups, the colibactin genotoxin has remained elusive, and the evidence of its carcinogenicity relies on correlations and models which cannot fully recapitulate the complexity of the gut microbiome. Our SAR work on ClbP substrates provides a valuable starting point for the rational design of more potent and specific inhibitors of ClbP, while our fluorogenic probe can act as a foundation for high-throughput screening toward the same goal. Such inhibitors would make possible much more detailed studies of colibactin's effects in more physiologically-relevant animal models and in complex communities. Moreover, these insights may translate to other natural product pathways of interest which contain ClbP homologues. Two of ClbP's closest relatives, ZmaM and XcnG, perform analogous functions in the biosynthesis of zwittermicin and xenocoumacin, respectively, hydrolyzing substrates that also contain an N-acyl-D-Asn motif, though their substrate scope has not been explored in vitro. There are likely many more enzymes closely related to these which have not yet been identified—genome mining has revealed thousands of biosynthetic gene clusters (BCGs) which include a predicted D-stereospecific peptidase. Of these, 72 are predicted to incorporate an N-terminal D-Asn and encode a peptidase which recognizes this motif Thus, ClbP may represent the most well-studied member of a much larger and ever-growing class of enzymes which participate in prodrug-resistance mechanisms.

Example 3

The genotoxin colibactin and its inactive precursor, precolibactin, have not yet been fully characterized. There have, however, been numerous reports of candidate precolibactins which have been isolated from pks+ strains of E. coli which do not express ClbP (FIGS. 6A-6B).1-7 Some candidate precolibactins are believed to be derived from on-pathway biosynthetic intermediates, while others are believed to arise from shunt products. Moreover, many of these structures are thought to arise from non-enzymatic chemistry unrelated to colibactin biosynthesis. The mechanism of colibactin activation presented in FIG. 1 has been supported by the structures of several candidate precolibactins as well as by the preparation of synthetic model precolibactins,4 biochemical studies of ClbP activity in whole cells,8 and the identification of putative colibactin-derived DNA adducts.9, 10 Based on the structures of candidate precolibactins identified to date, as well as the biosynthetic enzymes annotated in the pks island, the 'R' group as presented in FIG. 1 likely incorporates a glycine extender unit, one or more thiazole or thiazoline rings, and at least one structural motif derived from the unusual PKS building block aminomalonate. Based on the genetic, biochemical, and metabolomic evidence presented in the literature thus far, the most likely structure of precolibactin: 1) does not contain the bicyclic pyridone ring system found in precolibactin '816' and '796' (FIG. 6A) and 2) is not derived from the larger macrocycle found in precolibactin '887' (FIG. 6B). These ring systems cannot form the $\alpha,\beta$-unsaturated imine-conjugated cyclopropane ring system that is essential for alkylation activity4 and involved in DNA alkylation in cells and animal models.10 Whether the $\alpha,\beta$-unsaturated lactam ring bearing the spiro-cyclopropane ring forms before or after prodrug scaffold cleavage by ClbP remains an open question. Past work has shown that ClbP can process substrates bearing this and other ring systems,11 and here we show that ClbP can process a linear 1,3-dicarbonyl substrate, so the order of these steps remains to be determined (FIG. 6B)

General Materials and Methods

Oligonucleotide primers were synthesized by Integrated DNA Technologies (Coralville, Iowa). Recombinant plasmid DNA was purified with a Qiaprep™ Kit from Qiagen (Hilden, Germany). Gel extraction of DNA fragments and restriction endonuclease clean up were performed using an Illustra GFX™ PCR DNA and Gel Band Purification Kit from GE Healthcare. DNA sequencing was performed by Eton Bioscience, Inc. (Boston, Mass.). Nickel-nitrilotriacetic acid agarose (Ni-NTA) resin was purchased from Qiagen. SDS-PAGE gels were purchased from BioRad (Hercules, Calif.). Purified protein concentrations were determined by absorbance measurements at 280 nanometers taken on a NanoDrop™ 2000 UV-Vis Spectrophotometer (ThermoFisher Scientific, Waltham, Mass.) using extinction coefficients calculated based on protein sequences using the ExPASY online tool (available on the world wide web at web.expasy.org/protparam/). Luria-Bertani (LB) and Terrific Broth (TB) media were obtained from EMD Millipore (Darmstadt, Germany) or Alfa Aesar (Tewksbury, Mass.). Isopropyl $\beta$-D-1-thiogalactopyranoside (IPTG) was purchased from Teknova (Hollister, Calif.) and Dodecyl maltoside (DDM) was purchased from Chem Impex International Inc (Wood Dale, Ill.). All other chemicals were purchased from Sigma-Aldrich (St. Louis, Mo.) unless otherwise noted.

Optical densities of E. coli cultures were determined with a DU 730 Life Sciences UV/Vis spectrophotometer (Beckman Coulter, Indianapolis, Ind.) by measuring absorbance at 600 nm. Ultracentrifugation was performed on a Beckman-Coulter Optima XE-90 Ultracentrifuge fitted with a type 45 Ti rotor in 70 mL polycarbonate tubes. Solvents and formic acid used for LC-MS were B & J Brand High Purity Solvents (Honeywell Research Chemicals). High-resolution LC-MS analyses of enzyme assays and synthetic compounds were performed on an Agilent 6530 Q-TOF Mass Spectrometer fitted with a dual-spray electrospray ionization (ESI) source. The capillary voltage was set to 3.5 kV, the fragmentor voltage to 175 V, the skimmer voltage to 65 V, and the Oct 1 RF to 750 V. The drying gas temperature was maintained at 275° C. with a flow rate of 8 L/min and a nebulizer pressure of 35 psi. A standard calibrant mix was introduced continuously during all experiments via the dual-spray ESI source. For analytical liquid chromatography, unless otherwise noted, experiments were performed using an Agilent Technologies 1200 series LC on a Hypersil GOLDaq™ C18 reverse phase column (50×3 mm, Thermo Scientific) with the following elution conditions: a gradient from 35% solvent A:65% solvent B to 100% solvent A over 5 minutes, holding at 100% A for 2 minutes, followed by a gradient back to 35% solvent A over 1 minute and holding at 35% solvent A for 3.5 minutes (solvent A: acetonitrile+0.1% formic acid; solvent B: water+0.1% formic acid; flow rate=0.4 mL/minute; injection volume=10 µL). All experiments were performed in positive ion mode, and the masses detected corresponded to [M+H]+ ions unless otherwise noted. Masses were found within 5 ppm of the expected [M+H]+ masses.

NMR chemical shifts are reported in parts per million downfield from tetramethylsilane using the solvent resonance as internal standard for 1H (CDCl3=7.26 ppm, DMSO-d6=2.50 ppm) and 13C (CDCl3=77.25 ppm, DMSO-d6=39.52 ppm). Data are reported as follows: chemical shift, integration multiplicity (s=singlet, d=doublet, t=triplet, q=quartet, quint=quintet, sext=sextet m=multiplet), coupling constant, integration, and assignment. All solvents for synthesis were obtained from Sigma-Aldrich, with the exception of methanol (EMD Millipore). All NMR solvents were purchased from Cambridge Isotope Laboratories (Tewksbury, Mass.). NMR spectra were collected in the Magnetic Resonance Laboratory in Harvard University Department of Chemistry and Chemical Biology and visualized and processed using MestreNova™, version 11.0.2-18153 (Mestrelab Research S.L., Escondido, Calif.) Optical rotation data were obtained using a 1 mL cell with a 0.5 dm path length on a Jasco P-2000 polarimeter equipped with a sodium (589 nm, D) lamp.

Preparative HPLC purification was run on a Dionex™ Ultimate 3000 instrument (Thermo Scientific) using Hypersil GOLDaQ™ column (250 mm×20 mm, 5 μm particle size, Thermo Scientific). Standard LC gradient conditions: 50% Solvent A for 2.5 minutes, gradient to 95% Solvent A over 7.5 minutes, hold at 95% Solvent A for 11.5 minutes, gradient to 50% solvent A over 1 minute, hold at 50% solvent A for 2.5 minutes (solvent A: HPLC-grade acetonitrile (VWR, HiPerSolv-Chromanorm)+0.1% formic acid; solvent B: water+0.1% formic acid; flow rate: 8 mL/minute; injection volume: 200 to 400 μL). All solvents were degassed by sonication prior to use. Compounds which were purified using different conditions are noted in the synthetic methods section below for that compound.

Strains of E. coli DH10B harboring pBeloBAC11-pks, as well as E. coli CCR20 were obtained from the Bonnet lab, Laboratoire de Bactériologie Clinique, Centre Hospitalier de Clermont-Ferrand, Clermont-Ferrand F-63003, France. The strain E. coli Nissle 1917 was obtained from the Müller lab, Helmholtz Institute for Pharmaceutical Research Saarland, Campus E8.1, 66123 Saarbrucken, Germany.

Cloning, overexpression, and purification of ClbPFL, ClbPFLS95A, ClbPpep, and ClbPpepS95A Mutagenesis to extend histidine tag: Plasmids for the expression of ClbPFL and ClbPFL-S95A have been previously reported.13 These plasmids (pET29b-ClbPFL-CHis6 and pET29b-ClbPFL-595A-CHis6 were used as templates for site-directed mutagenesis with the following primers: Forward—CCACCATCACCATCACT-GAGATCCGGCTGCTAACAAAGCCCGAAAG (SEQ ID NO: 2), Rev—CTCAGTGATGGT-GATGGTGGTGGTGGTGGTGGTGCTCGAGCTC (SEQ ID NO: 3). Reactions (50 μL total volume) were performed with 35.5 μL H2O, 5 μL 10X Pfu Ultra II buffer, 2.5 μL of NEB dNTP mix (10 mM each dATP, dCTP, dGTP, dTTP), 1 μL Pfu Ultra II, 1 μL template at 75 ng/μL, 2.5 μL 10 μM forward primer, 2.5 μL 10 μM reverse primer. For PCR, reaction mixtures were heated to 95° C. for 30 seconds and then were cycled 20 times at 95° C. for 30 seconds, 50° C. for 1 minute, 68° C. for 7 minutes, followed by a final extension at 68° C. for 8 minutes. Successful amplification was confirmed by running agarose gel electrophoresis, and template DNA was removed by digestion for 1 hour at 37° C. with 1 μL of DpnI. Digested reactions were used to transform chemically competent E. coli DH5α cells, and plasmids were isolated from cultures of single colonies. Mutagenesis was confirmed by sequencing isolated plasmid DNA.

Transformation of E. coli for expression of ClbPFL-CHis10: OverExpress C41(DE3) chemically competent cells were obtained from Lucigen (Madison, Wis.) and transformed with the constructs described above following the manufacturer's protocol. Following 1 hour of recovery in SOC medium after heat shock, each transformation was plated on to fresh LB agar plates containing 50 μg/ml kanamycin and incubated at 37° C. overnight.

Transformation of BW25113 cells with BAC for pks activity assays: The pBeloBAC11-pks BAC was isolated from E. coli DH10B harboring pBeloBAC11-pks using a BAC DNA Miniprep Kit (Zymo Research, Irvine, Calif.). The empty pBeloBAC11 BAC was isolated from E. coli K12 ER2420 harboring pBeloBAC11 (New England Biolabs, Ipswich, Mass.) using a Plasmid Miniprep Kit (Qiagen). To generate BW25113 E. coli strains harboring colibactin biosynthesis genes, electrocompetent BW25113 E. coli were electroporated (BioRad MicroPulser™, 1.8 kV, 0.1 cm cuvette) with pBeloBAC11-pks, pBeloBAC11-pksΔclbP, or pBeloBAC11. The transformed E. coli was then selected on LB agar plates containing either 25 μg/mL chloramphenicol or 25 μg/mL chloramphenicol and 50 μg/mL kanamycin.

Large scale overexpression and purification of ClbPFL and ClbPFL-S95A: A 50 mL starter culture of either E. coli C41 pET-29b-ClbPFL-CHis10 or E. coli C41 pET-29b-ClbPFL-S95A-CHis10 was inoculated from a single colony from an LB+kanamycin agar plate and grown overnight at 37° C. in LB medium (Lennox, Alfa Aesar) supplemented with 50 μg/mL kanamycin.

Overnight cultures were diluted 1:100 into 2 L of TB medium containing 50 μg/mL kanamycin. Cultures were incubated at 37° C. with shaking at 175 rpm, moved to 15° C. at OD600=0.5-0.8 and then induced with 500 μM IPTG. Cultures were incubated with shaking at 15° C. for approximately 20 h. Cells from the 2 L culture were harvested by centrifugation (6,000×g for 15 min at 4° C.). Cell pellets were flash frozen in liquid N2 and stored at −80° C. for a maximum of 2 days. Pellets were thawed and resuspended in lysis buffer (20 mM Sodium phosphate, pH 8.0, 500 mM NaCl, 55 mM imidazole, 5 mM MgCl2, 0.25 mg/mL Lysozyme, 10 μg/mL DNase I). Cells were lysed in 50 mL conical tubes on ice using a Branson Digital sonifier (Fisher Scientific, Hampton, N.H.) [10 second pulse at 25% amplitude with 20 seconds of rest for a total pulse time of 5 minutes, pausing to mix tube by inversion after 2.5 minutes]. Unbroken cells were removed by centrifugation (2,000×g for 10 minutes at 4° C.).

Supernatants were transferred to ultracentrifugation tubes, and membranes were isolated by centrifugation at 35,000 RPM for 70 minutes at 4° C. (average RCF for a Beckman-Coulter Type 45 Ti rotor at 35,000 RPM is approximately 95,000×g). The supernatant was removed, and the membrane pellet was resuspended with a detergent buffer (20 mM Sodium phosphate, pH 8.0, 500 mM NaCl, 55 mM imidazole, 1.5% w/v DDM+Pierce™ Protease Inhibitor (Thermo Scientific)) using an IKA T18 Basic Ultra-Turrax homogenizer (IKA Works, Inc., Wilmington, N.C.). The homogenate was nutated for 3 hours at 4° C. to dissolve membranes. The homogenate was centrifuged to remove insoluble cell debris (95,000×g for 35 minutes at 4° C.) and the supernatant containing solubilized cell membranes was collected. Ni-NTA resin (~1 mL per L of expression culture) was added to a gravity-flow column and washed with 3 column volumes of wash buffer (50 mM Tris, pH 8.0, 200 mM NaCl, 55 mM imidazole, 0.02% w/v DDM). Resin was resuspended in a minimal volume of wash buffer and added to the clarified membrane homogenate. The mixture was then incubated on a nutating mixer at 4° C. for 2 hours before collecting the resin by centrifugation (4,000×g 10 minutes at 4° C.). The resin was resuspended in a minimal volume of the residual homogenate and transferred by pipette to a gravity flow column fitted with a plastic stopcock. The resin was then washed with 2 column volumes of wash buffer and the protein eluted using a stepwise gradient of increasing imidazole in the wash buffer (55 mM, 100 mM, 200 mM, 450 mM). Fractions were collected for each column volume of wash buffer and analyzed by SDS-PAGE (4-15% Tris-HCl gel) for the presence of the desired protein. Fractions containing the desired protein were pooled and dialyzed twice against 200 volumes of storage buffer for each round (50 mM Tris, pH 8.0, 200 mM NaCl, 0.02% w/v DDM), first for 4 hours, then overnight. The dialyzed protein was then concentration in 100 kDa MWCO* Amicon® Ultra spin filters (Corning, Corning, N.Y.). Concentrated protein was then flash frozen as 10-15 μL droplets in liquid N2 and stored at −80° C. Yield: 1.4-1.8 mg/L culture

*Although the mass of ClbPFL is only ~50 kDa, a larger molecular weight cut-off (MWCO) is necessary for this step because membranes with lower MWCOs do not permit DDM to pass through efficiently, resulting in a significant over concentration of the detergent. Analysis of the protein concentrate and flow through by A280 measurements showed that ClbPFL is completely retained by a 100 kDa MWCO filter, which is likely due to the larger effective size of the complex formed by the enzyme and DDM micelle.

Large scale overexpression and purification of ClbPpep and ClbPpep-S95A: ClbPpep and ClbPpep-S95A were purified as previously reported using the same plasmids and expression strains, with the modifications described below.13

A 50 mL starter culture of *E. coli* BL21 pET-29b-ClbPpep or pET-29b-ClbPpep-S95A was inoculated from frozen stock and grown overnight at 37° C. in LB medium supplemented with 50 μg/ml kanamycin. Overnight cultures were diluted 1:100 into 2 L of LB medium containing 50 μg/mL kanamycin. Cultures were incubated at 37° C. with shaking at 175 rpm. Protein expression was induced with 500 μM IPTG at OD600=0.6-0.7, and cultures were moved to 15° C. and incubated for ~20 h. Cells from the 2 L culture were harvested by centrifugation (6,000×g for 15 min) and resuspended in Tris/Sucrose buffer (30 mM Tris-HCl, pH 8.0, 20 wt % sucrose), 80 mL buffer per gram of cell pellet. To this mixture was added EDTA (1 mM final concentration) dropwise with stirring. This mixture was allowed to stir at 4° C. for 10 min and was then centrifuged (6,000×g for 20 min at 4° C.). The supernatant was removed, and the cell pellet was resuspended in 400 mL of 5 mM MgSO4. The suspension was allowed to stir at 4° C. for 10 min, and was then centrifuged (11,000×g for 20 min at 4° C.). The supernatant was incubated with 3 mL of Ni-NTA resin and 5 mM imidazole for 2 h at 4° C. This mixture was then poured onto a glass column and the solution eluted to give ~2 mL of Ni-NTA resin in a 5 mM imidazole solution. Protein was eluted from the column using a stepwise imidazole gradient (25 mM, 50 mM, 75 mM, 100 mM, 125 mM, 150 mM, 200 mM) in elution buffer (50 mM Tris-HCl, pH 8.0, 200 mM NaCl), collecting 2 mL fractions. SDS-PAGE analysis (4-15% Tris-HCl gel) was employed to ascertain the presence and purity of protein in each fraction. Fractions containing the desired protein were combined and dialyzed twice against 2 L of storage buffer (50 mM Tris-HCl, pH 8.0, 200 mM NaCl, 10% (v/v) glycerol). This procedure afforded yields of 0.27 mg/L for CHis6-tagged ClbPpep, and 0.21 mg/L for CHis6-tagged ClbPpep-S95A Biochemical Characterization of ClbPFL For all in vitro assays involving ClbPFL and ClbFL-S95A "Tris assay buffer" refers to a buffer composed of 50 mM Tris, 200 mM NaCl, 0.02% w/v DDM, pH 8.0. Likewise, "phosphate assay buffer" refers to 50 mM sodium phosphate, 200 mM NaCl, 0.02% w/v DDM, pH 8.0.

In vitro kinetics assays with ClbPFL (comparison of substrates 2, 3, and 4 using o-phthaldialdehyde derivatization): Assays were run in triplicate in 1.5 mL deep-well plates. ClbPFL-CHis10 was defrosted from −80° C. stocks on ice, then buffer exchanged into phosphate assay buffer using Zeba Spin 40K MWCO desalting columns (ThermoFisher Scientific). The enzyme was then diluted to 0.6 μM in phosphate assay buffer and 50 μL of this stock was deposited in the appropriate wells. The substrate of interest was prepared in a 2-fold dilution series in phosphate assay buffer. Reactions were initiated by the addition of 250 μL of substrate stock to each assay well to a final concentration of 0.1 μM ClbP, 12.5-200 μM substrate, 3% DMSO and incubated at 25° C. Reaction mixtures were pipetted briefly to mix. At each time point, 40 μL of each reaction was quenched by adding to 80 μL of cold methanol in the wells of a standard 96-well plate. Standard curves were prepared in triplicate by dissolving 1-100 μM L-alanine methyl ester in phosphate assay buffer with 0.1 μM ClbP and 3% DMSO and following the same quenching and sample preparation steps. Plates containing the quenched reaction samples were sealed and spun down at 3,880×g at 4° C. for 15 minutes. An opaque black 384-well flat-bottom plate was prepared by combining 3 mL of the derivatization reagent ("Phthaldialdehyde Reagent Solution, Incomplete", Millipore-Sigma) with 3 μL of β-mercaptoethanol and adding 50 μL of this mixture to each well for measurement. 50 μL of each supernatant from the quenched reactions and standard curves were then transferred to the appropriate wells, pipetted once to mix, and then fluorescence was immediately measured on a plate reader (Bio-Tek Synergy HTX multimode plate reader, measurement settings −360/40 nm excitation filter, 440/20 nm emission filter, detector gain: 35). Fluorescence was measured every 30 seconds for 10 minutes and the maximum value achieved for each well was used for calculations. Initial rate measurements are based on 3 independent replicates at each substrate concentration and 5 time points spaced 1 minute apart.

ClbP Activity Assays with Fluorogenic Probes

Figures 14A, 14B:
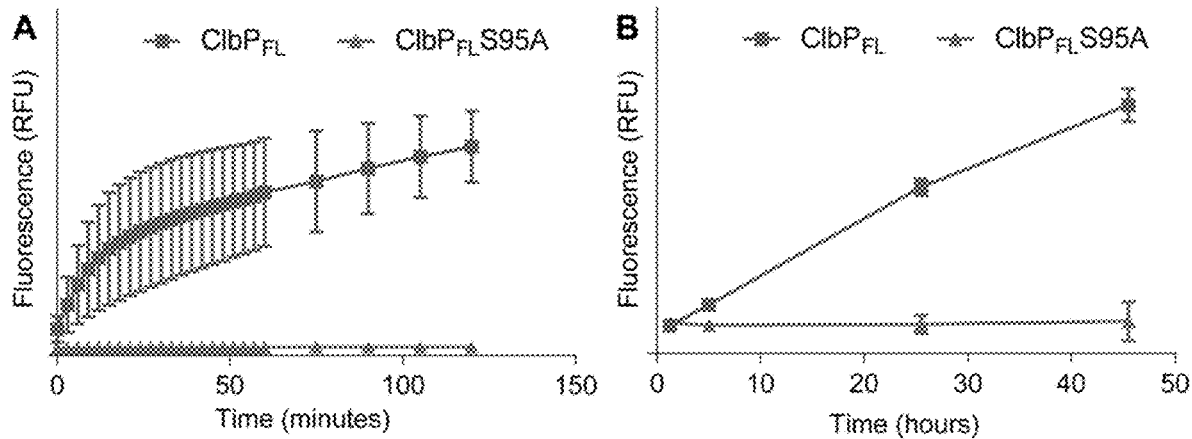
FIG. 14A depicts the detection of ClbP$_{FL}$ activity in vitro using probe 16.
FIG. 14B depicts the detection of ClbP$_{FL}$ activity in E. coli BL21 pET29b_ClbP$_{FL}$ using probe 17. Data points are averages of 6 biological replicates (error bars=1 SD).

Initial validation of probe 16 in vitro (FIG. 14A): Probe 16 was prepared as 10 mM stock solutions in DMSO and 1 μL of the appropriate stock was added to individual wells of an opaque black 96-well plate. ClbPFL-CHis10 and ClbPFL-S95A-CHis10 were defrosted from −80° C. stocks on ice, then diluted to 0.2 μM in Tris assay buffer. To initiate reactions, 99 μL of either ClbPFL or ClbPFL-S95A were transferred to the 96-well plate via multichannel pipette and mixed (n=6 for each enzyme). Activity was monitored by measuring the fluorescence of each well once per minute for 2 hours using a plate reader (Bio-Tek Synergy HTX multimode plate reader, measurement settings—360/40 nm excitation filter, 440/20 nm emission filter, detector gain: 35).

Validation of probes 16 and 17 whole-cells overexpressing ClbPFL (FIG. 3C and FIG. 14B): A 5 mL starter culture of *E. coli* BL21 pET-29b-ClbPFL or pET-29b-ClbPFL-595A was inoculated from a frozen stock and grown overnight at 37° C. in LB medium supplemented with 50 μg/mlkanamycin. Overnight cultures were diluted 1:100 into 5 mL M9 minimal medium supplemented with 1% w/v Casamino acids ("M9+CAA") containing 50 μg/mL kanamycin. Cultures were incubated at 37° C. with shaking at 175 rpm. Protein expression was induced with 500 μM IPTG at OD600=0.5 and cultures were moved to 15° C. and incubated with shaking at 175 RPM for ~4 h. The OD600 of each culture was measured again. Cultures were pelleted at 4000×g for 10 minutes at 4° C. and resuspended in enough fresh M9+CAA media (containing 50 μg/mL kanamycin and 500 μM IPTG) to normalize the OD600 to 0.5. Resuspended cultures were added to a black 96 well plate, 120 μL per well. Probe 16 or 17 was prepared in a master mix of 1 mM probe, 50 μg/mL kanamycin, and 500 μM IPTG in M9+CAA media. 30 μL of master mix was added to each well to achieve a final concentration of 200 μM probe (2% DMSO). Plates were incubated at room temperature in a plate reader overnight while taking fluorescence measurements at regular intervals (Bio-Tek Synergy HTX multimode plate reader, measurement settings—360/40 nm excitation filter, 440/20 nm emission filter, detector gain: 35).

Comparing activity of ClbPFL and ClbPpep in vitro (FIG. 3B): Probe 17 was prepared as a 10 mM stock solution in DMSO then diluted to 250 μM in standard Tris assay buffer, and 5 μL of this stock was added to each well of an opaque black 384-well flat-bottom plate. ClbPFL-CHis10 and ClbPFL-S95A-CHis10 were defrosted from −80° C. stocks on ice, then diluted to 0.125 μM in Tris assay buffer. Reactions were initiated by added 20 μL of either the ClbPFL or ClbPFL-S95A to the wells via multichannel pipette and pipetting once to mix (n=6 for each enzyme). Assays for ClbPpep and ClbPpep-S95A activity were conducted in parallel following the same procedure, but in buffers that did not contain DDM. All reactions contained 0.1 μM enzyme, 50 μM substrate, and 0.5% DMSO and were run at 25° C. Activity was monitored by measuring the fluorescence of each well once per minute for 2 hours using a plate reader (Bio-Tek Synergy HTX multimode plate reader, measurement settings—360/40 nm excitation filter, 440/20 nm emission filter, detector gain: 35).

Detection of ClbP activity in pks+ organisms (FIG. 4A): For anaerobic experiments, MEGA media 14 was autoclaved for 20 minutes at 120° C., sparged with sterile N2 for 1 hour, and equilibrated in a Coy vinyl anaerobic chamber (Coy Labs, Grass Lake, Mich.) overnight under a 95% N2/5% H2 atmosphere. All anaerobic experiments were performed in this environment. Note that the standard formulation of MEGA medium includes resazurin as a colorimetric oxygen indicator, but this was omitted to avoid interfering with the fluorescence signal. A 5 mL starter culture of *E. coli* BW25113 BACpks, BW25113 BAC vector, Nissle 1917, or CCR20¬ was inoculated from a frozen stock and grown overnight at 37° C. in MEGA medium under anaerobic conditions without shaking. Overnight cultures were diluted 1:100 into 1 mL of MEGA medium containing 100 μM 17 (added as a 10 mM stock in DMSO) in triplicate in a 1.5 mL 96-well plate. Cultures were incubated anaerobically at 37° C. At each time point, 100 μL of each culture was transferred to an opaque black 96-well plate, removed from the anaerobic chamber, and the fluorescence was measured immediately (Bio-Tek Synergy HTX multimode plate reader, measurement settings—360/40 nm excitation filter, 440/20 nm emission filter, detector gain: 35).

Figure 15:
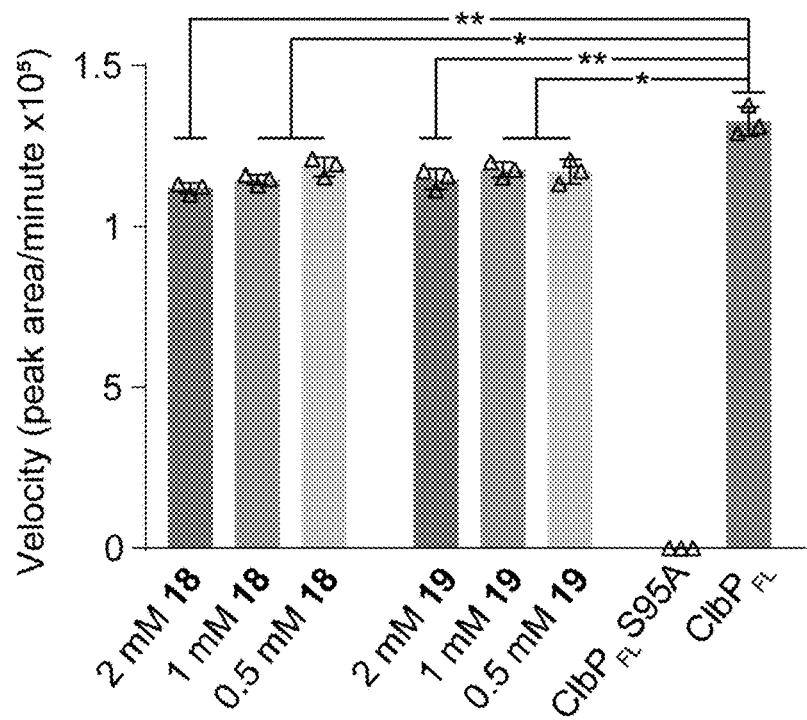
FIG. 15 depicts the cleavage of 2 by ClbP$_{FL}$ in vitro detected by LC-MS when treated with 18 or 19. Reaction velocities correspond to the increase in EIC peak area for the [M+H]⁺ ion of 20 (343.3597 m/z). Experiments were performed in triplicate at each concentration for each molecule (triangle represent individual replicates). Bars represent the slope of the linear fit of increase in the EIC peak area of 20 of over the first 10 minutes of the reaction of ClbP$_{FL}$ in vitro with 2. Error bars represent SD of the slope values. *:P<0.05; **:P<0.01; Student's two-tailed t test.
Figure 16:
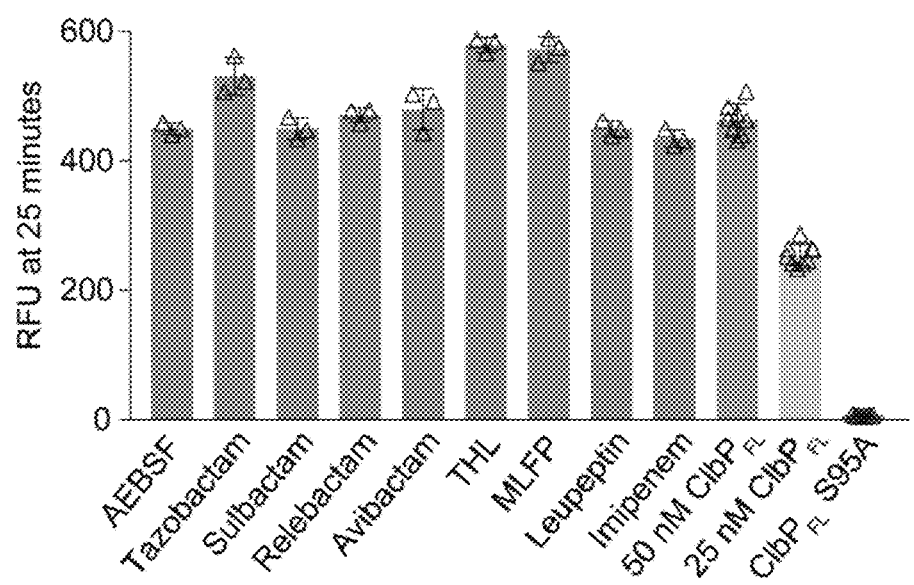
FIG. 16 depicts assessing inhibition of ClbP by other serine hydrolase inhibitors. ClbP$_{FL}$ was incubated with the indicated inhibitor for 1 hour before addition of probe 17 to assess changes in catalytic activity as described above. Abbreviations: AEBSF—4-(2-aminoethyl)benzenesulfonyl fluoride hydrochloride; THL—tetrahydrolipstatin; MLFP—methyl α-linolenyl fluorophosphonate). Error bars are SD, treatment n=3, controls n=9, 50 nM enzyme except where indicated.

Testing inhibition of ClbPFL by small molecules using LC-MS-based assay (FIG. 15): Boronic acids 18 (purchased from Sigma Aldrich) and 19 were prepared as 50 mM stocks in DMSO, while substrate 2 was prepared as a 10 mM stock in DMSO. ClbPFL-CHis10 was defrosted on ice from −80° C. stocks, diluted to 0.12 μM in Tris assay buffer, and incubated with the appropriate concentration of 18, 19, or DMSO (controls) for 1 hour at ambient temperature in order to allow for inhibitor binding. Separately, 300 μM 2 in Tris assay buffer was deposited in the wells of a 96-well plate (25 μL). Reactions were initiated by transferring 125 μL of the enzyme/inhibitor or enzyme/DMSO mix to the 96-well plate (final assay conditions: 0.1 μM enzyme, 50 μM substrate 2, 0-2 mM inhibitor, 4.5% DMSO, 25° C.). Time points were taken at 0, 5, and 10 minutes as described above (see "SAR study") and LC-MS samples were prepared in the same manner. For each condition, a reaction velocity was determined by measuring the increase in EIC peak area for the expected mass of the prodrug scaffold fragment (±5 ppm) independently across three replicates.

Chemical Synthesis Procedures and Characterization Data

Compounds 1, 2, 15, 20, and intermediate 29 were synthesized as previously described.[13,15] NMR spectra and high-resolution masses for all compounds were identical to those previously reported. Inhibitor 19 was provided as a gift from Professor Fabio Prati (Unimore, Via Università 4, 41121 Modena, Italy) and was prepared as previously described.[16] Its purity was confirmed by $^1$H NMR spectroscopy.

† Note on NMR spectra: For many of the substrates below which contain a D-asparagine residue, a peak annotated as a doublet of doublets is reported at or near 2.33 ppm with coupling constants of approximately J=15.3 and 8.1 Hz, a 1H integration, and an asymmetric splitting pattern. This peak is actually one of two peaks originating from the two diastereotopic protons on the β-carbon of the D-asparagine side chain. The other 1H proton signal overlaps with the DMSO-$d_6$ solvent residual for some substrates. When possible, $^1$H NMR spectra were recorded in $CDCl_3$ or $CD_3OD$ to avoid this issue, but many of these substrates are poorly soluble in anything other than DMSO. For several example substrates, 2D NMR spectroscopy experiments ($^1$H-$^{13}$C HSQC, HMBC or $^1$H-$^1$H COSY) were used to confirm that there is a second peak overlapping with the DMSO signal and that the connectivity is as described (see substrates 4, 6, 7, 12, 13, 16, and 17 for example spectra). The chemical shift and splitting patterns for these peaks are also in line with computational predictions for this peak. This overlap results in the total integration of the spectrum lacking 1 H when compared to the molecular formula. In all cases where this overlap occurs, the peak is denoted by a †.

General Procedure A: HATU Coupling of Amino Acids

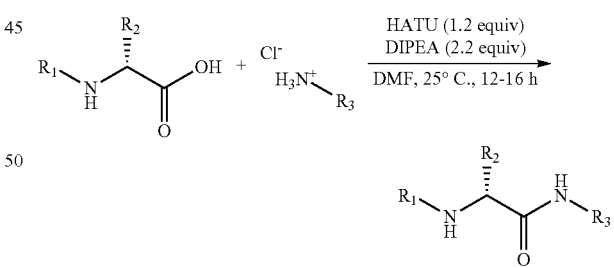

$R_1$ = Boc, Fmoc, or Acyl
$R_2$ = D-Asn, D-Asn(Trt), D-Asp(OBn)
$R_3$ = L-Ala(OMe), Gly(OMe), β-Ala(OMe)

To an oven-dried round bottom flask equipped with a stir bar was added a Boc-protected, Fmoc-protected, or N-acylated amino acid (1.0 equiv), the HCl-salt of the methyl ester-protected amino acid (1.2 equiv), and hexafluorophosphate azabenzotriazole tetramethyluronium (HATU, 1.2 equiv, Oakwood Chemicals or Chem-Impex International, Inc.) under $N_2$. Anhydrous N,N-dimethylformamide (DMF, 0.1-0.5 M) was added and the reaction mixture stirred at room temperature until all components were dissolved.

Diisopropylethylamine (DIPEA, 2.2 equiv) was added dropwise, and the reaction mixture was stirred at room temperature overnight. The reaction was quenched by the addition of 1 reaction volume of aqueous 1 M HCl. The reaction mixture was diluted with 5 reaction volumes of ethyl acetate (EtOAc) and the organic layer was washed with 1 M HCl. The aqueous layer was extracted a second time with ethyl acetate. The combined organic layers were washed with 5% aqueous LiCl, saturated aqueous sodium bicarbonate, water, and brine. The organic layer was dried over $Na_2SO_4$, filtered, and concentrated in vacuo to give the final product. The crude product was either used directly in the subsequent step or was purified as described for the individual compounds listed below.

General Procedure B: HATU Coupling of Dipeptides to Acyl Group

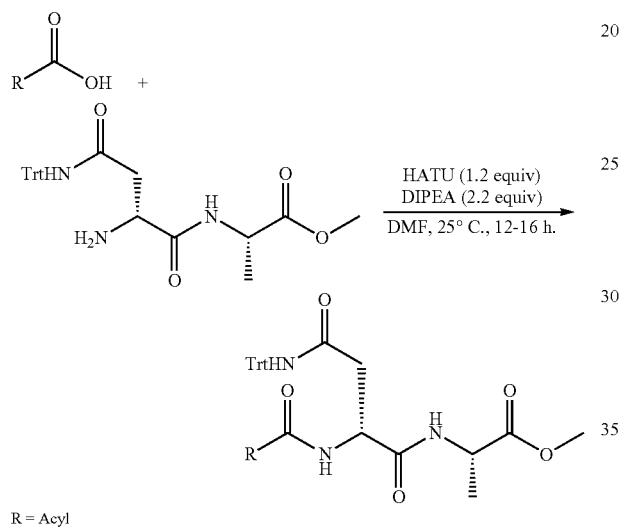

To an oven-dried round bottom flask equipped with a stir bar was added a dipeptide methyl ester (1.0 equiv), the appropriate carboxylic acid (1.2 equiv), and hexafluorophosphate azabenzotriazole tetramethyluronium (HATU, 1.2 equiv, Oakwood Chemicals or Chem-Impex International, Inc.) under $N_2$. Anhydrous DMF (0.1-0.5 M) was added and the reaction mixture was stirred at room temperature until all components were dissolved. DIPEA (2.2 equiv) was added dropwise, and the reaction mixture was stirred at room temperature overnight. The reaction was quenched by the addition of 1 reaction volume of aqueous 1 M HCl. The reaction mixture was then diluted with 5 reaction volumes of EtOAc and the organic layer was washed with 1 M HCl. The aqueous layer was extracted a second time with ethyl acetate. The combined organic layers were washed with 5% aqueous LiCl, saturated aqueous $NaHCO_3$, water, and brine. The organic layer was dried over $Na_2SO_4$ and concentrated in vacuo to give the crude product. The crude product was used directly in the subsequent step.

General Procedure C: Acyl Chloride Coupling

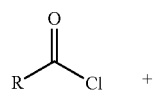

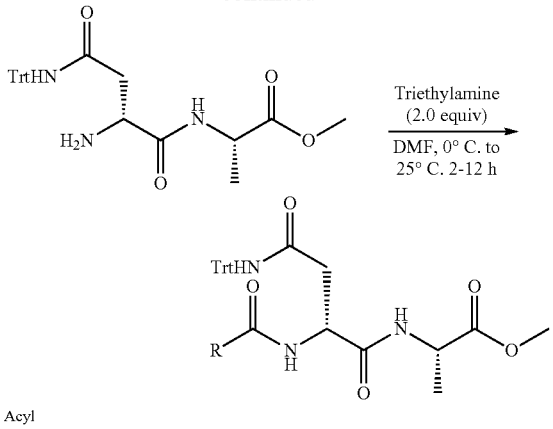

To an oven-dried round bottom flask equipped with a stir bar was added the dipeptide methyl ester (1.0 equiv) and anhydrous DMF (0.4 M) under dry $N_2$. Triethylamine (TEA, 2.0 equiv) was added and the mixture was subsequently cooled to 0° C. In a separate oven-dried round bottom flask, the acyl chloride (2.0 equiv) was diluted in anhydrous DMF (0.8 M) under dry $N_2$ and cooled to 0° C. The acyl chloride solution was added dropwise to the flask containing the dipeptide via syringe. The reaction mixture was warmed to room temperature and stirred for at least 2 hours and up to 12 hours. Work up conditions varied for each substrate and are described for the individual compounds listed below. The crude product was used directly in the subsequent step.

General Procedure D: Trityl Deprotection

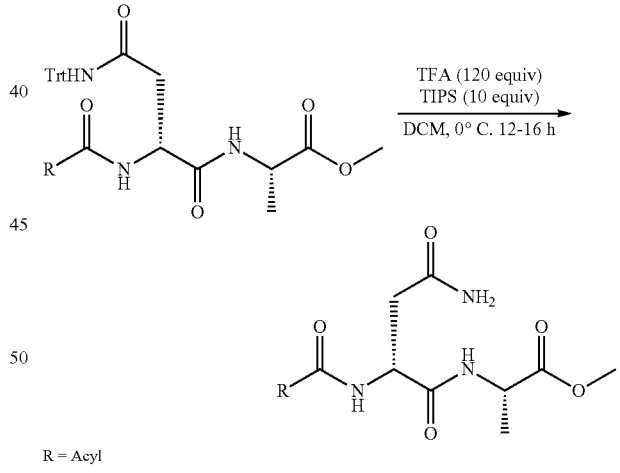

To a round bottom flask was added the trityl-protected peptide and dichloromethane (DCM, 0.05-0.2 M). Once the starting material was dissolved, the reaction mixture was cooled to 0° C. and triisopropylsilane (TIPS, 10 equiv) and trifluoroacetic acid (TFA, 120 equiv) were added. The flask was sealed and kept at 4° C. overnight. Toluene (1 reaction volume) was added, and the reaction mixture was concentrated in vacuo. This procedure was repeated twice more to remove any residual TFA. The crude residue was dissolved in DMSO and purified using preparative HPLC (conditions are specified for each substrate below).

General Procedure E: PyBOP Coupling

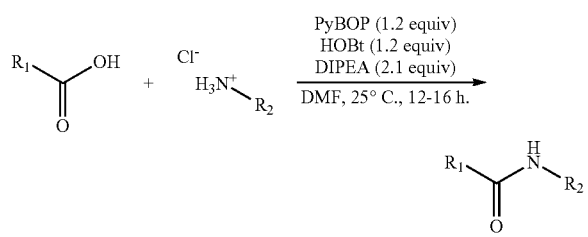

R1 = Boc-D-Gln, Boc-L-Asn pr Acyl
R2 = L-Ala(OMe) or dipeptide

To an oven-dried round bottom flask equipped with a stir bar was added a Boc-protected amino acid or carboxylic acid (1.0 equiv), the HCl-salt of the methyl ester-protected amino acid (1.0 equiv) and dry DMF (0.1-0.3 M). The starting materials were dissolved at room temperature and HOBt (Sigma Aldrich, 1.2 equiv) and PyBOP (Chem-Impex International, Inc) were added. The flask was then cooled to 0° C. and DIPEA (2.1 equiv) was added dropwise. The reaction mixture was warmed to room temperature overnight. The reaction mixture was then diluted with 5 reaction volumes of EtOAc or DCM and quenched by the addition of 1 reaction volume of aqueous 1 M HCl. The aqueous and organic layers were separated and the aqueous layer was extracted 2 more times with the same solvent (EtOAc or DCM). The combined organic layers were washed with saturated aqueous NaHCO$_3$ and brine. The organic layer was dried over Na$_2$SO$_4$, filtered, and then concentrated in vacuo. The crude product was either used directly in the subsequent step or was purified as described for the individual compounds listed below.

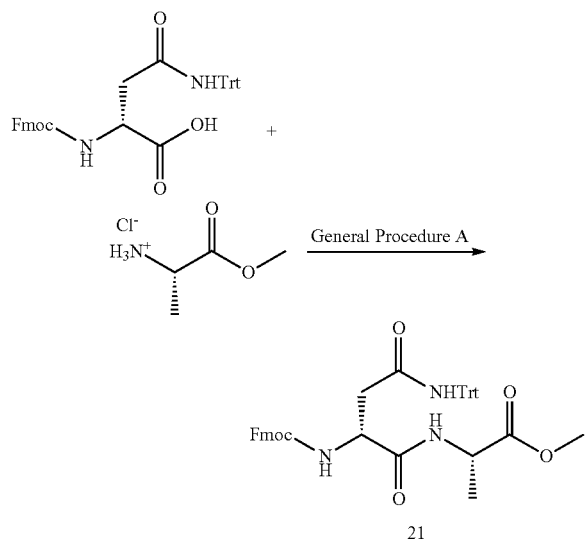

Dipeptide 21 was accessed by coupling Nα-Fmoc-Nγ-Trt-D-asparagine (Chem-Impex International, 2.13 g) and L-alanine methylester hydrochloride (Chem-Impex International, 547 mg) according to General Procedure A. This intermediate was purified by flash column chromatography (silica, isocratic 6:2:1 EtOAc:Hexanes:DCM) affording 21 as a white solid (2.2 g, 85% yield). $^1$H NMR (600 MHz, CDCl$_3$): δ (ppm)=7.76 (d, J=7.6 Hz, 2H), 7.58 (t, J=7.7 Hz, 2H), 7.40 (t, J=7.5 Hz, 2H), 7.34-7.22 (m, 15H)*, 7.19 (d, J=7.6 Hz, 6H), 6.90 (s, 1H), 6.40 (d, J=7.9 Hz, 1H), 4.57 (s, 1H), 4.46 (q, J=7.1 Hz, 1H), 4.44-4.38 (m, 1H), 4.35 (t, J=9.1 Hz, 1H), 4.21 (t, J=7.2 Hz, 1H), 3.71 (d, J=1.1 Hz, 3H), 3.21-3.03 (m, 1H), 2.59 (dd, J=15.7, 6.1 Hz, 1H), 1.35 (d, J=7.1 Hz, 3H). $^{13}$C NMR (400 MHz, DMSO-d$_6$): δ (ppm)=172.8, 171.1, 168.66, 155.6, 144.7, 143.8, 140.7, 128.6, 127.6, 127.4, 127.1, 126.3, 125.33, 125.28, 120.1, 69.4, 65.8, 51.9, 47.7, 46.7, 17.1‡. HRMS (ESI): calcd for C$_{42}$H$_{40}$N$_3$O$_6$ [M+H]$^+$, 682.2917; found, 682.2945.

*Additional 3H integration value due to overlap with solvent residual with expected 12H multiplet ‡ An additional $^{13}$C peak is predicted at a shift of 80.7 ppm, corresponding to the quaternary carbon of the trityl protecting group. This signal could not be detected, likely due to the poor signal produced by this nuclide and the limited solubility of 21.

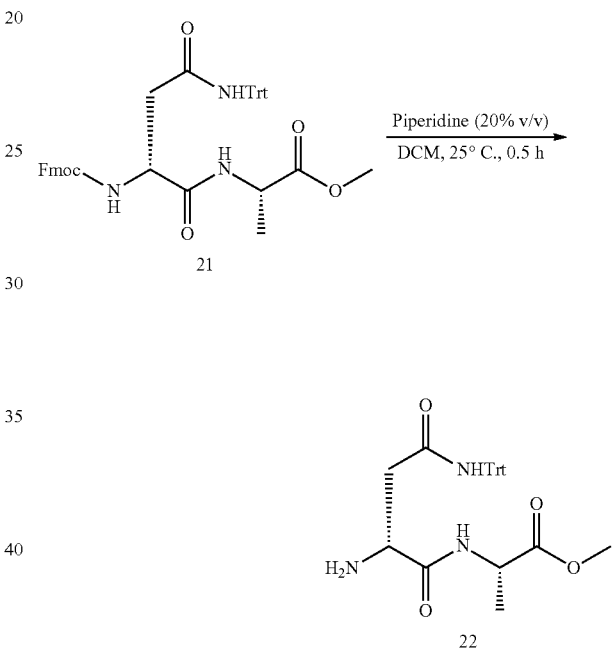

Fmoc-protected dipeptide 21 (105 mg) was dissolved in DCM (1.5 mL, 0.1 M) in a round bottom flask. Piperidine (0.38 mL) was added and the reaction mixture was stirred at room temperature under an atmosphere of N$_2$ for approximately 30 minutes until thin-layer chromatography (TLC) indicated that the reaction was complete. The reaction mixture was diluted with 5 reaction volumes of DCM and then quenched by the addition of 5 reaction volumes of saturated aqueous ammonium chloride. The aqueous layer was extracted again with DCM, and the combined organic layers were washed with saturated aqueous NH$_4$Cl, NaHCO$_3$, and brine. The organic layer was dried over Na$_2$SO$_4$, filtered, and then concentrated in vacuo. The resulting residue was purified by flash column chromatography (gradient from CHCl$_3$ to CHCl$_3$:MeOH 9:1 on neutral alumina) affording 22 as a thick clear oil (73 mg, 70% yield). $^1$H NMR (500 MHz, CDCl$_3$): δ (ppm)=7.82 (d, J=7.6 Hz, 1H), 7.59 (s, 1H), 7.36-7.18 (m, 17H), 4.47 (quint, J=7.3 Hz, 1H), 3.71 (s, 3H), 3.66 (dd, J=8.1, 4.1 Hz, 1H), 2.73 (dd, J=15.1, 4.1 Hz, 1H), 2.62 (dd, J=15.1, 8.2 Hz, 1H), 1.38 (d, J=7.2 Hz, 3H). $^{13}$C NMR (400 MHz, DMSO-d$_6$): δ (ppm)=173.2*, 172.4, 168.7, 168.6*, 167.8, 144.6§, 144.4, 144.38*, 143.7§, 128.6*, 128.5, 128.2§, 127.9§, 127.54, 127.47*, 127.0§, 126.5, 126.4*, 69.64, 69.56*, 52.3*, 52.1, 47.9, 47.8*, 36.2, 17.1, 17.0*.‡ HRMS (ESI): calcd for $C_{27}H_{30}N_3O_4$ [M+H]$^+$, 460.2236; found, 460.2233.

\* denotes a rotamer

§ denotes a peak arising from residual dibenzofulvene, the side product of Fmoc-deprotection ‡ An additional peak is predicted at a shift of 80.7 ppm, corresponding to the quaternary carbon of the trityl protecting group. This signal could not be detected, likely due to the poor signal produced by this nuclide.

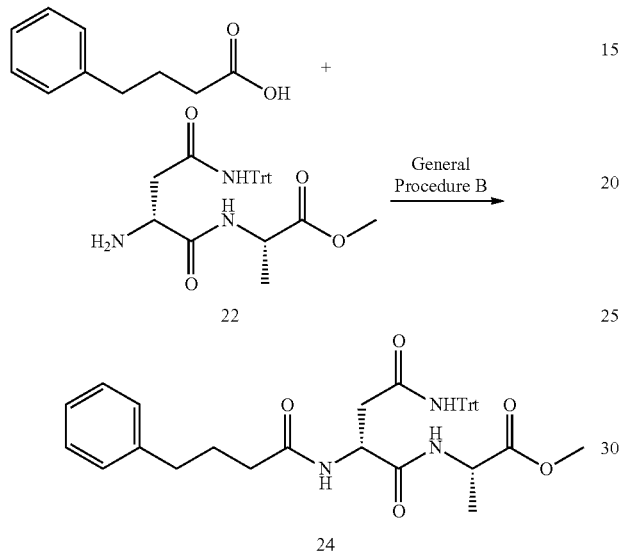

Dipeptide 22 (122 mg) was coupled to 4-phenylbutanoic acid (48 mg) according to General Procedure B. The product 24 was isolated as a white solid (145 mg, 90% yield). Crude 24 was used in the next step of the synthesis (trityl deprotection) without further purification.

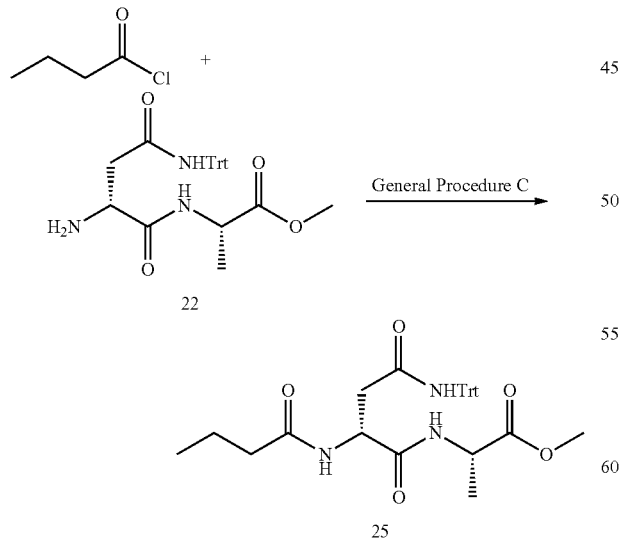

Dipeptide 22 (172 mg) was coupled to butyryl chloride (77 μL) following General Procedure C. The reaction mixture was diluted with 5 reaction volumes of DCM and washed with 5 reaction volumes of aqueous 0.1 M HCl. The aqueous layer was extracted again with DCM and the combined organic layers were washed with saturated aqueous NaHCO$_3$, water, and brine. The organic layer was dried over Na$_2$SO$_4$ and was then concentrated in vacuo to afford crude 25 as a light-yellow solid (101 mg, 51% yield). This material was used in the next step of the synthesis (trityl deprotection) without further purification.

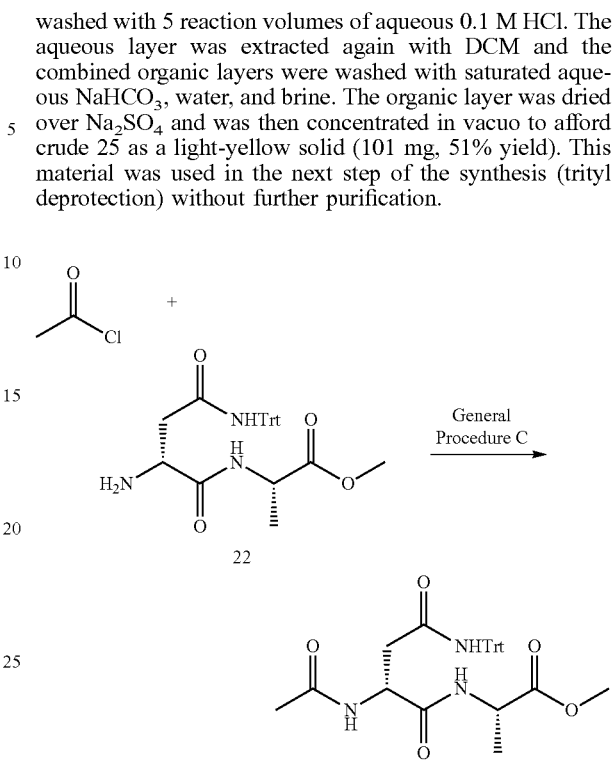

Dipeptide 22 (53 mg) was coupled to acetyl chloride (9 μL) following General Procedure C. The reaction mixture was diluted with EtOAc and washed with aqueous 0.1 M HCl. The aqueous layer was extracted again with EtOAc, and the combined organic layers were washed with saturated aqueous NaHCO$_3$, water, and brine. The organic layer was dried over Na$_2$SO$_4$ and was then concentrated in vacuo to afford crude 26 as a white solid (56.4 mg, 97% yield). Crude 26 was used in the next step of the synthesis (trityl deprotection) without further purification.

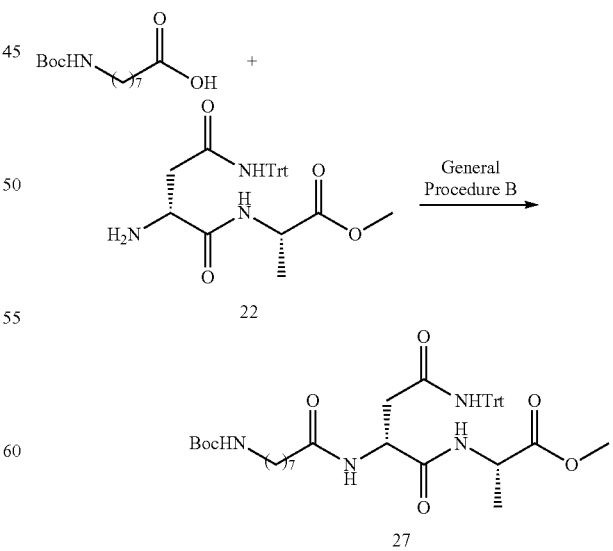

Dipeptide 22 (50 mg) was coupled to 8-aminocaproic acid (28.2 mg) following General Procedure B. The crude product, 27, was isolated as an off-white solid (yield reported for next step). Crude 27 was used in the next step of the synthesis (trityl deprotection) without further purification.

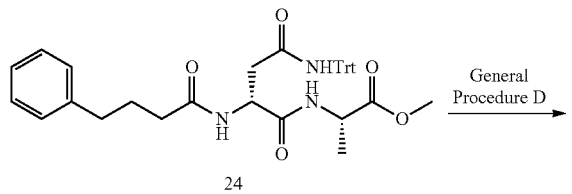

24 was deprotected to afford 3 according to General Procedure D. The initial product of the deprotection was a waxy off-white solid. This solid was dissolved in a minimal volume of DMSO and purified by preparative HPLC following the procedure described above. Fractions containing product were pooled and concentrated in vacuo to afford 3 as a white solid (38.2 mg, 57.9% yield over two steps). $^1$H NMR (500 MHz DMSO-$d_6$): δ (ppm)=8.10 (d, J=7.3 Hz, 1H), 7.97 (d, J=8.1 Hz, 1H), 7.31-7.14 (m, 6H), 6.86 (s, 1H), 4.60 (dt, J=8.1, 5.8 Hz, 1H), 4.25 (quint, J=7.2 Hz, 1H), 3.59 (s, 3H), 2.55 (t, J=7.5 Hz, 2H), 2.33† (dd, J=15.3, 8.1 Hz, 1H), 2.13 (t, J=7.4 Hz, 2H), 1.78 (quint, J=7.5 Hz, 2H), 1.25 (d, J=7.3 Hz, 3H). $^{13}$C NMR (500 MHz, DMSO-$d_6$): δ (ppm)=δ 172.8, 171.9, 171.2, 171.0, 141.9, 128.3, 128.2, 125.7, 51.8, 49.4, 47.6, 37.3, 34.7, 34.5, 27.1, 17.1. FIRMS (ESI): calcd for $C_{18}H_{26}N_3O_5$ [M+H]$^+$, 364.1872; found, 364.1870. $[α]_D^{22}$=+7.4° (c=0.84, DMSO).

† see "Note on NMR spectra" at the beginning of this section

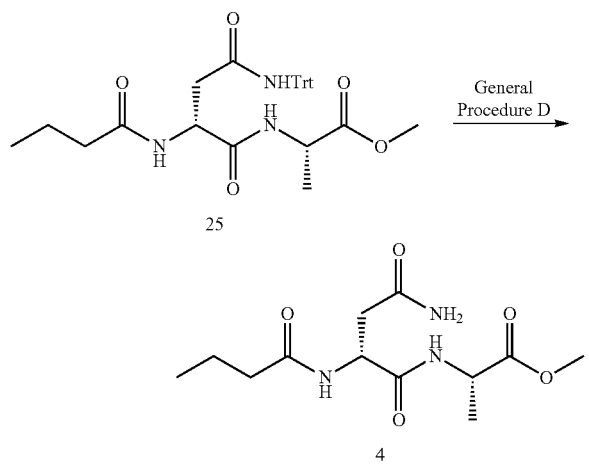

25 was deprotected to afford 4 according to General Procedure D. The initial product of the deprotection was an off-white solid. This solid was dissolved in a minimal volume of DMSO and purified by preparative HPLC using the following gradient conditions: 10% Solvent A for 2 minutes, gradient to 95% Solvent A over 7 minutes, hold at 95% Solvent A for 4 minutes, gradient to 10% solvent A over 1 minute, hold at 10% solvent A for 2 minutes (solvent A: HPLC-grade acetonitrile+0.1% formic acid; solvent B: water+0.1% formic acid; flow rate: 10 mL/minute; injection volume: 200 to 400 μL). Fractions were pooled and concentrated in vacuo to afford 4 as a white solid (30 mg, 27% yield over two steps). $^1$H NMR (600 MHz DMSO-$d_6$): δ (ppm)=8.12 (d, J=7.3 Hz, 1H), 8.01 (d, J=8.0 Hz, 1H), 7.29 (s, 1H), 6.85 (s, 1H), 4.59 (dt, J=8.1, 5.8 Hz, 1H), 4.25 (quint, J=7.2 Hz, 1H), 3.61 (s, 3H), 2.48 (dd, J=15.2, 5.9 Hz, 1H), 2.34 (dd, J=15.2, 5.9 Hz, 1H), 2.08 (t, J=7.3 Hz, 2H), 1.50 (sext, 2H), 1.25 (d, J=7.2 Hz, 3H), 0.85 (t, J=7.4 Hz, 3H). $^{13}$C NMR (500 MHz, DMSO-$d_6$) δ=172.8, 172.0, 171.3, 171.0, 51.9, 49.4, 47.6, 37.4, 37.1, 18.6, 17.1, 13.5. HRMS (ESI): calcd for $C_{12}H_{22}N_3O_5$ [M+H]$^+$, 288.1559; found, 288.1546. $[α]_D^{23}$=+23.4° (c=1.0, DMSO).

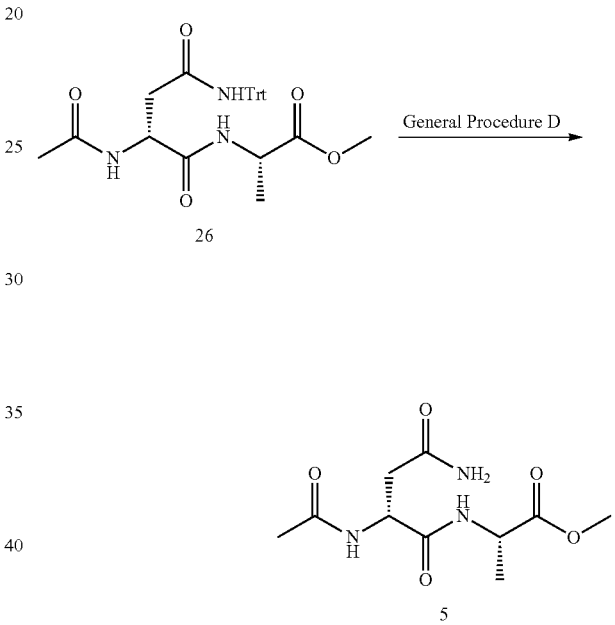

26 was deprotected to afford 5 according to General Procedure D. The initial product of the deprotection was an off-white solid. This solid was dissolved in a minimal volume of DMSO and purified by preparative HPLC using the following gradient conditions: 5% Solvent A for 2 minutes, gradient to 40% Solvent A over 8 minutes, gradient to 95% Solvent A over 5 minutes, hold at 95% Solvent A for 2 minutes, gradient to 5% solvent A over 1 minute, hold at 5% solvent A for 2 minutes (solvent A: HPLC-grade acetonitrile+0.1% formic acid; solvent B: water+0.1% formic acid; flow rate: 6 mL/minute; injection volume: 200 to 400 μL). Fractions were pooled and concentrated in vacuo to afford 5 as a white solid (24 mg, 17% yield over two steps). $^1$H NMR (500 MHz DMSO-$d_6$): δ (ppm)=8.17 (d, J=7.3, 1H), 8.04 (d, J=7.6 Hz, 1H), 7.29 (s, 1H), 6.87 (s, 1H), 4.57 (dt, J=8.0, 5.7 Hz, 1H), 4.24 (quint, J=7.2 Hz, 1H), 3.61 (s, 3H), 2.47 (dd, J=15.5, 6.1 Hz, 1H), 2.32 (dd, J=15.2, 8.1 Hz, 1H), 1.83 (s, 3H), 1.25 (d, J=7.2 Hz, 3H). $^{13}$C NMR (500 MHz, DMSO-$d_6$) δ=172.8, 171.3, 171.0, 169.2, 51.9, 49.5, 47.6, 37.5, 22.6, 17.01. HRMS (ESI): calcd for $C_{10}H_{18}N_3O_5$ [M+H]$^+$, 260.1246; found, 260.1235. $[α]_D^{21.5}$=+15.0° (c=0.2, DMSO).

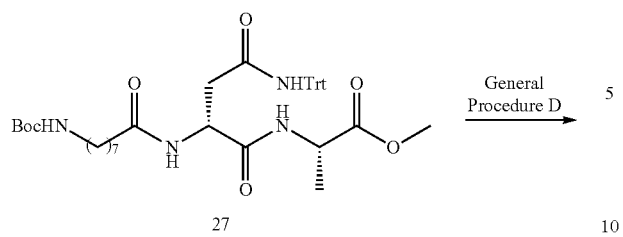

27

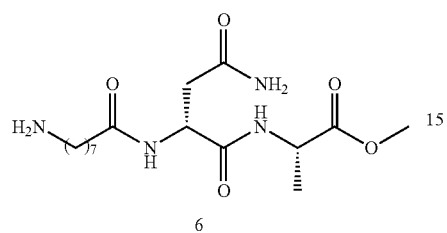

6

27 was deprotected to afford 6 according to General Procedure D. The initial product of the deprotection was an off-white solid. This solid was dissolved in a minimal volume of DMSO and purified by preparative HPLC using the following gradient conditions: 5% Solvent A for 2 minutes, gradient to 45% Solvent A over 7 minutes, hold for 2 minutes, gradient to 60% solvent A over 2 minutes, hold for 3 minutes, gradient to 95% solvent A over 2 minutes, hold for 1 minute, gradient to 5% solvent A over 1 minute, hold for 3 minutes (solvent A: HPLC-grade acetonitrile+ 0.1% formic acid; solvent B: water+0.1% formic acid; flow rate: 7 mL/minute; injection volume: 200 to 400 μL). Fractions were pooled and concentrated in vacuo to afford 6 as a white solid (34 mg, 40% yield over two steps). $^1$H NMR (400 MHz DMSO-$d_6$): δ (ppm)=8.20-7.94 (m, 2H), 7.32 (s, 1H), 6.86 (s, 1H), 4.57 (d, J=7.1 Hz, 1H), 4.24 (p, J=7.3 Hz, 1H), 3.61 (s, 3H), 2.79-2.65 (m, 2H), 2.34† (dd, J=15.8, 7.9 Hz, 1H), 2.10 (t, J=7.4 Hz, 2H), 1.59-1.40 (m, 4H), 1.40-1.05 (m, 11H). $^{13}$C NMR (500 MHz, DMSO-$d_6$). δ=172.8, 172.1, 171.3, 171.1, 51.9, 49.5, 47.6, 37.4, 35.1, 28.3, 27.8, 25.8, 25.0, 17.1. HRMS (ESI): calcd for $C_{16}H_{31}N_4O_5$ [M+H]$^+$, 359.2294; found, 359.2278. $[\alpha]_D^{21.5}$=+18.5° (c=0.57, DMSO).

14 distinct $^{13}$C signals are observed for this substrate (16 are expected), which is likely due to the close overlap of peaks from the acyl chain in the 25-29 ppm range. 2D HSQC data is included for this substrate in the next section.

† See "Note on NMR spectra" at the beginning of this section

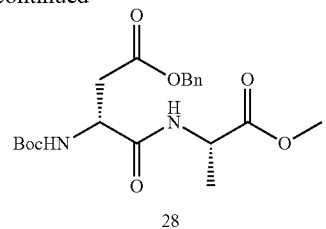

28

Dipeptide 28 was assembled according to General Procedure A using N-Boc-D-aspartic acid 4-benzyl ester (Oakwood Chemicals, 500 mg) and L-alanine methylester hydrochloride (Chem-Impex International, 238 mg). Crude 28 was isolated as a solid after work-up and purified by flash chromatography (silica, EtOAc:Hexanes 50:50 to 80:20) affording 28 as a clear, viscous oil (240 mg, 38% yield). $^1$H NMR (400 MHz, DMSO-$d_6$): δ (ppm)=8.19 (d, J=7.4 Hz, 1H), 7.45-7.25 (m, 5H), 7.06 (d, J=8.5 Hz, 1H), 5.08 (s, 2H), 4.38 (dt, J=8.5, 5.4 Hz, 1H), 4.26 (quint, J=7.2 Hz, 1H), 3.61 (s, 3H), 2.76 (dd, J=16.0, 5.4 Hz, 1H), 2.60 (dd, J=16.1, 8.7 Hz, 1H), 1.38 (s, 9H), 1.24 (d, J=7.2 Hz, 3H). $^{13}$C NMR (500 MHz, DMSO-$d_6$): δ (ppm)=172.7, 170.4, 170.0, 155.1, 136.0, 128.3, 127.9, 127.8, 78.4, 65.6, 51.8, 50.6, 47.6, 36.4, 28.1, 17.1. HRMS (ESI): calcd for $C_{20}H_{29}N_2O_7$ [M+H]$^+$, 409.1975; found, 409.1993.

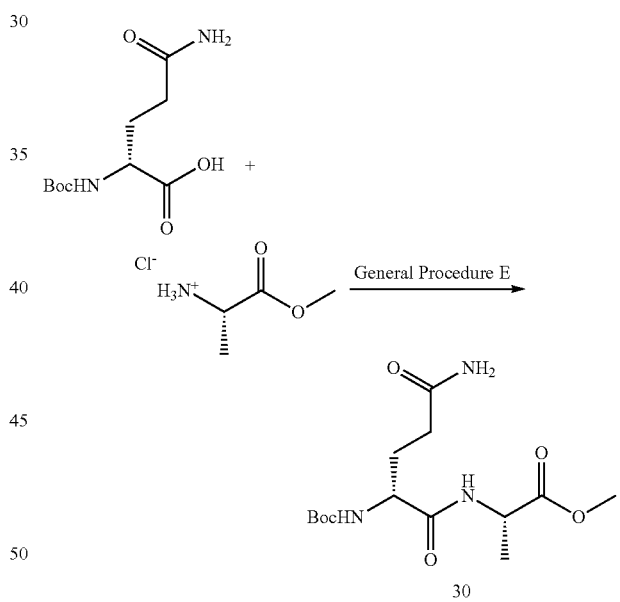

30

Dipeptide 30 was assembled according to General Procedure E using N-Boc-D-glutamine (185 mg) and L-alanine methylester hydrochloride (105 mg). The coupling was carried out at a concentration of 0.1 M N-Boc-D-glutamine and worked up using EtOAc to afford crude 30 as a viscous, colorless oil containing residual tripyrrolidinophosphine oxide, see note below* (127.2 mg, ~20% pure based on NMR, actual yield=25.5 mg of 30, 10% yield). $^1$H NMR (400 MHz, CDCl$_3$): δ (ppm)=7.33 (br s, 1H), 6.95 (br s, 1H), 6.02 (br s, 1H), 5.62 (br s, 1H), 4.49 (quint, J=7.2 Hz, 1H), 4.16 (br s, 1H), 3.68 (s, 3H), 3.19-3.07* (m, 56H), 2.42 (m, 1H), 2.36-2.24 (m, 1H), 2.14-1.85 (m, 2H), 1.79* (m, 56H), 1.44-1.33 (m, 12H)‡. $^{13}$C NMR (400 MHz, CDCl$_3$): δ (ppm)=175.9, 173.3, 171.2, 156.0, 77.4, 52.4, 48.3, 48.1, 46.7*, 31.8, 31.4, 28.4, 26.4*, 17.9. HRMS (ESI): calcd for $C_{14}H_{26}N_3O_6$ [M+H]$^+$, 332.1822; found, 332.1825.

*Tripyrrolidinophosphine oxide is a known side product of PyBOP coupling reactions. This material is difficult to remove but did not interfere with the next reaction and was removed in a subsequent purification step.

‡Predicted overlap of 9H singlet (Boc group) and 3H triplet (alanine β-methyl group)

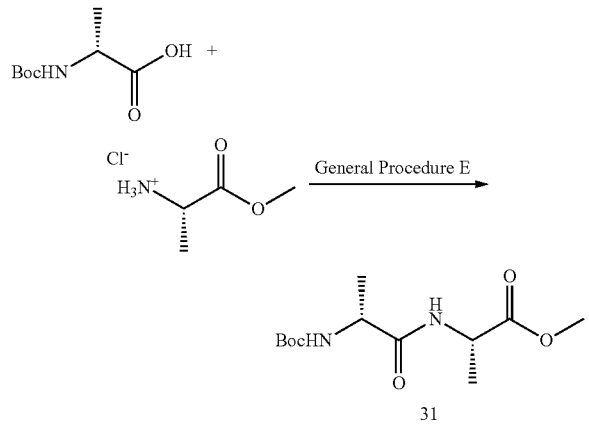

Dipeptide 31 was assembled according to General Procedure E using N-Boc-D-alanine (142 mg) and L-alanine methylester hydrochloride (105 mg). The reaction was worked up in EtOAc to afford 31 as a viscous, colorless oil containing residual tripyrrolidinophosphine oxide, see note below* (283.7 mg, 58% pure based on NMR; actual yield=163.6 mg of 31, 79% yield). $^1$H NMR (400 MHz, CDCl$_3$): δ (ppm)=6.94 (br s, 1H), 5.19 (br s, 1H), 4.49 (quint, J=7.4 Hz, 1H), 4.06 (q, J=7.2 Hz, 1H), 3.68 (s, 3H), 3.19-3.07* (m, 8H), 1.79* (m, 8H), 1.39 (s, 9H), 1.35 (d, J=7.3 Hz, 3H), 1.30 (d, J=7.1 Hz, 3H). $^{13}$C NMR (400 MHz, CDCl$_3$): δ (ppm)=173.3, 172.5, 155.6, 80.1, 52.4, 50.0, 48.0, 46.5*, 28.3, 26.4*, 18.3, 18.2. HRMS (ESI): calcd for $C_{12}H_{23}N_2O_5$ [M+H]$^+$, 275.1607; found, 275.1611.

*Denotes a peak originating from tripyrrolidinophosphine oxide, a known side product of the PyBOP coupling used here. This contaminant is difficult to remove but does not interfere with the next reaction and was removed in a subsequent step.

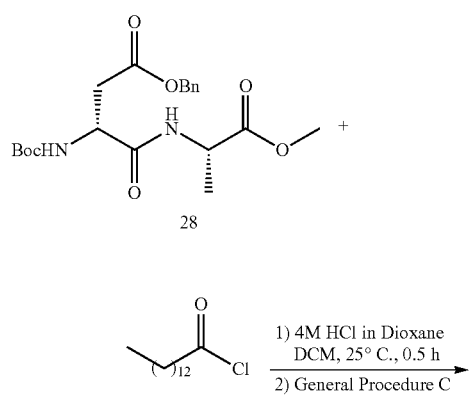

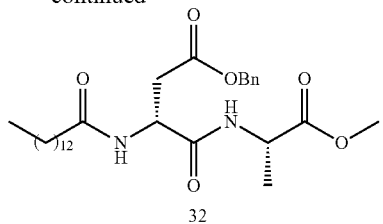

To a round bottom flask equipped with a stir bar was added 28 (240 mg, 1.0 equiv), 5.1 mL of anhydrous DCM, and 3.7 mL of 4 M HCl in dioxane. The reaction mixture was stirred at room temperature until TLC indicated the Boc deprotection was complete. The reaction mixture was then sparged with N$_2$ for 10 minutes and concentrated in vacuo to afford the amine hydrochloride salt as a thick, clear oil. This oil was dissolved in anhydrous DMF (3.9 mL) and coupled to myristoyl chloride following General Procedure C. After stirring at room temperature overnight, 32 was precipitated out of the reaction mixture by the addition of 5% aqueous LiCl (10 mL). The precipitate was filtered and washed with saturated aqueous NaHCO$_3$, 0.1 M HCl, water, and cold diethyl ether (Et$_2$O). Some residual myristic acid produced by hydrolysis of the acyl chloride remained and removal was attempted using flash chromatography (C18 functionalized silica, CombiFlash RediSepRf system, Teledyne ISCO, Lincoln Nebr.) eluting in water/acetonitrile. This method was unable to fully remove the residual myristic acid despite trying a variety of linear gradient conditions and the product was used in the next step without further purification (227 mg, 64% pure based on NMR; actual yield=145.3 mg of 32, 48% yield). $^1$H NMR (600 MHz DMSO-d$_6$): δ (ppm)=8.27 (d, J=7.2 Hz, 1H), 8.11 (d, J=8.5 Hz, 1H), 7.47-7.29 (m, 5H), 5.06 (s, 2H), 4.71 (td, J=8.3, 5.8 Hz, 1H), 4.24 (p, J=7.3 Hz, 1H), 3.60 (s, 3H), 2.77 (dd, J=15.8, 5.8 Hz, 1H), 2.58 (dd, J=15.9, 8.4 Hz, 1H), 2.18* (t, J=7.4 Hz, 2H), 2.07 (t, J=7.4 Hz, 2H), 1.54-1.40* (m, 5H), 1.29-1.16* (m, 45H), 0.89-0.81* (m, 6H). $^{13}$C NMR (500 MHz, DMSO-d$_6$) δ (ppm)=173.1, 172.7, 170.6, 170.3, 136.5, 128.8, 128.4, 128.2, 66.1, 52.3, 49.4, 48.1, 36.9, 35.6, 31.8, 29.5, 29.5, 29.4, 29.3, 29.2, 29.1, 29.0, 28.9, 25.6, 22.6, 17.5, 14.4. HRMS (ESI): calcd for $C_{29}H_{47}N_2O_6$ [M+H]$^+$, 519.3434; found, 519.3446.

*Peaks originating from or overlapping with peaks from myristic acid

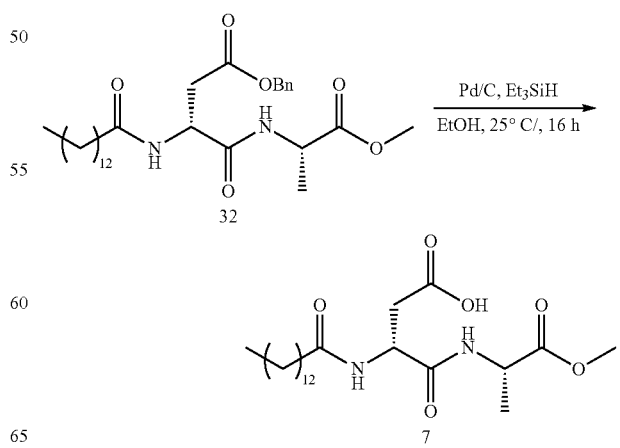

To a round bottom flask equipped with a stir bar was added palladium on carbon (15 mg, 10% by weight) under N$_2$ and water (0.5 mL). Acyl dipeptide 32 (80 mg, 1.0 equiv) was suspended in ethanol (EtOH, 10 mL) in a separate vial and sonicated briefly. The slurry of 32 was added to the reaction flask and residual slurry was washed out of the vial using an additional 2 mL of ethanol and added to the reaction flask. The reaction mixture was flushed with N$_2$ while stirring for 10 minutes. Triethylsilane (246 μL, 10.0 equiv) was added dropwise, and gas evolution was observed. The reaction mixture was stirred at room temperature overnight, filtered over Celite to remove the catalyst, and the filtrate was concentrated in vacuo. Isopropanol (10 mL) was added and the reaction mixture concentrated in vacuo again. The process was repeated 2 additional times. At this point, the product was a viscous oil with some solids present. The residue was triturated with cold hexanes and filtered to isolate 7 as a white solid (71 mg, quantitative yield). This material was then dissolved in a minimum volume of DMSO and purified by preparative HPLC according to the procedure described in the General Materials and Methods to afford 7 as an off-white solid (58 mg, 82% yield). $^1$H NMR (600 MHz DMSO-d$_6$): δ (ppm)=12.25 (br s, 1H), 8.15 (d, J=7.2 Hz, 1H), 8.03 (d, J=8.2 Hz, 1H), 4.60 (dt, J=8.1, 6.1 Hz, 1H), 4.25 (quint, J=7.3 Hz, 1H), 3.61 (s, 3H), 2.62 (dd, J=16.7, 6.1 Hz, 1H), 2.43 (dd, J=16.3, 7.9 Hz, 1H), 2.09 (t, J=7.4 Hz, 2H), 1.52-1.41 (m, 2H), 1.31-1.17 (m, 23H), 0.85 (t, J=7.0 Hz, 3H). $^{13}$C NMR (400 MHz, DMSO-d$_6$) δ (ppm)=172.7, 172.3, 171.2*, 170.6, 51.8, 49.1, 47.6, 36.4, 35.2, 31.3, 29.05, 29.03, 29.01, 28.9, 28.8, 28.7, 28.6, 25.2, 22.1, 17.1, 13.9. HRMS (ESI): calcd for C$_{22}$H$_{41}$N$_2$O$_6$ [M+H]$^+$, 429.2965; found, 429.2958. [α]$_D^{22}$=+13.2° (c=0.63, DMSO).

*Low signal intensity in 1D $^{13}$C-NMR, but visible in the HMBC spectrum of this compound (see spectra below)

21 distinct $^{13}$C signals are observed for this substrate (22 are expected), which is likely due to the close overlap of peaks from the myristoyl group in the 28.5-29 ppm range.

and trifluoroacetic acid (2.5 mL) was added dropwise. The reaction was stirred at 0° C. until TLC indicated the Boc deprotection reaction was complete (approximately 15 minutes). Anhydrous toluene (5 mL) was added and the reaction mixture concentrated in vacuo. An additional 5 mL of toluene was added, and the reaction mixture concentrated again to remove residual TFA. To this flask was added DMF, myristic acid, HOBt, and PyBOP according to General Procedure E. The coupling was carried out at a concentration of 0.1 M 29 and worked up using EtOAc. The crude product was isolated as a viscous, colorless oil which was subsequently purified by preparative HPLC according to the procedure described in the Materials and Methods above herein to afford 8 as an off-white solid (40 mg, 18% yield over two steps). $^1$H NMR (600 MHz DMSO-d$_6$): δ (ppm)=8.15 (d, J=7.2 Hz, 1H), 7.93 (d, J=8.0 Hz, 1H), 7.25 (s, 1H), 6.85 (s, 1H), 4.55 (dt, J=8.3, 4.9 Hz, 1H), 4.22 (quint, J=7.3 Hz, 1H), 3.59 (s, 3H), 2.46 (dd, J=15.5, 5.1 Hz, 1H), 2.34 (dd, J=15.4, 8.7 Hz, 1H), 2.07 (t, J=7.5 Hz, 2H), 1.45 (m, 2H), 1.30-1.15 (m, 23H), 0.88-0.79 (m, 3H). $^{13}$CNMR (400 MHz, DMSO-d$_6$) δ (ppm)=172.9, 172.2, 171.4* 171.3, 51.8, 49.4, 47.6, 37.3, 35.2, 31.3, 29.05, 29.03, 29.00, 28.9, 28.8, 28.7, 28.6, 25.2, 22.1, 16.9, 14.0. HRMS (ESI): calcd for C$_{22}$H$_{42}$N$_3$O$_5$ [M+H]$^+$, 428.3124; found, 428.3112. [α]$_D^{22}$=−8.1° (c=0.5, DMSO).

*Low signal intensity in 1D $^{13}$C-NMR, but visible in the HMBC spectrum of this compound 21 distinct $^{13}$C signals are observed for this substrate (22 are expected), which is likely due to the close overlap of peaks from the myristoyl group in the 28.5-29 ppm range.

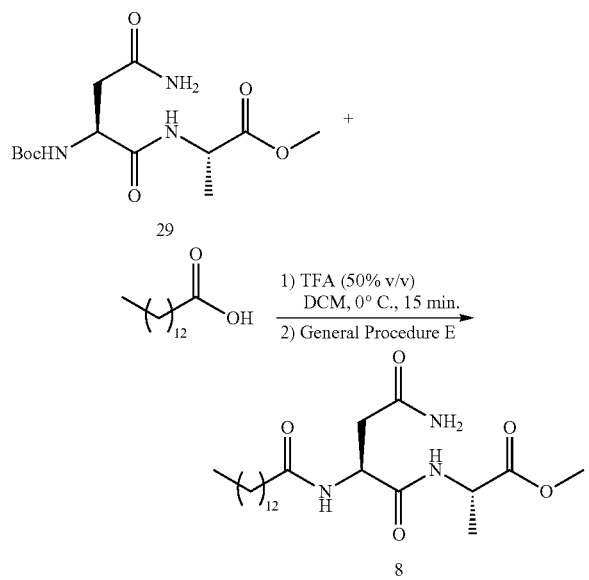

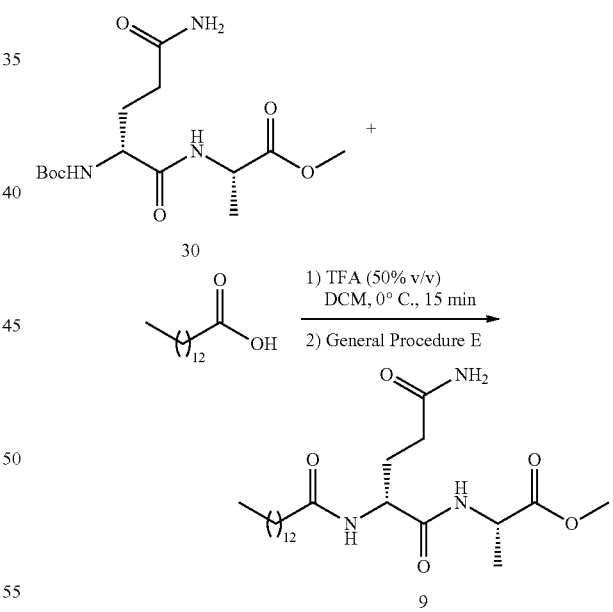

Compound 9 was prepared from compound 30 (270 mg) following the same procedure as described for the preparation of compound 7. Crude 9 was obtained as a clear viscous oil (150 mg, 42% crude yield) which was dissolved in DMSO and purified by preparative HPLC as described in the General Materials and Methods to afford pure 9 as a white solid (71 mg, 20% yield over two steps). $^1$H NMR (500 MHz DMSO-d$_6$): δ (ppm)=8.27 (d, J=7.3 Hz, 1H), 7.88 (d, J=8.3 Hz, 1H), 7.25 (s, 1H), 6.74 (s, 1H), 4.27 (m, 2H), 3.62 (s, 3H), 2.11 (t, J=7.6 Hz, 2H), 2.05 (t, J=8.4 Hz, 2H), 1.88-1.61

To an oven-dried round bottom flask was added intermediate 29 (prepared as previously described,$^{13}$ 163 mg, 1.0 equiv) and DCM (2.5 mL). The mixture was cooled to 0° C.

(m, 2H), 1.53-1.42 (m, 2H), 1.26 (m, 23H), 0.86 (t, J=6.7 Hz, 3H). $^{13}$C NMR (500 MHz, DMSO-d$_6$): δ (ppm)=173.6, 172.8, 172.1, 171.3, 51.8, 47.4, 35.2, 33.7, 31.4, 31.3, 29.04, 29.01, 28.96, 28.90, 28.8, 28.71, 28.7, 28.5, 28.2, 25.2, 22.1, 17.1, 13.9. HRMS (ESI): calcd for C$_{23}$H$_{44}$N$_3$O$_5$ [M+H]$^+$, 442.3281; found, 442.3284. [α]$_D^{22}$=+2.7° (c=0.5, DMSO).

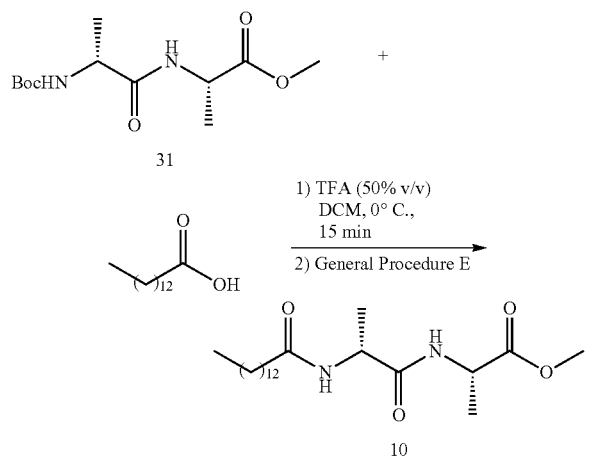

Compound 10 was prepared from compound 31 (720 mg) following the same procedure as described for the preparation of compound 8. Compound 10 was purified by preparative HPLC as described in the Materials and Methods above herein, but could not be fully resolved from residual myristic acid (86% pure based on $^1$H-NMR. 30% yield as a white solid). $^1$H NMR (400 MHz DMSO-d$_6$): δ (ppm)=8.22 (d, J=7.2 Hz, 1H), 7.90 (d, J=7.8 Hz, 1H), 4.32 (quint, J=7.4 Hz, 1H), 4.25 (quint, J=7.2 Hz, 1H), 3.61 (s, 3H), 1.50-1.41 (m, 2H), 1.34-1.13 (m, 28H), 0.85 (t, J=6.8 Hz, 3H). $^{13}$C NMR (400 MHz, DMSO-d$_6$) δ (ppm)=173.0*, 172.9, 172.4*, 172.2, 171.83*, 171.82, 51.8, 47.6*, 47.4, 45.9*, 45.8, 35.1, 31.3, 29.1, 29.05, 29.01, 28.9, 28.8, 28.7, 28.6, 25.94*, 25.86, 25.2, 22.1, 18.5, 18.2*, 17.1, 16.8*, 13.9. HRMS (ESI): calcd for C$_{21}$H$_{41}$N$_2$O$_4$ [M+H]$^+$, 385.3066; found, 385.3058. [α]$_D^{22}$=−2.8° (c=1.0, DMSO).

*Denotes a rotamer

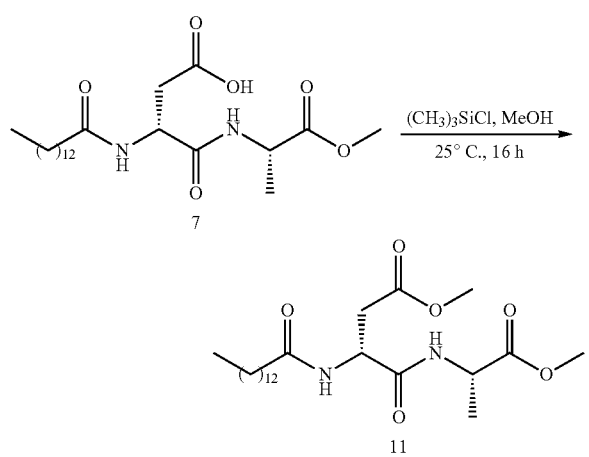

To an oven-dried round bottom flask was added compound 7 (30 mg, 1.0 equiv) and trimethylsilyl chloride (20 μL, 2 equiv) was added under N$_2$. The suspension was then dissolved in anhydrous methanol (0.5 mL, 42 equiv) and stirred at room temperature overnight. The reaction was concentrated in vacuo and the resulting solid was purified by preparative HPLC according to the procedure described in the Materials and Methods above herein to afford 11 as a white solid (13 mg, 43% yield after prep HPLC). $^1$H NMR (600 MHz DMSO-d$_6$): δ (ppm)=8.26 (d, J=7.3 Hz, 1H), 8.12 (d, J=8.3 Hz, 1H), 4.66 (td, J=8.2, 6.1 Hz, 1H), 4.25 (p, J=7.2 Hz, 1H), 3.61 (s, 3H), 3.56 (s, 3H), 2.70† (dd, J=15.8, 6.1 Hz, 1H), 2.09 (t, J=7.4 Hz, 2H), 1.55-1.39 (m, 2H), 1.33-1.11 (m, 23H), 0.85 (t, J=6.8 Hz, 3H). $^{13}$C NMR (500 MHz, DMSO-d$_6$) δ (ppm)=172.6, 172.3, 170.4, 170.2, 51.8, 51.4, 48.9, 47.6, 36.2, 35.1, 31.3, 29.04, 29.00, 28.9, 28.8, 28.7, 28.5, 25.2, 22.1, 17.0, 13.9. HRMS (ESI): calcd for C$_{23}$H$_{43}$N$_2$O$_6$ [M+H]$^+$, 443.3121; found, 443.3106. [α]$_D^{22}$=+14.4° (c=0.7, DMSO).

† See "Note on NMR spectra" at the beginning of this section 21 distinct $^{13}$C signals are observed for this substrate (23 are expected), which is likely due to the close overlap of peaks from the myristoyl group in the 28.5-29 ppm range.

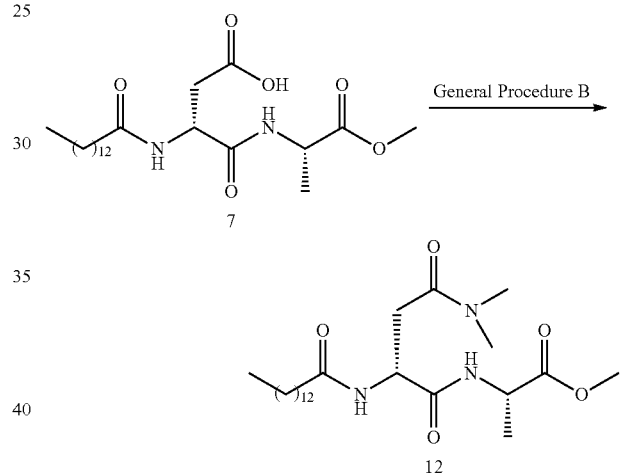

Compound 12 was prepared from compound 7 (30 mg, 1.0 equiv) and dimethylamine (as a 2 M solution in THF, 52.5 μL, 1.5 equiv) according to General Procedure B. Crude 12 was isolated as an off-white solid after work-up (38 mg, quantitative crude yield). This solid was dissolved in DMSO and purified by preparative HPLC according to the procedure described in the General Materials and Methods to afford pure 12 as a white solid (5.7 mg, 18% final yield). $^1$H NMR (500 MHz DMSO-d$_6$): δ (ppm)=8.11 (d, J=7.2 Hz, 1H), 7.99 (d, J=8.1 Hz, 1H), 4.62 (dt, J=8.2, 6.7 Hz, 1H), 4.22 (quint, J=7.2 Hz, 1H), 3.58 (s, 3H), 2.93 (s, 3H), 2.77 (s, 3H), 2.64 (dd, J=15.9, 6.5 Hz, 1H), 2.56 (dd, J=15.9, 6.8 Hz, 1H), 2.06 (t, J=7.4 Hz, 2H), 1.44 (m, 2H), 1.26-1.18 (m, 23H), 0.83 (t, J=6.9 Hz, 3H). $^{13}$C NMR (500 MHz, DMSO-d$_6$) δ (ppm)=δ172.8, 172.1, 171.0, 169.1, 51.8, 49.3, 47.6, 36.70, 36.68, 35.2, 34.8, 31.3, 29.03, 29.0, 28.9, 28.8, 28.7, 28.5, 25.2, 22.1, 17.1, 13.9. HRMS (ESI): calcd for C$_{24}$H$_{46}$N$_3$O$_5$ [M+H]$^+$, 456.3437; found, 456.3423. [α]$_D^{22}$=+18.2° (c=0.48, DMSO).

21 distinct $^{13}$C signals are observed for this substrate (23 are expected), which is likely due to the close overlap of peaks from the myristoyl group in the 28.5-29 ppm range.

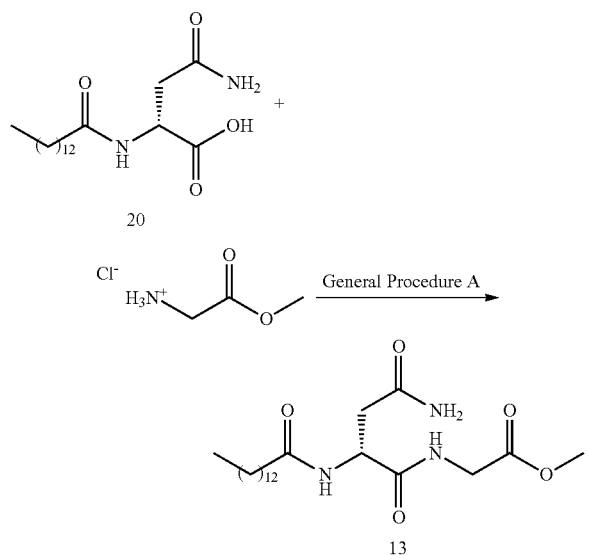

Substrate 13 was prepared from 20 (14.2 mg) and glycine methylester hydrochloride (6.3 mg) using General Procedure A. Crude 13 was isolated as a white solid after work-up (18 mg, quantitative). This solid was dissolved in DMSO and purified by preparative HPLC according to the procedure described in the General Materials and Methods to afford pure 13 as a white solid (12 mg, 70%). $^1$H NMR (400 MHz DMSO-$d_6$): δ (ppm)=8.11 (t, J=5.9 Hz, 1H), 7.99 (d, J=8.1 Hz, 1H), 7.27 (s, 1H), 6.84 (s, 1H), 4.59 (td, J=8.1, 5.4 Hz, 1H), 3.89-3.73 (m, 2H), 3.61 (s, 3H), 2.35† (dd, J=15.4, 8.3 Hz, 1H), 2.09 (t, J=7.5 Hz, 2H), 1.46 (t, J=7.1 Hz, 2H), 1.23 (d, J=2.4 Hz, 20H), 0.90-0.81 (m, 3H). $^{13}$C NMR (400 MHz, DMSO-$d_6$) δ (ppm)=172.2, 171.8, 171.3, 170.1, 51.6, 49.3, 40.7, 37.2, 35.2, 31.3, 29.1, 29.05, 29.01, 28.93, 28.9, 28.7, 28.6, 25.1, 22.1, 13.9. HRMS (ESI): calcd for $C_{21}H_{40}N_3O_5$ [M+H]$^+$, 414.2968; found, 414.2951. $[α]_D^{22}$=+ 8.5° (c=0.98, DMSO).

† See "Note on NMR spectra" at the beginning of this section 20 distinct $^{13}$C signals are observed for this substrate (21 are expected), which is likely due to the close overlap of peaks from the myristoyl group in the 28.5-29 ppm range.

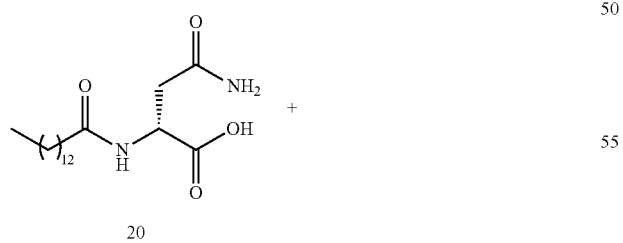

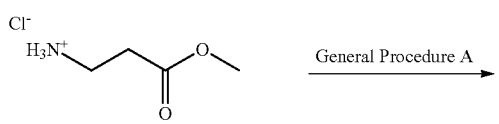

Substrate 14 was prepared from 20 (13.5 mg) and β-alanine methylester hydrochloride (6.6 mg) using General Procedure A. Crude 14 was isolated as a white solid after work up (18.9 mg, quantitative). This solid was dissolved in DMSO and purified by preparative HPLC according to the procedure described in the Materials and Methods above herein to afford 14 as a white solid (14 mg, 59%). $^1$H NMR (400 MHz DMSO-$d_6$): δ (ppm)=7.88 (d, J=8.0 Hz, 1H), 7.74 (t, J=5.8 Hz, 1H), 7.21 (s, 1H), 6.78 (s, 1H), 4.43 (td, J=7.8, 5.9 Hz, 1H), 3.55 (s, 3H), 3.27-3.16 (m, 2H), 2.41 (dd, J=15.3, 6.0 Hz, 1H), 2.39 (t, J=6.9 Hz, 2H), 2.27 (dd, J=15.3, 7.6 Hz, 1H), 2.04 (t, J=7.5 Hz, 2H), 1.42 (q, J=7.1 Hz, 2H), 1.20 (s, 20H), 0.87-0.74 (m, 3H). $^{13}$C NMR (400 MHz, DMSO-$d_6$) δ (ppm)=172.1, 171.7, 171.4, 171.2, 51.3, 49.6, 37.3, 35.2, 34.7, 33.5, 31.3, 29.1, 29.04, 29.01, 29.0, 28.9, 28.8, 28.7, 28.6, 25.1, 22.1, 14.0. HRMS (ESI): calcd for $C_{22}H_{42}N_3O_5$ [M+H]$^+$, 428.3124; found, 428.3107. $[α]_D^{22}$=+ 5.5° (c=0.43, DMSO).

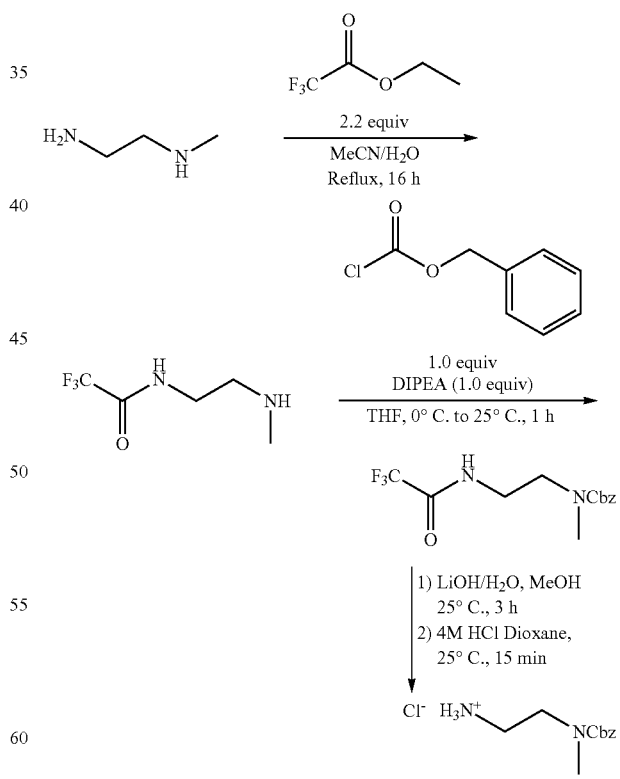

Intermediate 33 was synthesized has previously reported.[17] N-Methylethylenediamine (2.6 g, 1.0 equiv), ethyl trifluoroacetate (3.5 mL, 2.2 equiv) and water (0.76 mL, 1.2 equiv) were combined in acetonitrile (35 mL) and refluxed with stirring overnight. Solvents were evaporated under vacuum and the residue was re-evaporated with i-PrOH three times. The trifluoroacetamide product was recrystallized from DCM and filtered. This product (4.0 g, 1.0 equiv) was then dissolved in THF (26 mL) with DIPEA (4.09 mL, 1.0 equiv) and cooled to 0° C., at which point benzyloxycarbonyl chloride (3.35 mL, 1.0 equiv) was added dropwise. The reaction was warmed to room temperature and stirred for an additional 1 hour. Solvent was then evaporated in vacuo and the resulting residue dissolve in EtOAc. The organic layer was washed with 5% aqueous NaHCO$_3$ twice and brine. The organic layer was evaporated to provide the benzyloxy-protected trifluoroacetamide product as a yellowish oil. This oil was then dissolved in MeOH (78 mL) and a solution of LiOH (1.12 g, 2.0 equiv) in water (9.5 mL) was added and the mixture stirred for 3 hours at room temperature. Solvents were evaporated to 75% of the initial volume and then diluted with water (30 mL). The solution was extracted twice with EtOAc. The combined organic layers were then washed with brine (50 mL), dried over Mg$_2$SO$_4$, filtered, and the filtrate concentrated in vacuo. The resulting residue was then dissolved in Et$_2$O (25 mL) and treated with 4N HCl in dioxane (7.7 mL). After 15 minutes, the solvent was removed in vacuo to afford HCl salt 33.

solid (2.08 g, 73%). $^1$H NMR (600 MHz DMSO-d$_6$): δ (ppm)=7.92 (br s, 1H); 7.39-7.29 (m, 5H); 7.24 (br s, 1H); 6.87 (br s, 1H); 6.83-6.77 (m, 1H); 5.06 (s, 2H); 4.23-4.14 (m, 1H); 3.30-3.24 (m, 2H); 3.24-3.14 (m, 2H); 2.87 (s, 1.5H)*; 2.84 (s, 1.5H)*; 2.42-2.31 (m, 2H); 1.37 (s, 9H). 13C NMR (500 MHz, DMSO-d$_6$): δ (ppm)=171.6, 171.5, 155.5, 155.3*, 155.0, 137.1, 137.0*, 128.4, 127.72, 127.69*, 127.40, 127.37*, 78.1, 66.1, 51.4, 48.0, 47.6*, 37.3, 37.0, 36.99*, 35.2, 34.5*, 28.2. HRMS (ESI): calcd for C$_{20}$H$_{31}$N$_4$O$_6$ [M+H]$^+$, 423.2238; found, 423.2247. [α]$_D^{23}$=+4.8° (c=1.0, DMSO).

* Denotes a rotamer

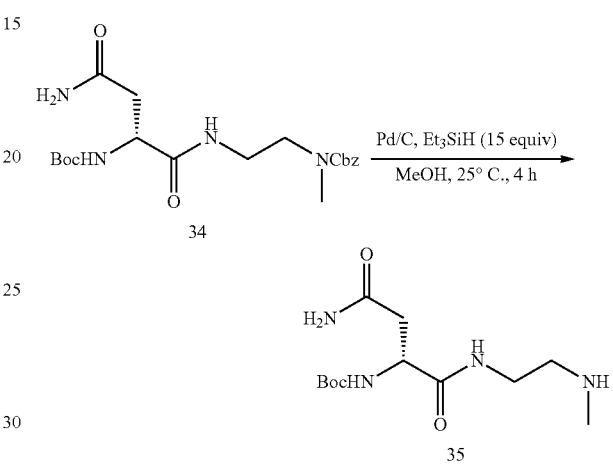

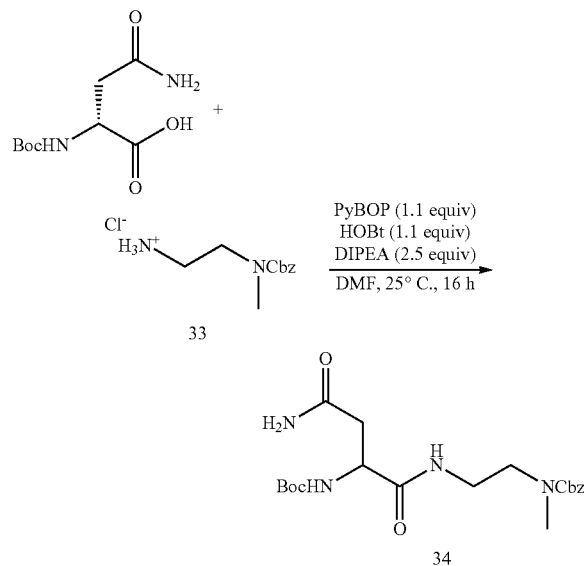

To a flame-dried round bottom flask containing a stir bar was added amine hydrochloride salt 33 (1.65 g, 1.0 equiv), N-Boc-D-Asparagine (1.57 g, 1.0 equiv), PyBOP (3.87 g, 1.1 equiv), HOBt (1.00 g, 1.1 equiv), and dry DMF (13.5 mL, 0.5 M). The reaction mixture was cooled to 0° C. and DIPEA (2.93 mL, 2.5 equiv) was added dropwise under N$_2$. The resulting reaction mixture was then warmed to room temperature over 12 h. The reaction was then quenched with aqueous 1M HCl (10 mL) and diluted with EtOAc (20 mL). The layers were separated and the aqueous layer extracted 3 times with EtOAc. The combined organic layers were then washed with saturated aqueous NaHCO$_3$, twice with water, and brine. The organic layer was dried over Na$_2$SO$_4$, filtered, and the resulting filtrate concentrated in vacuo to give a crude solid. The solid was triturated with Et$_2$O (20 mL) and dried under vacuum to afford carbamate 34 as a light brown To a round bottom flask equipped with a stir bar was added palladium on carbon (22 mg, 10% Pd by weight) and water (0.5 mL) under N$_2$. Separately, carbamate 34 (318 mg, 1.0 equiv) was suspended in MeOH (6 mL) in a vial. The mixture was sonicated in order to uniformly suspend the solid and the resulting slurry was transferred to the reaction flask via syringe. The vial was rinsed with additional MeOH (2 mL) which was added to the reaction vessel. Triethylsilane (1.1 mL, 15.0 equiv) was added dropwise while the reaction mixture was stirred at room temperature and gas evolution was observed. The reaction was stirred for 4 hours, during which time the mixture went from a gray slurry to a clear solution with only the black catalyst visible. The reaction was then filtered over Celite to remove the catalyst and the filtrate concentrated in vacuo. The resulting residue was then dissolved in isopropanol and concentrated in vacuo twice to afford crude amine 35, which was used in the subsequent step without further purification.

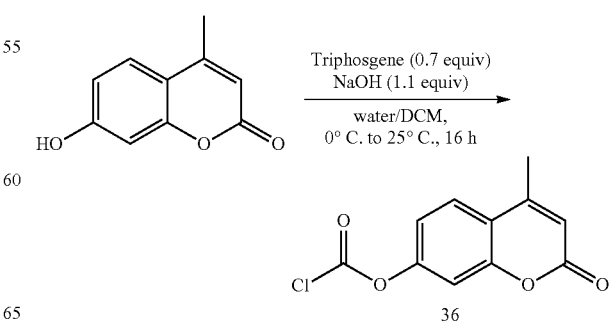

Intermediate 36 was prepared as previously described by Hesserodt and coworkers.[18] To a round bottom flask under $N_2$ was added triphosgene (1.26 g, 0.7 equiv) under $N_2$. Dry DCM (30 mL) was added and the solution cooled to 0° C. 7-Hydroxy-4-methylcoumarin (1.08 g, 1.0 equiv) was then added in one portion. To the resulting white suspension was added 2M aqueous NaOH (3.3 mL) dropwise. The reaction was stirred at 0° C. for 1 hour, then warmed to room temperature and stirred overnight. The precipitated white solid was filtered and washed with cold DCM affording 36 as a white solid (0.570 g, 40%). $^1$H NMR (500 MHz, DMSO-$d_6$) δ 7.91 (d, J=8.7 Hz, 1H), 7.59 (d, J=2.3 Hz, 1H), 7.48 (dd, J=8.7, 2.4 Hz, 1H), 6.44 (d, J=1.5 Hz, 1H), 2.46 (s, 3H).

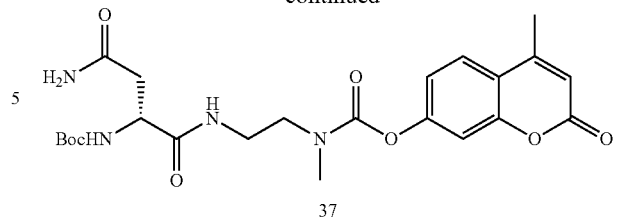

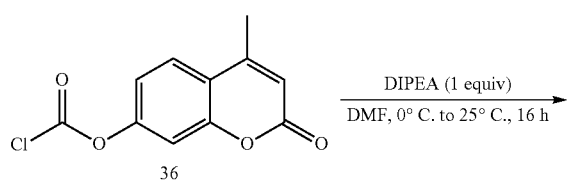

To a flame-dried round bottom flask equipped with a stir bar was added 35 (181 mg, 1.0 equiv) and 36 (165 mg, 1.1 equiv) under $N_2$. Dry DMF (6.3 mL) was added and the flask cooled to 0° C. DIPEA (121 μL, 1.1 equiv) was added dropwise and the reaction stirred overnight at room temperature. The reaction was diluted with water (30 mL) and extracted twice with DCM (30 mL). The combined organic layers were washed with 5% aqueous LiCl, 1M HCl, 0.1M NaOH, and brine. The organic layer was then concentrated in vacuo and purified by flash chromatography (silica, EtOAc:MeOH 90:10, isocratic). Fractions containing the desired product were concentrated in vacuo to afford 37 as a white solid (175 mg, 57%). $^1$H NMR (500 MHz DMSO-$d_6$): δ (ppm)=8.12-7.95 (m, 1H), 7.78 (d, J=8.6 Hz, 1H), 7.32-7.23 (m, 2H), 7.20 (ddd, J=8.8, 6.5, 2.3 Hz, 1H), 6.88 (t, J=6.7 Hz, 2H), 6.37 (s, 1H), 4.21 (m, 1H), 3.51-3.21 (m, 4H), 3.05 (s, 1.5H)*, 2.92 (s, 1.5H)*, 2.44 (s, 3H), 2.42-2.29 (m, 2H), 1.37 (s, 9H). $^{13}$C NMR (500 MHz, DMSO-$d_6$) δ 171.8, 171.6, 159.7, 155.1, 153.9, 153.5, 153.3, 153.0, 126.0, 118.4, 116.9, 113.4, 109.9, 109.8*, 78.2, 51.5, 48.5, 48.46*, 37.40*, 37.3, 36.6, 35.7, 35.3*, 28.2, 18.2. HRMS (ESI): calcd for $C_{23}H_{31}N_4O_8$ [M+H]$^+$, 491.2142; found, 491.2124.

* denotes a rotamer

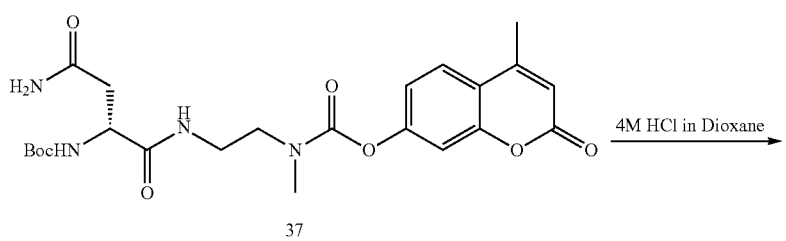

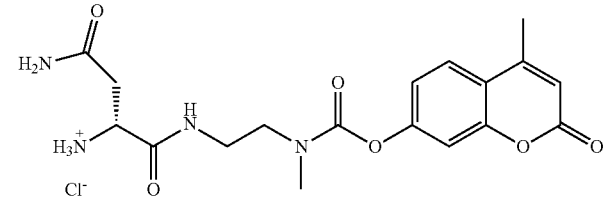

To a round bottom flask with a stir bar was added 37 (190 mg, 1.0 equiv). The starting material was dissolved in DCM (4 mL) and 4M HCl in dioxane (1.94 mL) was added. After stirring for approximately 10 minutes at room temperature, a white precipitate appeared. After 30 minutes, the reaction was sparged with $N_2$ for 10 minutes while stirring to drive off residual HCl. The reaction was then concentrated in vacuo, affording the amine HCl salt 38 as a white solid, which was used without further purification.

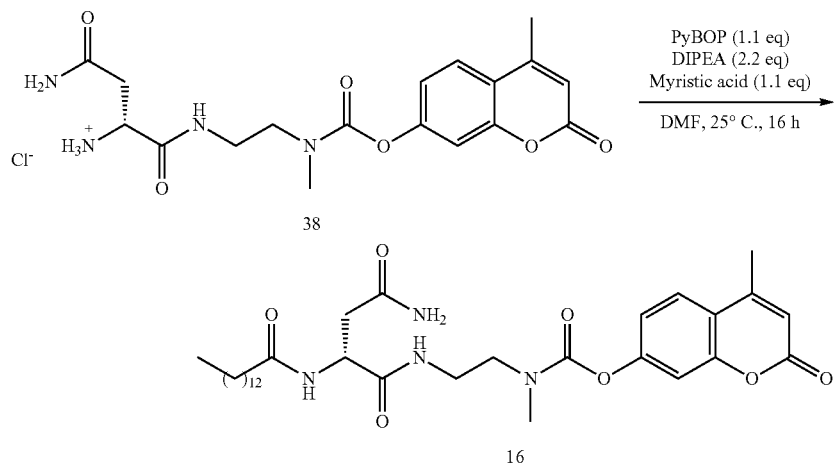

To an oven dried round-bottom flask were added crude 38 (97 mg, 1.0 equiv), myristic acid (52 mg, 1.2 equiv), PyBOP (143 mg, 1.2 equiv), HOBt (42 mg, 1.2 eq) and anhydrous DMF (2.3 mL) under $N_2$. DIPEA (84 µL, 2.1 equiv) was added dropwise and the reaction allowed to stir overnight at room temperature. The reaction was diluted with water, extracted twice with DCM (5-10 mL), and the combined organic layers were washed with 5% LiCl, 1M HCl, sat. aq. $NaHCO_3$, and brine. The organic layer was dried over $Na_2SO_4$, filtered, and the filtrate concentrated in vacuo. The resulting solid was dissolved in a minimum volume of DMSO and purified by preparative HPLC as described in the General Materials and Methods to afford pure 16 as a white solid (18 mg, 13% yield over three steps). $^1$H NMR (400 MHz, DMSO-$d_6$): δ (ppm)=8.06-7.88 (m, 2H), 7.78 (d, J=8.7 Hz, 1H), 7.33-7.24 (m, 2H), 7.20 (dt, J=8.7, 2.6 Hz, 1H), 6.83 (s, 1H), 6.37 (d, J=1.4 Hz, 1H), 4.59-4.45 (m, 1H), 3.48-3.39 (m, 1H), 3.39-3.22 (m, 10H), 3.04* (s, 1.5H), 2.93* (s, 1.5H), 2.44 (s, 3H), 2.35† (dd, J=15.2, 7.7 Hz, 1H), 2.13-2.00 (td, J=7.5, 5.0 Hz, 2H), 1.44 (m, 2H), 1.31-1.10 (m, 20H), 0.85 (t, J=6.6 Hz, 3H). $^{13}$C NMR (400 MHz, DMSO-$d_6$): δ (ppm)=172.1*, 172.0, 171.49*, 171.47, 171.42*, 171.4, 166.0, 159.7, 153.9, 153.5, 153.4, 153.03*, 153.0, 126.0, 118.43*, 118.42, 116.86*, 116.85, 113.4, 109.92*, 109.87, 49.8*, 49.7, 48.5*, 48.4, 37.3*, 37.2, 36.7, 35.6, 35.3*, 35.2, 31.3, 29.1, 29.04, 29.01, 28.9, 28.8, 28.70, 28.66, 25.10*, 25.07, 22.1, 18.2, 13.9. HRMS (ESI): calcd for $C_{32}H_{49}N_4O_7$ $[M+H]^+$, 601.3601; found, 601.3612. $[α]_D^{22}$=+35.1° (c=1.0, DMSO).

§ the high integration value of this peak results from overlap with residual water. HSQC data shows the expected C and H signals for the ethylenediamine linker in this region

* denotes a rotamer

† see "Note on NMR spectra" at the beginning of this section

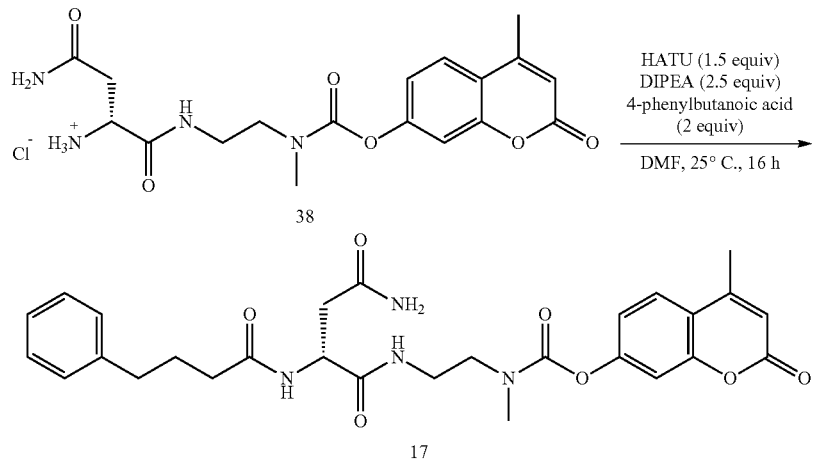

To an oven-dried round bottom flask equipped with a stir bar were added 38 (44.9 mg, 1.0 equiv), 4-phenylbutanoic acid (38.4 mg, 2.0 equiv), HATU (65.5 mg, 1.5 equiv) and anhydrous DMF (1.14 mL) under $N_2$. DIPEA (50 μL, 2.5 equiv) was added and the reaction allowed to stir at room temperature overnight. The reaction was diluted with water, extracted twice with DCM (5 reaction volumes). The combined organic layers were washed with 5% LiCl, 1M HCl, sat. aq. $NaHCO_3$, and brine. The organic layer was dried over $Na_2SO_4$, filtered, and the filtrate concentrated in vacuo to give a white solid. This solid was then dissolved in a minimum volume of DMSO and purified by preparative HPLC as described in the Materials and Methods to afford 17 as a white solid (38.9 mg, 63% yield over two steps). $^1$H NMR (600 MHz, DMSO-$d_6$): δ (ppm)=δ 8.12-7.93 (m, 2H), 7.77 (d, J=8.6 Hz, 1H), 7.36-7.10 (m, 7H), 6.87 (s, 1H), 6.36 (s, 1H), 4.60-4.47 (m, 1H), 3.46-3.23 (m, 6H)§, 3.04 (s, 1.5H)*, 2.91 (s, 1.5H)*, 2.56-2.48 (m, 4H) 2.47 (dd, J=9.6, 5.5 Hz, 1H), 2.43 (s, 3H), 2.37† (dd, J=15.2, 8.2 Hz, 1H), 2.17-2.06 (m, 2H), 1.82-1.68 (m, 2H). $^{13}$C NMR (500 MHz, DMSO-$d_6$): δ (ppm)=172.27, 172.25*, 172.0*, 171.95, 171.92*, 171.9, 160.2, 154.3, 153.9, 153.82*, 153.8, 153.5*, 153.48, 142.3, 128.78, 128.75*, 128.7, 126.5, 126.1, 118.9, 117.3, 113.8, 110.4, 110.3*, 50.33, 50.28*, 48.94*, 48.9, 37.8, 37.75*, 37.7, 37.1, 36.1*, 35.8, 35.2*, 35.1, 27.42, 27.4*, 18.6. HRMS (ESI): calcd for $C_{28}H_{33}N_4O_7$ [M+H]$^+$, 537.2349; found, 537.234. $[α]_D^{23}$=+7.2° (c=0.54, DMSO).

* Denotes a rotamer
† See "Note on NMR spectra" at the beginning of this section
§ The integral values of these peaks are higher than expected due to overlaps with the water and DMSO solvent residuals. 2D NMR experiments show the expected connectivities.

SUPPLEMENTAL REFERENCES (1) Vizcaino, M. I., and Crawford, J. M. (2015) The colibactin warhead crosslinks DNA. *Nat. Chem.* 7, 411-417.
(2) Brotherton, C. A., Wilson, M., Byrd, G., and Balskus, E. P. (2015) Isolation of a metabolite from the pks island provides insights into colibactin biosynthesis and activity. *Org. Lett.* 17, 1545-1548.
(3) Bian, X., Plaza, A., Zhang, Y., and Miller, R. (2015) Two more pieces of the colibactin genotoxin puzzle from *Escherichia coli* show incorporation of an unusual 1-aminocyclopropanecarboxylic acid moiety. *Chem. Sci.* 6, 3154-3160.
(4) Healy, A. R., Nikolayevskiy, H., Patel, J. R., Crawford, J. M., and Herzon, S. B. (2016) A Mechanistic Model for Colibactin-Induced Genotoxicity. *J. Am. Chem. Soc.* 138, 15563-15570.
(5) Li, Z. R., Li, Y., Lai, J. Y. H., Tang, J., Wang, B., Lu, L., Zhu, G., Wu, X., Xu, Y., and Qian, P. Y. (2015) Critical Intermediates Reveal New Biosynthetic Events in the Enigmatic Colibactin Pathway. *ChemBioChem* 16, 1715-1719.
(6) Zha, L., Wilson, M. R., Brotherton, C. A., and Balskus, E. P. (2016) Characterization of Polyketide Synthase Machinery from the pks Island Facilitates Isolation of a Candidate Precolibactin. *ACS Chem. Biol.* 11, 1287-1295.
(7) Li, Z. R., Li, J., Gu, J. P., Lai, J. Y. H., Duggan, B. M., Zhang, W. P., Li, Z. L., Li, Y. X., Tong, R. B., Xu, Y., Lin, D. H., Moore, B. S., and Qian, P. Y. (2016) Divergent biosynthesis yields a cytotoxic aminomalonate-containing precolibactin. *Nat. Chem. Biol.* 12, 773-775.
(8) Dubois, D., Baron, O., Cougnoux, A., Delmas, J., Pradel, N., Boury, M., Bouchon, B., Bringer, M.-A., Nougayrede, J.-P., Oswald, E., and Bonnet, R. (2011) ClbP Is a Prototype of a Peptidase Subgroup Involved in Biosynthesis of Nonribosomal Peptides. *J. Biol. Chem.* 286, 35562-35570.
(9) Xue, M., Shine, E., Wang, W., Crawford, J. M., and Herzon, S. B. (2018) Characterization of Natural Colibactin-Nucleobase Adducts by Tandem Mass Spectrometry and Isotopic Labeling. Support for DNA Alkylation by Cyclopropane Ring Opening. *Biochemistry* 57, 6391-6394.
(10) Wilson, M. R., Jiang, Y., Villalta, P. W., Stornetta, A., Boudreau, P. D., Cana, A., Brennan, C. A., Chun, E., Ngo, L., Samson, L. D., Engelward, B. P., Garrett, W. S., Balbo, S., and Balskus, E. P. (2019) The human gut bacterial genotoxin colibactin alkylates DNA. *Science.* 363, eaar7785.
(11) Healy, A. R., Vizcaino, M. I., Crawford, J. M., and Herzon, S. B. (2016) Convergent and Modular Synthesis of Candidate Precolibactins. Structural Revision of Precolibactin A. *J. Am. Chem. Soc.* 138, 5426-5432.
(12) Xue, M., Shine, E. E., Wang, W., Crawford, J. M., and Herzon, S. B. (2018) Characterization of natural colibactin-nucleobase adducts by tandem MS and isotopic labeling. Support for DNA alkylation by cyclopropane ring opening. *Biochemistry* 57, 6391-6394.

(13) Brotherton, C. A., and Balskus, E. P. (2013) A Prodrug Resistance Mechanism Is Involved in Colibactin Biosynthesis and Cytotoxicity. *J. Am. Chem. Soc.* 135, 3359-3362.

(14) Romano, K. A., Vivas, E. I., Amador-Noguez, D., and Rey, F. E. (2015) Intestinal Microbiota Composition Modulates Choline Bioavailability from Diet and Accumulation of the Proatherogenic Metabolite Trimethylamine-N-Oxide. *MBio* 6, 1-8.

(15) Zha, L., Jiang, Y., Henke, M. T., Wilson, M. R., Wang, J. X., Kelleher, N. L., and Balskus, E. P. (2017) Colibactin assembly line enzymes use S-adenosylmethionine to build a cyclopropane ring. *Nat. Chem. Biol.* 13, 1063-1065.

(16) Eidam, O., Romagnoli, C., Dalmasso, G., Barelier, S., Caselli, E., Bonnet, R., Shoichet, B. K., and Prati, F. (2012) Fragment-guided design of subnanomolar Beta-lactamase inhibitors active in vivo. *Proc. Natl. Acad. Sci.* 109, 17448-17453.

(17) Jenkins, T. E., and Kolesnikov, A. (2008) Prodrugs of peripheral phenolic opiod agonists. USA.

(18) Prost, M., Canaple, L., Samarut, J., and Hasserodt, J. (2014) Tagging live cells that express specific peptidase activity with solid-state fluorescence. *ChemBioChem* 15, 1413-1417.

---

What is claimed herein is:

1. A composition comprising a compound of Structure I:

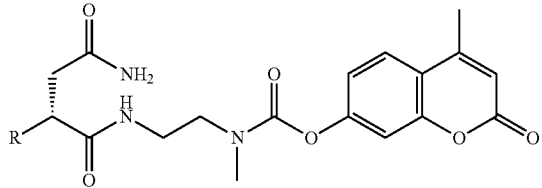

Structure I wherein R is selected from:

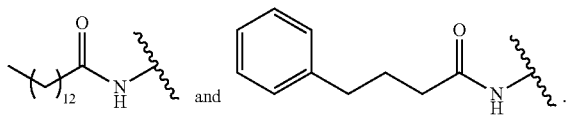

2. A method of measuring ClbP activity in a sample, the method comprising:

contacting the sample with a composition of claim 1; and
   measuring fluorescence;
   wherein increased fluorescence relative to a reference sample indicates an increased level of ClbP activity relative to the reference sample.

3. The method of claim 2, wherein an increased level of ClbP activity indicates an increased level or metabolic activity of pks$^+$*E. coli*.

4. The method of claim 2 where the contacted sample is obtained from a subject.

5. The method of claim 4, wherein the subject has, or is at risk of having colorectal cancer.

6. The method of claim 4, wherein the sample comprises bacterial cells or bacterial cell lysates.

7. The composition of claim 1, wherein the compound is a ClbP substrate.

* * * * *

SEQUENCE LISTING

<160> NUMBER OF SEQ ID NOS: 3

<210> SEQ ID NO 1
<211> LENGTH: 504
<212> TYPE: PRT
<213> ORGANISM: Escherichia coli

<400> SEQUENCE: 1

```
Met Thr Ile Met Glu His Val Ser Ile Lys Thr Leu Tyr His Leu Leu
1               5                   10                  15

Cys Cys Met Leu Leu Phe Ile Ser Ala Met Cys Ala Leu Ala Gln Glu
                20                  25                  30

His Glu Pro Ile Gly Ala Gln Asp Glu Arg Leu Ser Thr Leu Ile His
            35                  40                  45

Gln Arg Met Gln Glu Ala Lys Val Pro Ala Leu Ser Val Ser Val Thr
        50                  55                  60

Ile Lys Gly Val Arg Gln Arg Phe Val Tyr Gly Val Ala Asp Val Ala
65                  70                  75                  80

Ser Gln Lys Ala Asn Thr Leu Asp Thr Val Tyr Glu Leu Gly Ser Met
                85                  90                  95

Ser Lys Ala Phe Thr Gly Leu Val Val Gln Ile Leu Ile Gln Glu Gly
            100                 105                 110

Arg Leu Arg Gln Gly Asp Asp Ile Ile Thr Tyr Leu Pro Glu Met Arg
        115                 120                 125

Leu Asn Tyr Gln Gly Lys Pro Ala Ser Leu Thr Val Ala Asp Phe Leu
130                 135                 140

Tyr His Thr Ser Gly Leu Pro Phe Ser Thr Leu Ala Arg Leu Glu Asn
145                 150                 155                 160

Pro Met Pro Gly Ser Ala Val Ala Gln Gln Leu Arg Asn Glu Asn Leu
                165                 170                 175

Leu Phe Ala Pro Gly Ala Lys Phe Ser Tyr Ala Ser Ala Asn Tyr Asp
            180                 185                 190

Val Leu Gly Ala Val Ile Glu Asn Val Thr Gly Lys Thr Phe Thr Glu
        195                 200                 205

Val Ile Ala Glu Arg Leu Thr Gln Pro Leu Gly Met Ser Ala Thr Val
    210                 215                 220

Ala Val Lys Gly Asp Glu Ile Ile Val Asn Lys Ala Ser Gly Tyr Lys
225                 230                 235                 240

Leu Gly Phe Gly Lys Pro Val Leu Phe His Ala Pro Leu Ala Arg Asn
                245                 250                 255

His Val Pro Ala Ala Tyr Ile His Ser Thr Leu Pro Asp Met Glu Ile
            260                 265                 270
```

```
Trp Ile Asp Ala Trp Leu His Arg Lys Ala Leu Pro Ala Thr Leu Arg
            275                 280                 285

Glu Ala Met Ser Asn Ser Trp Arg Gly Asn Ser Asp Val Pro Leu Ala
        290                 295                 300

Ala Asp Asn Arg Ile Leu Tyr Ala Ser Gly Trp Phe Ile Asp Gln Asn
305                 310                 315                 320

Gln Gly Pro Tyr Ile Ser His Gly Gly Gln Asn Pro Asn Phe Ser Ser
                325                 330                 335

Cys Ile Ala Leu Arg Pro Asp Gln Gln Ile Gly Ile Val Ala Leu Ala
                340                 345                 350

Asn Met Asn Ser Asn Leu Ile Leu Gln Leu Cys Ala Asp Ile Asp Asn
            355                 360                 365

Tyr Leu Arg Ile Gly Lys Tyr Ala Asp Gly Ala Gly Asp Ala Ile Thr
            370                 375                 380

Ala Thr Asp Thr Leu Phe Val Tyr Leu Thr Leu Leu Cys Phe Trp
385                 390                 395                 400

Gly Ala Val Val Val Arg Gly Ala Phe Arg Val Tyr Arg Ala Thr
                405                 410                 415

Ala His Gly Pro Gly Lys Gln Gln Arg Leu Arg Leu Arg Val Arg Asp
                420                 425                 430

Tyr Ile Ile Ala Leu Ala Val Pro Gly Leu Val Ala Ala Met Leu Tyr
            435                 440                 445

Val Ala Pro Gly Ile Leu Ser Pro Gly Leu Asp Trp Arg Phe Ile Leu
450                 455                 460

Val Trp Gly Pro Ser Ser Val Leu Ala Ile Pro Phe Gly Ile Ile Leu
465                 470                 475                 480

Leu Ala Phe Val Leu Thr Leu Asn His Gln Ile Lys Arg Ile Leu Leu
                485                 490                 495

His Asn Lys Glu Trp Asp Asp Glu
            500

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccaccatcac catcactgag atccggctgc taacaaagcc cgaaag                46

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcagtgatg gtgatggtgg tggtggtggt ggtgctcgag ctc                   43
```